(12) United States Patent
Sturino et al.

(10) Patent No.: US 9,708,332 B2
(45) Date of Patent: Jul. 18, 2017

(54) RESPIRATORY SYNCYTIAL VIRUS INHIBITORS

(71) Applicant: MEDIVIR AB, Huddinge (SE)

(72) Inventors: Claudio Sturino, Burlington (CA); Teddy Halmos, Burlington (CA); Anne Decor, Burlington (CA); Martin Duplessis, Burlington (CA); Patrick Deroy, Burlington (CA); Araz Jakalian, Burlington (CA); Louis Morency, Burlington (CA); Cyrille Kuhn, Ridgefield, CT (US); Chantal Grand-Maitre, Burlington (CA); Martin Tremblay, Burlington (CA); Christian Brochu, Burlington (CA)

(73) Assignee: MEDIVIR AB, Stockholm (SE)

( * ) Notice: Subject to any disclaimer, the term of this patent is extended or adjusted under 35 U.S.C. 154(b) by 0 days.

(21) Appl. No.: 15/032,855

(22) PCT Filed: Oct. 29, 2013

(86) PCT No.: PCT/US2013/067276
§ 371 (c)(1),
(2) Date: Apr. 28, 2016

(87) PCT Pub. No.: WO2015/065338
PCT Pub. Date: May 7, 2015

(65) Prior Publication Data
US 2016/0272646 A1    Sep. 22, 2016

(51) Int. Cl.
| | | |
|---|---|---|
| *C07D 487/04* | (2006.01) |
| *C07D 403/06* | (2006.01) |
| *C07D 403/14* | (2006.01) |
| *C07D 401/06* | (2006.01) |
| *C07D 401/14* | (2006.01) |
| *C07D 407/14* | (2006.01) |
| *C07D 413/06* | (2006.01) |
| *C07D 413/14* | (2006.01) |
| *A61K 31/517* | (2006.01) |
| *A61K 31/519* | (2006.01) |
| *A61P 31/14* | (2006.01) |
| *C07D 413/04* | (2006.01) |
| *C07D 471/04* | (2006.01) |
| *C07D 405/14* | (2006.01) |
| *C07D 471/14* | (2006.01) |
| *C07D 473/06* | (2006.01) |

(52) U.S. Cl.
CPC .......... *C07D 487/04* (2013.01); *A61K 31/517* (2013.01); *A61K 31/519* (2013.01); *C07D 401/06* (2013.01); *C07D 401/14* (2013.01); *C07D 403/06* (2013.01); *C07D 403/14* (2013.01); *C07D 405/14* (2013.01); *C07D 407/14* (2013.01); *C07D 413/04* (2013.01); *C07D 413/06* (2013.01); *C07D 413/14* (2013.01); *C07D 471/04* (2013.01); *C07D 471/14* (2013.01); *C07D 473/06* (2013.01)

(58) Field of Classification Search
CPC .. C07D 487/04; C07D 403/06; A61K 31/506; A61K 31/519
USPC ........ 544/250, 251, 263, 264, 283; 514/257, 514/259.1, 263.1
See application file for complete search history.

(56) References Cited

U.S. PATENT DOCUMENTS 8,691,832 B2* 4/2014 Burnett ................ C07D 487/14
514/267
2010/0069383 A1   3/2010 Anderson et al.

FOREIGN PATENT DOCUMENTS

| WO | 0195910 A1 | 12/2001 |
| WO | 0226228 A1 | 4/2002 |
| WO | 02062290 A2 | 8/2002 |
| WO | 2004037814 A1 | 5/2004 |
| WO | 2012080451 A1 | 6/2012 |

OTHER PUBLICATIONS

Database Registry[Online] Chemical Abstracts Service, Columbus, Ohio, US; Nov. 2, 2008 (Nov. 2, 2008), "4-Quinazolinamine, 2-[(3,4-dihydro-2(1H)-isoquinolinyl)methyl]-N-[(2-thienylmethyl)-" XP002717130, Database accession No. 1069640-41-0 the whole document.
Database Registry[Online] Chemical Abstracts Service, Columbus, Ohio, US; Mar. 21, 2010 (Mar. 21, 2010), ",5-Methano-8H-pyrido[1,2-a][1,5] diazocin-8-one, 3-[[6-chloro-4-[[3-(1-methylethoxy0propyl] amino] -2-quinazolinyl]methyl]-1,2,3,4,5,6-hexahydro-,(1S,5S)-" XP002717124, Database accession No. 1212629-71-4 the whole document.

(Continued)

*Primary Examiner* — Venkataraman Balasubramanian
(74) *Attorney, Agent, or Firm* — Gorman IP Law, APC

(57) ABSTRACT

Compounds of Formula (I), wherein $R^1$, $R^2$, $R^3$, $R^4$ and n are defined herein, are useful as inhibitors of RSV.

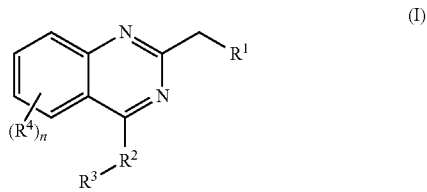

15 Claims, No Drawings

(56) References Cited

OTHER PUBLICATIONS

Database Registry[Online] Chemical Abstracts Service, Columbus, Ohio, US; Mar. 21, 2010 (Mar. 21, 2010), "1,5-Methano-8H-pyrido[1,2-a][1,5] diazocin-8-one, 3-[[6-methyl-4-(4-thiomorpholinyl) -2-quinazolinyl] methyl]-(1S,5S)-" XP002717125, Database accession No. 1212548-99-6 the whole document.

Database Registry[Online] Chemical Abstracts Service, Columbus, Ohio, US; Mar. 21, 2010 (Mar. 21, 2010), "1,5-Methano-8H-pyrido[1,2-a][1,5] diazocin-8-one, 3-[[4-(1,3-benzodioxol-5-ylamino)-8-methyl-2-quinazolinyl]methyl]-1,2,3,4,5,6-hexahydro-, (1S,5S)-" XP0027171216, Database accession No. 121261-93-0 the whole document.

Database Registry[Online] Chemical Abstracts Service, Columbus, Ohio, US; Mar. 21, 2010 (Mar. 21, 2010), "1,5-Methano-8H-pyrido[1,2-a][1,5] diazocin-8-one, 3-[[6-chloro-4-(4-morpholinyl0-2-quinazolinyl] methyl]-1,2,3,4,5,6-hexahydro-,(1S,5S)-" XP002717121, Database accession No. 121261-33-2 the whole document.

Database Registry[Online] Chemical Abstracts Service, Columbus, Ohio, US; Mar. 21, 2010 '(Mar. 21, 2010), "1,5-Methano-8H-pyrido[1,2-a][1,5] diazocin-8-one, 1,2,3,4,5,6-hexahydro-,3-[[4-[(2-thienylmethyl) amino]-2quinazolinyl]methyl]-, (1S,5S)", XP002717122, Database accession No. 1212666-65-3 the whole document.

Database Registry[Online] Chemical Abstracts Service, Columbus, Ohio, US; Mar. 21, 2010 (Mar. 21, 2010), "1,5-Methano-8H-pyrido[1,2-a][1,5] diazocin-8-one, -1,2,3,4,5,6-hexahydro-3-[[4[[(5-methyl-2-furanyl) methyl]amino]-2-quinazolinyl]methy1]-, (1S,5S)-", XP002717123, Database accession No. 1212647-76-1 the whole document.

Database Registry[Online] Chemical Abstracts Service, Columbus, Ohio, US; Nov. 4, 2008 (Nov. 4, 2008), "4-Quinazolinamine, 2-(4-azatricyclo[4.3.1.13,8]undec-4-ylmethyl)-N-(2-methoxyethyl)-8-methyl-" XP002717127, Database accession No. 1070679-15-0 the whole document.

Database Registry[Online] Chemical Abstracts Service, Columbus, Ohio, US; Nov. 4, 2008 (Nov. 4, 2008), "4-Quinazolinamine, 2-[-(3,4-dihydro-2(1H)-isoquinolinyl)methyl]-N-[(5-methyl-2-furanyl)methyl]-" XP002717128, Database accession No. 1070790-94-8 the whole document.

Database Registry[Online] Chemical Abstracts Service, Columbus, Ohio, US; Nov. 4, 2008 (Nov. 4, 2008), "4-Quinazolinamine, 2-[(3,4-dihydro-10-methoxy-2H-1,5-benzoxazocin-5(6H)-yl)methyl]-N-[(5-methyl-2-furanyl)methyl]-" XP002717129, Database accession No. 1070755-17-4 the whole document.

International Search Report Dated Dec. 20, 2013.

\* cited by examiner

RESPIRATORY SYNCYTIAL VIRUS INHIBITORS

This application is the National Phase Under 35 USC §371 of PCT International Application No. PCT/US2013/067276 filed on Oct. 29, 2013, the entire contents which are hereby incorporated by reference.

FIELD OF THE INVENTION

The present invention relates to quinazoline analogs and their use as inhibitors of replication of the respiratory syncytial virus (RSV), pharmaceutical compositions containing such analogs, and methods of using these analogs in the treatment and prevention of RSV infection.

BACKGROUND OF THE INVENTION

Globally, the annual death rate from RSV is estimated at more than 160,000 and the clinical burden of RSV infection is comparable to that of influenza (Bourgeois et al., 2009; Boyce et al., 2000; Hall et al., 2009; Stockman et al., 2012). The epidemic season for RSV runs from late fall through early spring. The primary populations at risk for poor outcome are children below 5 years of age, immunocompromised patients and older adults, particularly those who are institutionalized or have chronic underlying disease (Hall et al., 2009; Falsey et al., 2005). There is generally no available therapy for RSV infection, except for supportive care. Few drugs exist and fewer have been approved for therapeutic use (WO 2002/026228; WO 2002/062290; WO 2001/095910; WO 2012/080451). Inhaled ribavirin is approved for the treatment of laboratory-diagnosed RSV infection but is administered only to some bone marrow transplant and immunocompromised patients, because of its limited effectiveness, complexity of administration and mutagenicity potential for patients and staff. Because of the absence of effective therapy for RSV infections and the significance of RSV morbidity and/or morality in at-risk populations, the introduction of an effective RSV agent will be considered a major breakthrough in the care of these patients.

SUMMARY OF THE INVENTION

The present invention provides a novel series of compounds that exhibit inhibitory activity on the replication of the RSV.

Further objects of this invention arise for the one skilled in the art from the following description and the examples.

One aspect of the invention provides a compound, represented by Formula (I), or a racemate, enantiomer, diastereoisomer or tautomer thereof:

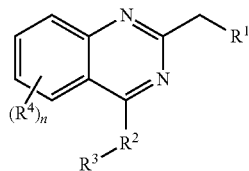

wherein $R^1$ is an 8-14 membered heterocycle or heteroaryl optionally substituted 1 to 4 times with substituents each independently selected from the group consisting of $R^{1A}$, oxo, halo, —CN, $(C_{1-6})$haloalkyl, OH, —O$(C_{1-6})$alkyl, —C(=O)OH and —C(=O)—O—$(C_{1-6})$alkyl;

$R^{1A}$ is $(C_{1-6})$alkyl, $(C_{3-7})$cycloalkyl, aryl, heteroaryl or heterocyclyl, wherein each said alkyl, cycloalkyl, aryl, heteroaryl and heterocyclyl are optionally mono-, di- or tri-substituted with substituents each independently selected from the group consisting of $(C_{1-6})$alkyl, $(C_{1-6})$haloalkyl, halo, —O$(C_{1-6})$alkyl, —CN, $NH_2$, —N(H)$R^{1B}$, —N(($C_{1-6}$)alkyl)$_2$, —C(=O)OH, —C(=O)—$R^{1B}$, —C(=O)—$(C_{1-6})$alkyl-N(($C_{1-6}$)alkyl)$_2$, —C(=O)—O—$R^{1B}$, —C(=O)—$NH_2$, —C(=O)—N(H)$R^{1B}$, —C(=O)—N(($C_{1-6}$)alkyl)$_2$, —SO$_2$$(C_{1-6})$haloalkyl or —SO$_2R^{1B}$;

$R^{1B}$ is $(C_{1-6})$alkyl, $(C_{3-7})$cycloalkyl, aryl, heteroaryl or heterocyclyl;

$R^2$ is $(C_{1-6})$alkyl, —O—, —S— or —N$R^{2A}$;

$R^{2A}$ is H or $(C_{1-6})$alkyl;

$R^3$ is $(C_{1-6})$alkyl, $(C_{3-7})$cycloalkyl, aryl, heteroaryl, heterocyclyl, —$(C_{1-6})$alkyl-$(C_{3-7})$cycloalkyl, —$(C_{1-6})$alkyl-aryl, —$(C_{1-6})$alkyl-heteroaryl or —$(C_{1-6})$alkyl-heterocyclyl, wherein each said alkyl, cycloalkyl, aryl, heteroaryl and heterocyclyl are optionally mono-, di- or tri-substituted with $R^{3A}$;

or wherein $R^{2A}$ and $R^3$ are linked together with the N to which they are attached to form a heterocycle optionally mono-, di- or tri-substituted with $R^{3A}$;

$R^{3A}$ is each independently selected from the group consisting of halo, oxo, —CN, OH, —COOH, —$(C_{1-6})$alkyl (optionally substituted with —OH), —O—$(C_{1-6})$alkyl, $(C_{3-7})$cycloalkyl, $(C_{1-6})$haloalkyl, —O—C(=O)—$R^{3B}$, —C(=O)—O—$R^{3B}$, —S—$(C_{1-6})$alkyl, —SO$_2NH_2$, —SO$_2$—N(H)$R^{3B}$, —SO$_2$—N(($C_{1-6}$)alkyl)$_2$, —SOR$^{3B}$, —SO$_2R^{3B}$, —C(=O)—$NH_2$, —C(=O)—N(H)$R^{3B}$, —C(=O)—N(($C_{1-6}$)alkyl)$_2$, —C(=O)—NH—SO$_2R^{3B}$, —SO$_2$—NH—C(=O)$R^{3B}$, —$NH_2$, —N(H)$R^{3B}$, —N(($C_{1-6}$)alkyl)$_2$, —NH—C(=O)$R^{3B}$, —NH—C(=O)O—$R^{3B}$, —C(=O)—$R^{3B}$, and $R^{3B}$ (optionally substituted with $(C_{1-6})$alkyl);

$R^{3B}$ is $(C_{1-6})$alkyl, $(C_{3-7})$cycloalkyl, aryl, heteroaryl or heterocyclyl;

$R^4$ is each independently selected from the group consisting of H, halo, —CN, OH, —COOH, —$(C_{1-6})$alkyl, —O—$(C_{1-6})$alkyl, $(C_{3-7})$cycloalkyl, $(C_{1-6})$haloalkyl, —C(=O)—O—$(C_{1-6})$alkyl, —SO$_2NH_2$, —SO$_2$—NH$(C_{1-6})$alkyl, —SO$_2$—N(($C_{1-6}$)alkyl)$_2$, —SO$(C_{1-6})$alkyl, —SO$_2$($C_{1-6}$)alkyl, —C(=O)—$NH_2$, —C(=O)—NH$(C_{1-6})$alkyl, —C(=O)—N(($C_{1-6}$)alkyl)$_2$, —C(=O)—NH—SO$_2$($C_{1-6}$)alkyl, —SO$_2$—NH—C(=O)—$(C_{1-6})$alkyl, —$NH_2$, —NH$(C_{1-6})$alkyl, —N(($C_{1-6}$)alkyl)$_2$, —NH($C_{3-7}$)cycloalkyl, —N(($C_{1-6}$)alkyl)($C_{3-7}$)cycloalkyl, —NH—C(=O)($C_{1-6}$)alkyl, —NH—C(=O)O($C_{1-6}$)alkyl and $R^{4a}$;

$R^{4a}$ is —$(C_{1-6})$alkyl-heterocyclyl, —$(C_{1-6})$alkyl-heteroaryl, heterocyclyl or heteroaryl, wherein each said heterocyclyl and heteroaryl is optionally mono-, di- or tri-substituted with $(C_{1-6})$alkyl;

n is 0, 1, 2 or 3 or a salt thereof.

Another aspect of this invention provides a compound of Formula (I), or a pharmaceutically acceptable salt thereof, as a medicament.

Also within the scope of this invention is the use of a compound of Formula (I), or a pharmaceutically acceptable salt thereof, for the manufacture of a medicament for the treatment or prevention of RSV infection in a human being.

Included within the scope of this invention is a pharmaceutical composition comprising a compound of Formula (I), or a pharmaceutically acceptable salt thereof, and a pharmaceutically acceptable carrier.

According to a further aspect of this embodiment the pharmaceutical composition according to this invention further comprises a therapeutically effective amount of at least one other antiviral agent.

The invention also provides the use of a pharmaceutical composition as described hereinabove for the treatment of an RSV infection in a human being having or at risk of having the infection. Another aspect of the invention involves a method of treating or preventing RSV infection in a human being by administering to the human being an anti-RSV virally effective amount of a compound of the invention, a pharmaceutically acceptable salt thereof, or a composition as described above, alone or in combination with at least one other antiviral agent, administered together or separately.

An additional aspect of this invention refers to an article of manufacture comprising a composition effective to treat RSV infection; and packaging material comprising a label which indicates that the composition can be used to treat infection by RSV; wherein the composition comprises a compound of Formula (I) according to this invention or a pharmaceutically acceptable salt thereof.

Still another aspect of this invention relates to a method of inhibiting the replication of RSV comprising exposing the virus to an effective amount of the compound of Formula (I), or a salt thereof, under conditions where replication of RSV is inhibited.

Further included in the scope of the invention is the use of a compound of Formula (I), or a salt thereof, to inhibit the replication of RSV.

DETAILED DESCRIPTION OF PREFERRED EMBODIMENTS

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the first named subgroup is the radical attachment point, for example, the substituent "—$C_{1-3}$-alkyl-aryl" means an aryl group which is bound to a $C_{1-3}$-alkyl-group, with the $C_{1-3}$-alkyl group bound to the core. Unless specifically stated otherwise, for groups comprising two or more subgroups, the substituent may be attached to either subgroup.

In case a compound of the present invention is depicted in the form of a chemical name and as a formula in case of any discrepancy the formula shall prevail. An asterisk or the designation, ----, may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers, atropisomers) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

One skilled in the art would know how to separate, enrich, or selectively prepare the enantiomers of the compounds of the present invention. Preparation of pure stereoisomers, e.g. enantiomers and diastereomers, or mixtures of desired enantiomeric excess (ee) or enantiomeric purity, are accomplished by one or more of the many methods of (a) separation or resolution of enantiomers, or (b) enantioselective synthesis known to those of skill in the art, or a combination thereof. These resolution methods generally rely on chiral recognition and include but not limited to chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in Chiral Separation Techniques: A Practical Approach (2nd Ed.), G. Subramanian (ed.), Wiley-VCH, 2000; T. E. Beesley and R. P. W. Scott, Chiral Chromatography, John Wiley & Sons, 1999; and Satinder Ahuja, Chiral Separations by Chromatography, Am. Chem. Soc., 2000. Furthermore, there are equally well-known methods for the quantitation of enantiomeric excess or purity, including but not limited to GC, HPLC, CE, or NMR, and assignment of absolute configuration and conformation, including but not limited to CD, ORD, X-ray crystallography, or NMR.

The term "halo" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-3}$-alkyl embraces the radicals $H_3C$—, $H_3C$—$CH_2$—, $H_3C$—$CH_2$—$CH_2$— and $H_3C$—$CH(CH_3)$—.

The term "carbocyclyl" or "carbocycle" as used herein, either alone or in combination with another radical, means a mono-, bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

The term "$C_{3-n}$-cycloalkyl", wherein n is an integer 4 to n, either alone or in combination with another radical, denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "aryl" as used herein, either alone or in combination with another radical, denotes a carbocyclic aromatic monocyclic group containing 6 carbon atoms which may be further fused to at least one other 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring system including aromatic ring systems containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms. The "heterocyclyl" may be optionally substituted with substituents, such as, for example, with an oxo moiety. Thus, the term "heterocyclyl" or "heterocyclyl" includes the following exemplary structures which are not depicted as radicals as each form may be attached through a covalent bond to any atom so long as appropriate valences are maintained:

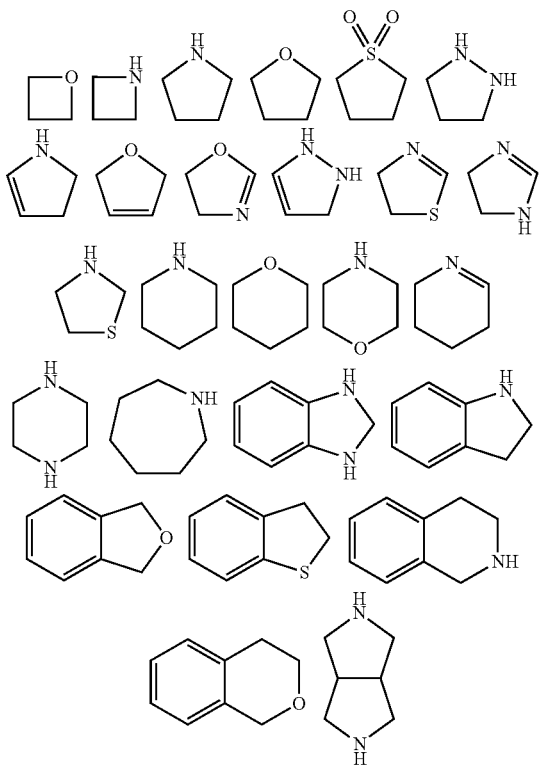

Thus, a "heterocyclyl" substituted with an oxo moiety includes the following exemplary structures which are not depicted as radicals as each form may be attached through a covalent bond to any atom so long as appropriate valences are maintained:

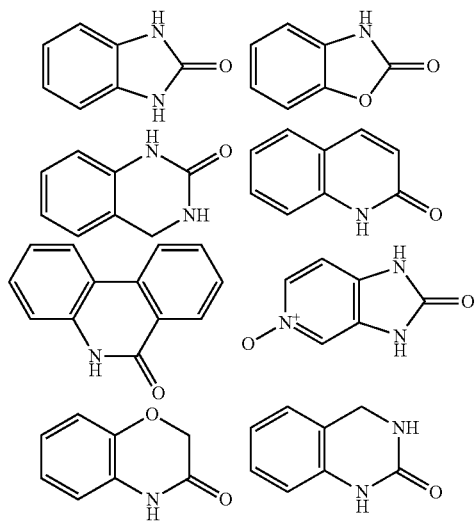

The term "heteroaryl" means a mono- or polycyclic-ring system containing one or more heteroatoms selected from N, O or S(O)$_r$, wherein r=0, 1 or 2, consisting of 5 to 14 ring atoms wherein at least one of the heteroatoms is part of an aromatic ring. The term "heteroaryl" is intended to include all the possible isomeric forms. The "heteroaryl" may be optionally substituted with substituents, such as, for example, with an oxo moiety. Thus, the term "heteroaryl" includes the following exemplary structures which are not depicted as radicals as each form may be attached through a covalent bond to any atom so long as appropriate valences are maintained:

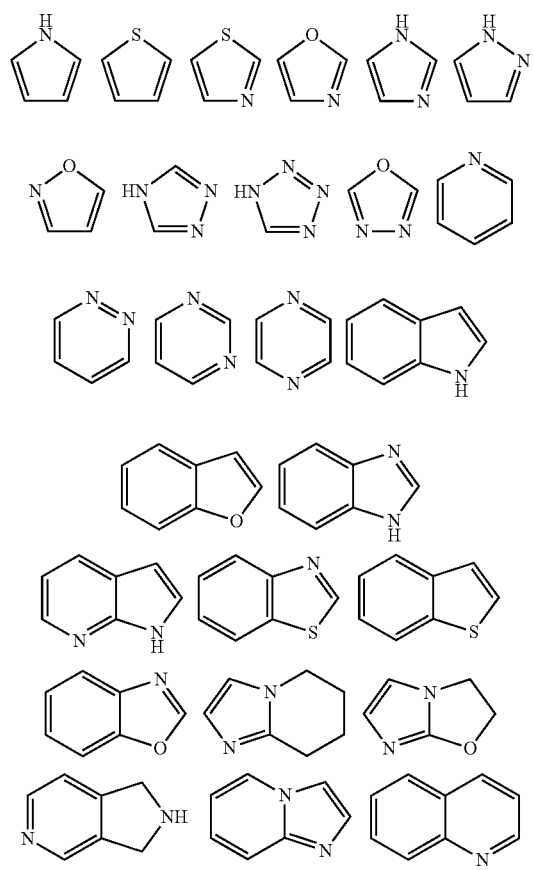

Thus, a "heteroaryl" substituted with an oxo moiety includes the following exemplary structures which are not depicted as radicals as each form may be attached through a covalent bond to any atom so long as appropriate valences are maintained:

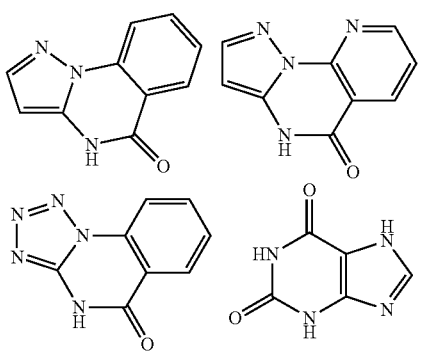

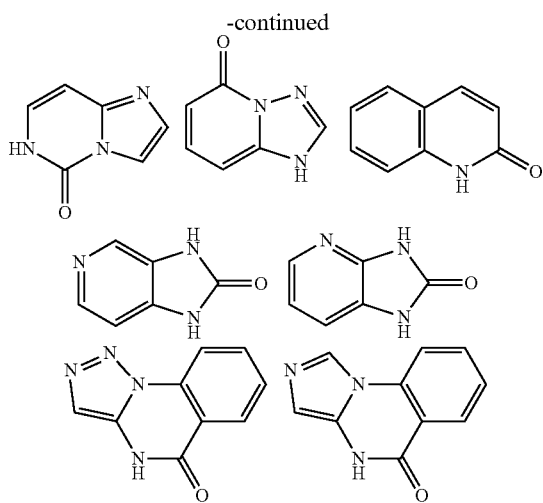

Many of the terms given above may be used repeatedly in the definition of a formula or group and in each case have one of the meanings given above, independently of one another. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention also comprise a part of the invention.

As used herein, the term "treatment" means the administration of a compound or composition according to the present invention to alleviate or eliminate symptoms of RSV disease and/or to reduce viral load in a patient.

As used herein, the term "prevention" means the administration of a compound or composition according to the present invention post-exposure of the individual to the virus but before the appearance of symptoms of the disease, and/or prior to the detection of the virus, to prevent the appearance of symptoms of the disease.

The term "therapeutically effective amount" means an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

Further Embodiments

In the following embodiments, groups and substituents of the compounds of Formula (I) according to this invention are described in detail.

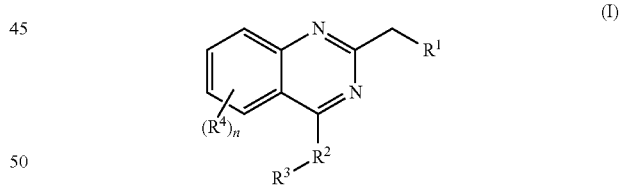

(I)

Any and each of the definitions below may be combined with each other.

$R^1$:

$R^1$-A: $R^1$ is an 8-14 membered heterocycle or heteroaryl optionally substituted 1 to 4 times with substituents each independently selected from the group consisting of $R^{1A}$, oxo, halo, —CN, $(C_{1-6})$haloalkyl, OH, —O$(C_{1-6})$alkyl, —C(=O)OH and —C(=O)—O—$(C_{1-6})$alkyl;

$R^{1A}$ is $(C_{1-6})$alkyl, $(C_{3-7})$cycloalkyl, aryl, heteroaryl or heterocyclyl, wherein each said alkyl, cycloalkyl, aryl, heteroaryl and heterocyclyl are optionally mono-, di- or tri-substituted with substituents each independently selected from the group consisting of $(C_{1-6})$alkyl, $(C_{1-6})$haloalkyl, halo, —O$(C_{1-6})$alkyl, —CN, $NH_2$, —N(H)$R^{1B}$, —N(($C_{1-6}$)alkyl)$_2$, —C(=O)OH, —C(=O)—$R^{1B}$, —C(=O)—$(C_{1-6})$ alkyl-N((C$_{1-6}$)alkyl)$_2$, —C(=O)—O—R$^{1B}$, —C(=O)—NH$_2$, —C(=O)—N(H)R$^{1B}$, —C(=O)—N((C$_{1-6}$)alkyl)$_2$, —SO$_2$(C$_{1-6}$)haloalkyl or —SO$_2$R$^{1B}$;

R$^{1B}$ is (C$_{1-6}$)alkyl, (C$_{3-7}$)cycloalkyl, aryl, heteroaryl or heterocyclyl.

R$^1$—B: R$^1$ is a 9 to 14 heterocycle or heteroaryl optionally substituted mono- or di-substituted with oxo, (C$_{1-6}$)alkyl, halo, —CN, (C$_{1-6}$)haloalkyl, OH, —O(C$_{1-6}$)alkyl, —C(=O)OH, —C(=O)—O—(C$_{1-6}$)alkyl, (C$_{3-7}$)cycloalkyl.

R$^1$—C: R$^1$ is a 9 to 14 heterocycle or heteroaryl selected from the group consisting of

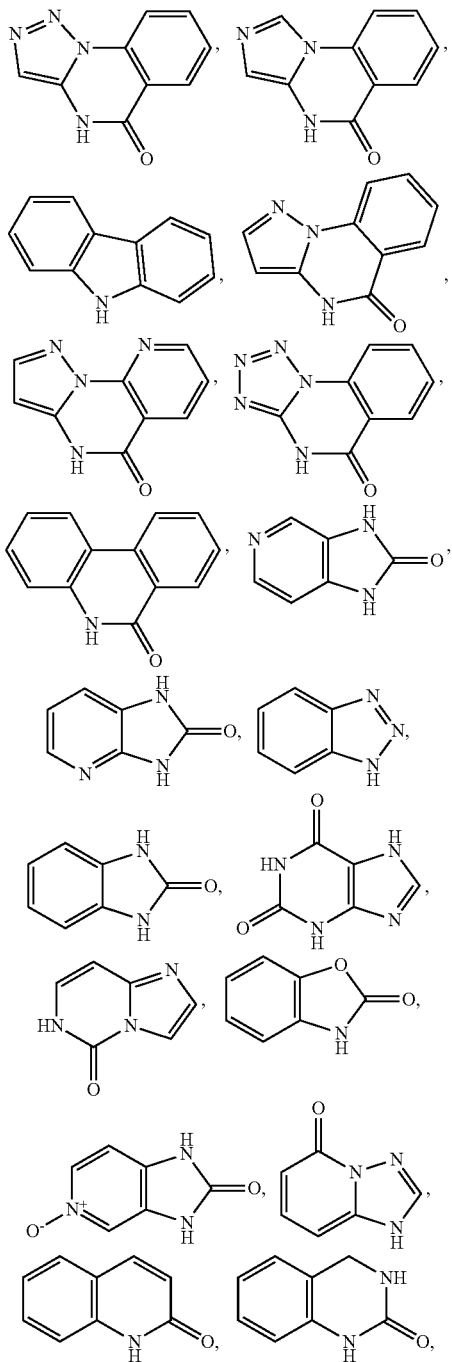

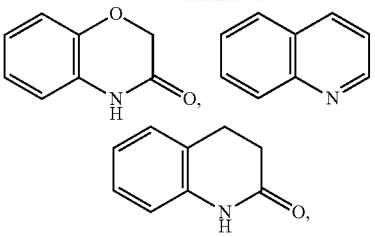

wherein said heteroaryl and heterocyclyl are optionally mono- or di-substituted with (C$_{1-6}$)alkyl, halo, —CN, (C$_{1-6}$)haloalkyl, OH, —O(C$_{1-6}$)alkyl, —C(=O)OH, —C(=O)—O—(C$_{1-6}$)alkyl or (C$_{3-7}$)cycloalkyl.

R$^2$/R$^3$:

R$^2$/R$^3$-A: R$^2$ is (C$_{1-6}$)alkyl, —O—, —S— or —NR$^{2A}$;

R$^{2A}$ is H or (C$_{1-6}$)alkyl;

R$^3$ is (C$_{1-6}$)alkyl, (C$_{3-7}$)cycloalkyl, aryl, heteroaryl, heterocyclyl, —(C$_{1-6}$)alkyl-(C$_{3-7}$)cycloalkyl, —(C$_{1-6}$)alkyl-aryl, —(C$_{1-6}$)alkyl-heteroaryl or —(C$_{1-6}$)alkyl-heterocyclyl, wherein each said alkyl, cycloalkyl, aryl, heteroaryl and heterocyclyl are optionally mono-, di- or tri-substituted with R$^{3A}$; or wherein R$^{2A}$ and R$^3$ are linked together with the N to which they are attached to form a heterocycle optionally mono-, di- or tri-substituted with R$^{3A}$;

R$^{3A}$ is each independently selected from the group consisting of halo, oxo, —CN, OH, —COOH, —(C$_{1-6}$)alkyl (optionally substituted with —OH), —O—(C$_{1-6}$)alkyl, (C$_{3-7}$)cycloalkyl, (C$_{1-6}$)haloalkyl, —O—C(=O)—R$^{3B}$, —C(=O)—O—R$^{3B}$, —S—(C$_{1-6}$)alkyl, —SO$_2$NH$_2$, —SO$_2$—N(H)R$^{3B}$, —SO$_2$—N((C$_{1-6}$)alkyl)$_2$, —SOR$^{3B}$, —SO$_2$R$^{3B}$, —C(=O)—NH$_2$, —C(=O)—N(H)R$^{3B}$, —C(=O)—N((C$_{1-6}$)alkyl)$_2$, —C(=O)—NH—SO$_2$R$^{3B}$, —SO$_2$—NH—C(=O)R$^{3B}$, —NH$_2$, —N(H)R$^{3B}$, —N((C$_{1-6}$)alkyl)$_2$, —NH—C(=O)R$^{3B}$, —NH—C(=O)O—R$^{3B}$, —C(=O)—R$^{3B}$ and R$^{3B}$ (optionally substituted with (C$_{1-6}$)alkyl);

R$^{3B}$ is (C$_{1-6}$)alkyl, (C$_{3-7}$)cycloalkyl, aryl, heteroaryl or heterocyclyl.

R$^2$/R$^3$—B: R$^2$ is (C$_{1-6}$)alkyl, —O— or —NR$^{2A}$;

R$^{2A}$ is H or (C$_{1-6}$)alkyl;

R$^3$ is aryl, heteroaryl, heterocyclyl, —(C$_{1-6}$)alkyl-(C$_{3-7}$)cycloalkyl, —(C$_{1-6}$)alkyl-aryl, —(C$_{1-6}$)alkyl-heteroaryl or —(C$_{1-6}$)alkyl-heterocyclyl, wherein each said cycloalkyl, aryl, heteroaryl and heterocyclyl are optionally mono-, di- or tri-substituted with R$^{3A}$;

R$^{3A}$ is each independently selected from the group consisting of halo, oxo, —CN, OH, —COOH, —(C$_{1-6}$)alkyl (optionally substituted with —OH), —O—(C$_{1-6}$)alkyl, (C$_{3-7}$)cycloalkyl, (C$_{1-6}$)haloalkyl, —O—C(=O)—(C$_{1-6}$)alkyl, —C(=O)—O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO(C$_{1-6}$)alkyl, —SO$_2$(C$_{1-6}$)alkyl, —C(=O)—NH$_2$, —C(=O)—NH(C$_{1-6}$)alkyl, —C(=O)—N((C$_{1-6}$)alkyl)$_2$, —C(=O)—NH—SO$_2$(C$_{1-6}$)alkyl, —SO$_2$—NH—C(=O)—(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl, —NH—C(=O)O(C$_{1-6}$)alkyl, heterocyclyl (optionally substituted with (C$_{1-6}$)alkyl) and heteroaryl (optionally substituted with (C$_{1-6}$)alkyl.

R$^2$/R$^3$—C: R$^2$ is —O— or —NR$^{2A}$;

R$^{2A}$ is H or (C$_{1-6}$)alkyl;

R$^3$ is heteroaryl, heterocyclyl, —(C$_{1-6}$)alkyl-heteroaryl or —(C$_{1-6}$)alkyl-heterocyclyl, wherein each said heteroaryl and heterocyclyl are optionally mono, di- or tri-substituted with R$^{3A}$;

$R^{3A}$ is each independently selected from the group consisting of halo, -oxo, —CN, OH, —COOH, —$(C_{1-6})$alkyl, —O$(C_{1-6})$alkyl, $(C_{3-7})$cycloalkyl, $(C_{1-6})$haloalkyl, —O—C(=O)—$(C_{1-6})$alkyl, —C(=O)—O—$(C_{1-6})$alkyl, —SO$_2$NH$_2$, —SO$_2$—NH$(C_{1-6})$alkyl, —SO$_2$—N$((C_{1-6})$alkyl$)_2$, —SO$(C_{1-6})$alkyl, —SO$_2(C_{1-6})$alkyl, —C(=O)—NH$_2$, —O(=O)—NH$(C_{1-6})$alkyl, —O(=O)—N$((C_{1-6})$alkyl$)_2$, —O(=O)—NH—SO$_2(C_{1-6})$alkyl, —SO$_2$—NH—C(=O)—$(C_{1-6})$alkyl, —NH$_2$, —NH$(C_{1-6})$alkyl, —N$((C_{1-6})$alkyl$)_2$, —NH—C(=O)$(C_{1-6})$alkyl, —NH—C(=O)O $(C_{1-6})$alkyl, heterocyclyl (optionally substituted with $(C_{1-6})$ alkyl) and heteroaryl (optionally substituted with $(C_{1-6})$) alkyl.

$R^4$:

$R^4$-A: $R^4$ is each independently selected from the group consisting of H, halo, —CN, OH, —COOH, —$(C_{1-6})$alkyl, —O—$(C_{1-6})$alkyl, $(C_{3-7})$cycloalkyl, $(C_{1-6})$haloalkyl, —O(=O)—O—$(C_{1-6})$alkyl, —SO$_2$NH$_2$, —SO$_2$—NH $(C_{1-6})$alkyl, —SO$_2$—N$((C_{1-6})$alkyl$)_2$, —SO$(C_{1-6})$alkyl, —SO$_2(C_{1-6})$alkyl, —O(=O)—NH$_2$, —O(=O)—NH$(C_{1-6})$ alkyl, —O(=O)—N$((C_{1-6})$alkyl$)_2$, —O(=O)—NH—SO$_2$ $(C_{1-6})$alkyl, —SO$_2$—NH—C(=O)—$(C_{1-6})$alkyl, —NH$_2$, —NH$(C_{1-6})$alkyl, —N$((C_{1-6})$alkyl$)_2$, —NH$(C_{3-7})$cycloalkyl, —N$((C_{1-6})$alkyl$)(C_{3-7})$cycloalkyl, —NH—C(=O) $(C_{1-6})$alkyl, —NH—C(=O)O$(C_{1-6})$alkyl and $R^{4a}$;

$R^{4a}$ is —$(C_{1-6})$alkyl-heterocyclyl, —$(C_{1-6})$alkyl-heteroaryl, heterocyclyl or heteroaryl, wherein each said heterocyclyl and heteroaryl is optionally mono-, di- or tri-substituted with $(C_{1-6})$alkyl.

$R^4$—B: $R^4$ is each independently selected from the group consisting of H, halo, —CN, OH, —$(C_{1-6})$alkyl, —O— $(C_{1-6})$alkyl, $(C_{3-7})$cycloalkyl, $(C_{1-6})$haloalkyl and $R^{4a}$;

$R^{4a}$ is heterocyclyl or heteroaryl, wherein each said heterocyclyl and heteroaryl is optionally mono-, di- or tri-substituted with $(C_{1-6})$alkyl.

$R^4$—C: $R^4$ is each independently selected from the group consisting of H, halo, —CN, OH, —$(C_{1-6})$alkyl, —O— $(C_{1-6})$alkyl, $(C_{3-7})$cycloalkyl and $(C_{1-6})$haloalkyl.

n:

n-A: n is 0, 1, 2 or 3.

n-B: n is 0 or 1.

n-C: n is 0.

Examples of preferred subgeneric embodiments of the present invention are set forth in the following table, wherein each substituent group of each embodiment is defined according to the definitions set forth above:

| Embodiment | $R^1$ | $R^2/R^3$ | $R^4$ | n |
|---|---|---|---|---|
| E-1 | $R^1$-C | $R^2/R^3$-C | $R^4$-C | n-C |
| E-2 | $R^1$-B | $R^2/R^3$-B | $R^4$-B | n-B |
| E-3 | $R^1$-A | $R^2/R^3$-B | $R^4$-B | n-A |
| E-4 | $R^1$-C | $R^2/R^3$-B | $R^4$-B | n-A |
| E-5 | $R^1$-B | $R^2/R^3$-A | $R^4$-B | n-B |

Examples of most preferred compounds according to this invention are each single compound of the invention, namely, compounds 1001, 1002, 1003, 1004, 1005, 1006, 1007, 1008, 1009, 1010, 1011, 1012, 1013, 1014, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 112 7, 1128, 1129, 1130, 1131, 1132, 1133, 1134, 1135, 1138, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221 and 1222.

Pharmaceutical Composition

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders, etc.

The content of the pharmaceutically active compound(s) should be in the range from 0.05 to 90 wt.-%, preferably 0.1 to 50 wt.-% of the composition as a whole.

Suitable tablets may be obtained, for example, by mixing one or more compounds of the invention with known excipients, for example inert diluents, carriers, binders, disintegrants, adjuvants, surfactants and/or lubricants. The tablets may also consist of several layers.

Suitable inhalatives may be obtained, for example, by administering one or more compounds of the invention in the form of a solution, dry powder or suspension. The compounds of the invention may be administered via inhalation of a solution in nebulized or aerosolized doses.

The dose range of the compounds of the invention applicable per day is usually from 0.01 to 100 mg/kg of body weight, preferably from 0.1 to 50 mg/kg of body weight. Each dosage unit may conveniently contain from 5% to 95% active compound (w/w). Preferably such preparations contain from 20% to 80% active compound.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Combination Therapy

When the composition of this invention comprises a combination of a compound of the invention and one or more additional therapeutic or prophylactic agent, both the compound and the additional agent should be present at dosage levels of between about 10 to 100%, and more preferably between about 10 and 80% of the dosage normally administered in a monotherapy regimen. Therefore, according to one embodiment, the pharmaceutical composition of this invention additionally comprises one or more antiviral agents.

Antiviral agents contemplated for use in such combination therapy include agents (compounds or biologicals) that are effective to inhibit the production and/or replication of a virus in a human being, including but not limited to agents that interfere with either host or viral mechanisms necessary for the production and/or replication of a virus in a human being. Such agents can be selected from: RSV Fusion inhibitors, such as MDT-637 (MicroDose), BTA-9881 (Biota); RSV Polymerase inhibitors, such as ALS-8112 (Alios), ALS-8176 (Alios) and Virazole (ribavirin); others, such as GS-5806 (Gilead Sciences) and RSV-604 (Novartis); antibodies, such as Synagis® (palimizumab), RespiGam® (RSV-IG), MEDI-557 (MedImmune/AstraZeneca), ALX-0171 (Ablynx), motavizumab (MedImmune/AstraZeneca); other biological, such as ALN-RSV-01 (Alnylam) and Vaccines, such as MEDI-559 (MedImmune/AstraZeneca), RSV F (Novavax), MEDI-534 (MedImmune/AstraZeneca).

EXAMPLES

Other features of the present invention will become apparent from the following non-limiting examples which illustrate the principles of the invention. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. The reactants used in the examples below may be obtained either as described herein, or if not described herein, are themselves either commercially available or may be prepared from commercially available materials by methods known in the art.

All of the compounds of the invention are synthesized analogously to the Examples. It will be apparent to a skilled person that the analogous synthetic routes may be used, with appropriate modifications, to prepare the compounds of the invention as described herein.

Compounds and intermediates can be purified by a Teledyne ISCO Combiflash $R_f$ System at 254 nm using commercial normal phase silica 4-120 g Redisep $R_f$ or Silicycle columns at a flow rate of 18-85 mL/min depending on column size. Mass spectral analyses may be recorded using flow injection analysis mass spectrometry or Waters Acquity Ultraperformance LC System consisting of a sample organizer, PDA detector, column manager, sample manager, binary solvent manager and SQ detector.

Reactions performed in microwave conditions are conducted in a Biotage Initiator 2.0 microwave synthesizer equipped with a Robot Sixty for vial manipulations. The temperature range is from 40-250° C. The pressure range is from 0-20 bar and the power range is from 0-400 Watts at 2.45 GHz. The vial size varies from 0.5 mL to 20 mL. The solvent absorption level is high by default. Specific reaction times and temperatures are given in the experimental section when applicable.

Preparative HPLC-MS is performed using a Waters instrument, using one of the conditions outlined below:

Sunfire Prep 018 column, OBD, 5 µm, 30×75 mm, 120 Å, elution with a gradient of ACN/H₂O containing 0.06% TFA, 60 mL/min.

Sunfire Prep 018 column, OBD, 5 µm, 19×50 mm, 120 Å, elution with a gradient of ACN/H₂O containing 0.06% TFA, 30 mL/min.

Sunfire Prep 018 column, OBD, 5 µm, 19×50 mm, 120 Å at RT or 45° C., elution with a gradient of MeOH or ACN/Ammonium formate 10 mM in H₂O, pH 3.8, 30 mL/min or 45 mL/min.

X-Bridge Prep 018 column, OBD, 5 µm, 19×50 mm, 120 Å at RT, elution with a gradient of MeOH/Ammonium bicarbonate 10 mM in H₂O, pH 10, 30 mL/min.

SFC-MS is performed using a Waters Prep-100 instrument, using one of the conditions outlined below:

2-Ethylpyridine column, 30×150 mm, elution with either CO₂/MeOH or CO₂/iPrOH, 100 mL/min.

Analytical HPLC and UPLC-MS are carried out under standard conditions using one of four columns (Sunfire C18, CombiScreen ODS-AQ, HSS 018 or BEH C18) with the specific conditions shown below:

Column: Sunfire C18, 3.5 µm, 4.6×30 mm

Eluent A: H₂O+0.06% or 0.1% TFA

Eluent B: ACN+0.06% or 0.1% TFA

Gradient: Linear 2% B for 0.6 min, 2% to 50% B in 4.9 min, 50% to 100% B in 1.8 min, isocratic at 100% B for 0.6 min Column: CombiScreen ODS-AQ, S-5 µm, 12 nm, 4.6×50 mm Eluent A: H₂O+0.1% TFA Eluent B: ACN+0.1% TFA Gradient: Linear 5% B for 0.5 min, 5% to 50% B in 5.5 min, 50% to 100% B in 4.5 min, isocratic at 100% B for 1.0 min Column: HSS C18, 1.8 µm, 2.1×30 mm at 25° C. or 45° C.

Eluent A: Ammonium formate 10 mM in H₂O, pH 3.8

Eluent B: MeOH or ACN

Gradient: 5% to 100% B in 2.3 min, isocratic at 100% B for 0.7 min

Column: HSS C18, 1.8 µm, 2.1×30 mm

Eluent A: H₂O+0.06% TFA

Eluent B: ACN

Gradient: 5% to 100% B in 2.2 min, isocratic at 100% B for 0.8 min

Column: BEH C18, 1.7 µm, 2.1×30 mm at 25° C. or 45° C.

Eluent A: Ammonium bicarbonate 10 mM in H₂O, pH 10.0

Eluent B: MeOH or ACN

Gradient: 5% to 100% B in 2.2 min, isocratic at 100% B for 0.8 min

Abbreviations Used in the Examples Include:

ACN: acetonitrile; AcOH: acetic acid; AmFor: Ammonium Formate aqueous solution; AmBicar: Ammonium Bicarbonate aqueous solution; BEH: ethylene bridged hybrid; CDI: 1,1'-carbonyl diimidazole; DCM: dichloromethane; DIPEA: diisopropylethylamine; DMA; N,N-dimethyl-acetamide; DMF: N,N-dimethylformamide; DMSO: dimethylsulfoxide; DMEM: Dulbecco's modified Eagle's medium; dppf: 1,1'-diphenylphosphinylferrocene; $EC_{50}$: 50% effective concentration; Et: ethyl; EtOAc: ethyl acetate; EtOH: ethanol; Et₂O: ethyl ether; h: hour; HPLC: high performance liquid chromatography; HSS: high strength silica; $[M+H]^+$: protonated molecular ion; m-CPBA: meta-chloroperoxybenzoic acid; MOI: Multiplicity of Infection; MS: mass spectrometry; OBD: optimum bed density; Me: methyl; MeOH: methanol; PCC: Pyridinium chlorochromate; PSI: pounds per square inch; RT: room temperature (18 to 22° C.); RP-HPLC: reverse phase-high pressure liquid chromatography; TEA: triethylamine; TFA: trifluoroacetic acid; THF: tetrahydrofuran; sat: saturated; SFC: supercritical fluid chromatography; $t_R$: retention time; Ph: phenyl; Ph₃P: triphenylphosphine; DIAD: diisopropyl azodicarboxylate; MS: mass; iPrOH: isopropanol; Et₃N: triethylamine; EtONa: sodium ethoxide; min: minute; M: molar; W: Watt; PPA: polyphosphoric acid; conc: concentrated; UPLC-MS: ultra performance liquid chromatography mass spectrometry General Scheme

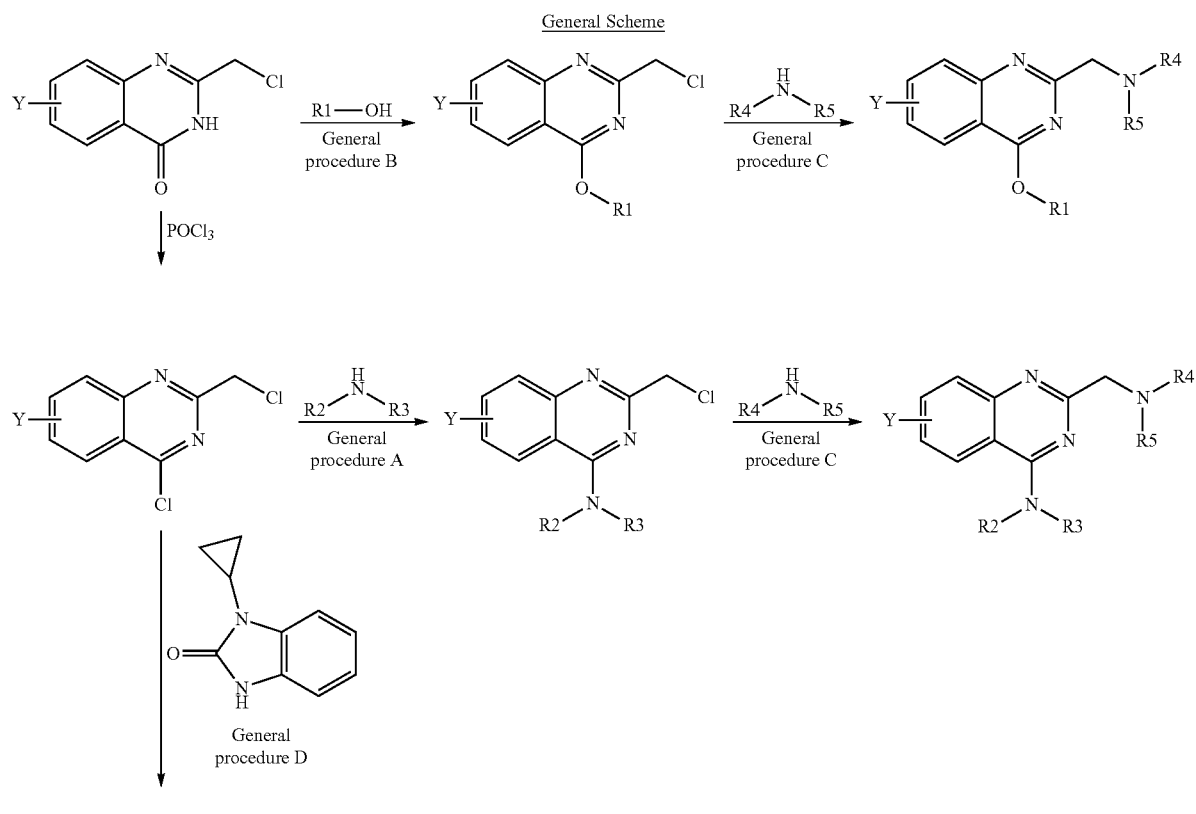

Example 1

(General Procedure A): Preparation of Intermediate 1a3

Nucleophilic Substitution

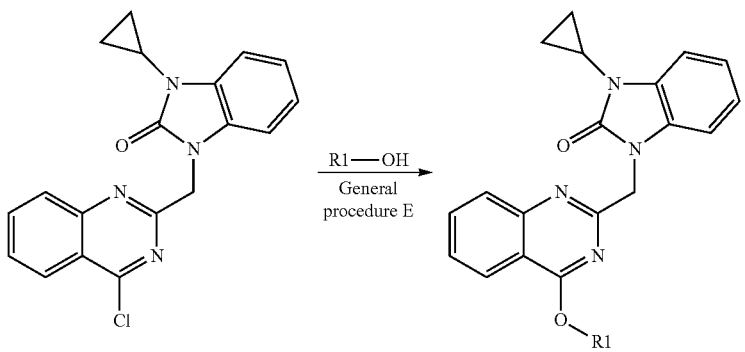

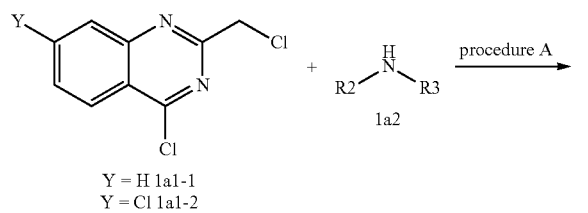

-continued

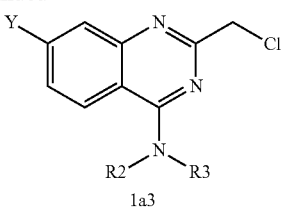

To a solution of the reagent 1a1 (1a1-1 from Syntech, 1a1-2 synthesized in example 22) (eg 1 equivalent) in a solvent, such as isopropanol, is added the amine 1a2 (1 equivalent) in a solvent such as isopropanol, then a base, such as triethylamine (2 equivalents) or DIPEA (2.2 equivalents) is added. If necessary some additional 1a2 is added (up to 0.2 additional equivalents). The mixture is stirred at RT for a period varying from 2 h to 4 days (eg 20 h). The product is
- either filtered off the reaction mixture
- or dissolved in 1-butanol and then dried with MgSO$_4$, filtered and evaporated.
- or the solvent is concentrated under reduced pressure. In the case of solvent evaporation, either the residue obtained is used directly in the next step or a work-up is done. A typical work up can be performed in the following way: water or a saturated aqueous solution of NaHCO$_3$ is added, then the mixture is extracted with EtOAc (twice) or DCM. The combined organic layers are washed with brine, then dried with MgSO$_4$, filtered and evaporated to afford compound 1a3 which is either used as such in the next step or purified by flash chromatography on silica using either ACN and DCM or EtOAc as eluents or purified by mass directed purification using a C18 Sun Fire column and a gradient of ACN and AmFor or purified by SFC-MS using a "2-ethylpyridine" column and a mixture of CO$_2$ and MeOH as eluent.

Using reagent 1a1-1

| Amine used | no | source | Intermediate obtained | no |
|---|---|---|---|---|
| 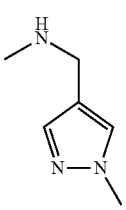 | 1a2-1 | Chembridge | 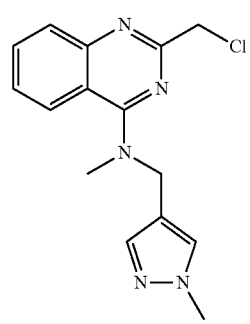 [SMILES: CN(Cc1cnn(C)c1)c1nc(CCl)nc2ccccc12] | 1a3-1 |
| 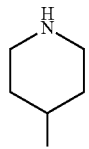 | 1a2-2 | Aldrich | 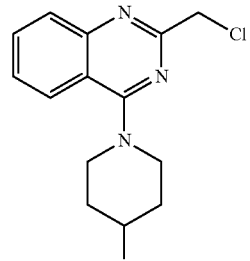 | 1a3-2 |
| 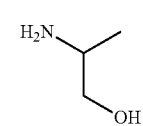 | 1a2-3 | Aldrich | 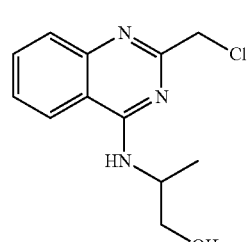 | 1a3-3 |
| 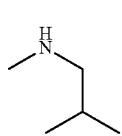 | 1a2-4 | Pfaltz-Bauer | 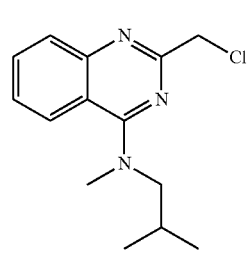 [SMILES: CC(C)CN(C)c1nc(CCl)nc2ccccc12] | 1a3-4 |

-continued

| Amine used | no | source | Intermediate obtained | no |
|---|---|---|---|---|
| H₂N~~~OH (3-aminopropan-1-ol) | 1a2-5 | Aldrich | 2-(chloromethyl)-N-(3-hydroxypropyl)quinazolin-4-amine | 1a3-5 |
| MeHN~~~OH (3-(methylamino)propan-1-ol) | 1a2-6 | TCI | 2-(chloromethyl)-N-(3-hydroxypropyl)-N-methylquinazolin-4-amine | 1a3-6 |
| MeHN-CH₂-(tetrahydrofuran-3-yl) | 1a2-7 | Maybridge | 2-(chloromethyl)-N-methyl-N-((tetrahydrofuran-3-yl)methyl)quinazolin-4-amine | 1a3-7 |
| H₂N-CH₂-(tetrahydrofuran-3-yl) | 1a2-8 | Combi-Blocks | 2-(chloromethyl)-N-((tetrahydrofuran-3-yl)methyl)quinazolin-4-amine | 1a3-8 |
| H₂N-CH₂-CN (aminoacetonitrile) | 1a2-9 | Aldrich | 2-((2-(chloromethyl)quinazolin-4-yl)amino)acetonitrile | 1a3-9 |

-continued

| Amine used | no | source | Intermediate obtained | no |
|---|---|---|---|---|
| (1-methyl-1H-pyrazol-4-yl)methanamine | 1a2-10 | Maybridge | quinazoline intermediate with (1-methyl-1H-pyrazol-4-yl)methylamino substituent | 1a3-10 |
| N-methyl-1-(pyridin-3-yl)methanamine | 1a2-11 | Aldrich | quinazoline intermediate with N-methyl-N-(pyridin-3-ylmethyl)amino substituent | 1a3-11 |
| N-methyl-1-(1H-tetrazol-5-yl)methanamine | 1a2-12 | Enamine-BB | quinazoline intermediate with N-methyl-N-(1H-tetrazol-5-ylmethyl)amino substituent | 1a3-12 |
| 2-amino-N-methylacetamide | 1a2-13 | Chembridge-BB | quinazoline intermediate with N-methylacetamide linker | 1a3-13 |
| N-methyl-2-morpholinoethanamine | 1a2-14 | Enamine | quinazoline intermediate with N-methyl-2-morpholinoethylamino substituent | 1a3-14 |

-continued

| Amine used | no | source | Intermediate obtained | no |
|---|---|---|---|---|
| 1-(1-methyl-1H-pyrazol-4-yl)ethan-1-amine | 1a2-15 | Enamine | 2-(chloromethyl)-N-[1-(1-methyl-1H-pyrazol-4-yl)ethyl]quinazolin-4-amine | 1a3-15 |
| 3-(1-methyl-1H-pyrazol-4-yl)pyrrolidine | 1a2-16 | Enamine | 2-(chloromethyl)-4-[3-(1-methyl-1H-pyrazol-4-yl)pyrrolidin-1-yl]quinazoline | 1a3-16 |
| 5-methyloctahydropyrrolo[3,4-c]pyrrole | 1a2-17 | Enamine | 2-(chloromethyl)-4-(5-methyloctahydropyrrolo[3,4-c]pyrrol-2-yl)quinazoline | 1a3-17 |
| (tetrahydro-2H-pyran-4-yl)methanamine | 1a2-18 | Matrix | 2-(chloromethyl)-N-[(tetrahydro-2H-pyran-4-yl)methyl]quinazolin-4-amine | 1a3-18 |

Using reagent 1a1-2

| Amine used | no | source | Intermediate obtained | no |
|---|---|---|---|---|
| (structure) | 1a2-1 | Chembridge | (structure) | 1a3-19 |
| (structure) | 1a2-7 | Maybridge | (structure) | 1a3-20 |

Example 2

(General Procedure B): Preparation of Intermediate 2a3

Mitsonobu Reaction

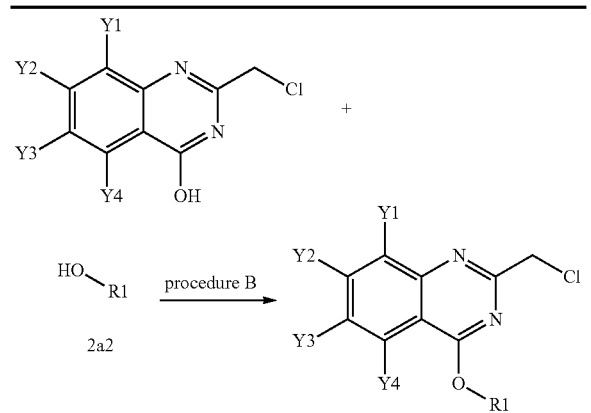

|   | Y1 | Y2 | Y3 | Y4 |
|---|---|---|---|---|
| 2a1-1 | H | H | H | H |
| 2a1-2 | H | H | Br | H |
| 2a1-3 | H | Br | H | H |
| 2a1-4 | H | H | F | H |
| 2a1-5 | H | H | Cl | H |
| 2a1-6 | H | Cl | H | H |
| 2a1-7 | H | H | H | Cl |
| 2a1-8 | Cl | H | H | H |

The hydroxyquinazoline 2a1 (1 equivalent) (2a1-1, Apollo), the alcohol 2a2 (1 equivalent) and Ph$_3$P (1.5 equivalent) are placed in THF and cooled down to 0° C. A solution of DIAD (1.5 to 2.5 equivalents) in THF (0.05 to 0.1 mol/L) is added dropwise and stirring is continued for 5 min at 0° C. The reaction mixture is warmed to RT and stirred for a period varying from 1 h 30 to overnight. Silica gel is added, the solvent is evaporated in vacuo and the residue obtained is purified by flash chromatography on silica using either EtOAc and hexane or ACN and DCM or MeOH and DCM as eluents and/or by SFC-MS using a "2-ethylpyridine" column and a mixture of CO$_2$ and iPrOH as eluent and/or by preparative HPLC.

| Alcohol used | no | source | Intermediate obtained | no |
|---|---|---|---|---|
| HO-(CH₂)₃-OH | 2a2-1 with 2a1-1 | Aldrich Apollo | 2-(chloromethyl)-4-(3-hydroxypropoxy)quinazoline | 2a3-1 |
| (tetrahydrofuran-3-yl)methanol | 2a2-2 with 2a1-1 | Aldrich Apollo | 2-(chloromethyl)-4-((tetrahydrofuran-3-yl)methoxy)quinazoline | 2a3-2 |
| 2-morpholinoethanol | 2a2-3 with 2a1-1 | Acros Apollo | 2-(chloromethyl)-4-(2-morpholinoethoxy)quinazoline | 2a3-3 |
| tetrahydrofuran-3-ol | 2a2-4 with 2a1-1 | Aldrich Apollo | 2-(chloromethyl)-4-((tetrahydrofuran-3-yl)oxy)quinazoline | 2a3-4 |
| (tetrahydrofuran-3-yl)methanol | 2a2-2 with 2a1-6 | Aldrich | 7-chloro-2-(chloromethyl)-4-((tetrahydrofuran-3-yl)methoxy)quinazoline | 2a3-5 |

-continued

| Alcohol used | no | source | Intermediate obtained | no |
|---|---|---|---|---|
| tetrahydrofuran-3-ol | 2a2-4 with 2a1-6 | Aldrich | 7-chloro-2-(chloromethyl)-4-((tetrahydrofuran-3-yl)oxy)quinazoline | 2a3-6 |
| propane-1,3-diol | 2a2-1 with 2a1-6 | Aldrich | 3-((7-chloro-2-(chloromethyl)quinazolin-4-yl)oxy)propan-1-ol | 2a3-7 |
| pyridin-3-ylmethanol | 2a2-5 with 2a1-2 | Aldrich | 6-bromo-2-(chloromethyl)-4-(pyridin-3-ylmethoxy)quinazoline | 2a3-8 |
| 1-(2-hydroxyethyl)pyrrolidin-2-one | 2a2-6 with 2a1-2 | Aldrich | 1-(2-((6-bromo-2-(chloromethyl)quinazolin-4-yl)oxy)ethyl)pyrrolidin-2-one | 2a3-9 |
| 3-fluoropropan-1-ol | 2a2-7 with 2a1-2 | Matrix | 6-bromo-2-(chloromethyl)-4-(3-fluoropropoxy)quinazoline | 2a3-10 |

| Alcohol used | no | source | Intermediate obtained | no |
|---|---|---|---|---|
| 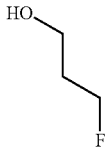 | 2a2-7 with 2a1-3 | Matrix | 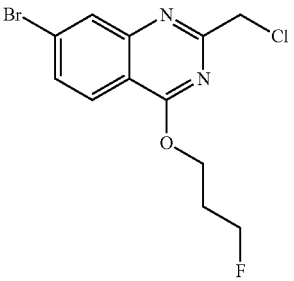 [SMILES: FCCCOc1nc(CCl)nc2cc(Br)ccc12] | 2a3-11 |
| 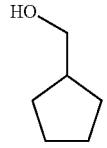 | 2a2-9 with 2a1-3 | Aldrich | 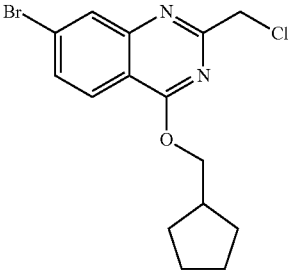 [SMILES: ClCc1nc(OCC2CCCC2)c2ccc(Br)cc2n1] | 2a3-12 |
| 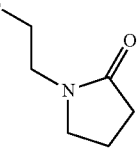 | 2a2-6 with 2a1-3 | Aldrich | 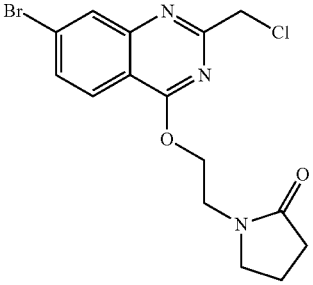 [SMILES: O=C1CCCN1CCOc1nc(CCl)nc2cc(Br)ccc12] | 2a3-13 |
| 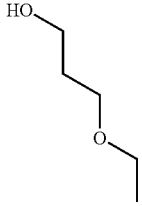 | 2a2-10 with 2a1-3 | Aldrich | 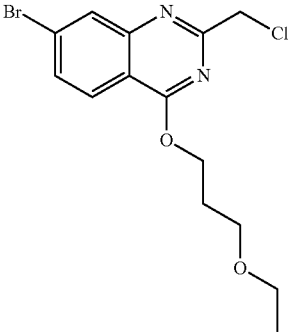 [SMILES: CCOCCCOc1nc(CCl)nc2cc(Br)ccc12] | 2a3-14 |
| 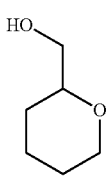 | 2a2-11 with 2a1-6 | Acros | 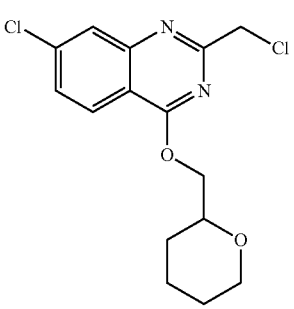 [SMILES: ClCc1nc(OCC2CCCCO2)c2ccc(Cl)cc2n1] | 2a3-15 |

-continued
| Alcohol used | no | source | Intermediate obtained | no |
|---|---|---|---|---|
| 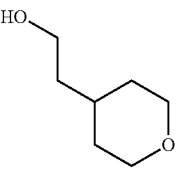 | 2a2-12 with 2a1-6 | Biofine | 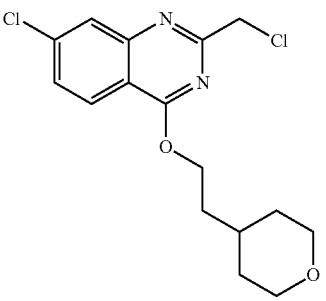 [SMILES: ClCc1nc(OCCC2CCOCC2)c2ccc(Cl)cc2n1] | 2a3-16 |
| 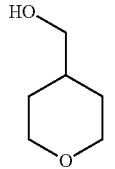 | 2a2-13 with 2a1-6 | Synthonix | 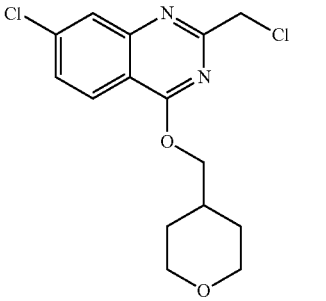 [SMILES: ClCc1nc(OCC2CCOCC2)c2ccc(Cl)cc2n1] | 2a3-17 |
| 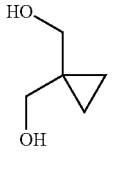 | 2a2-14 with 2a1-6 | Synthonix | 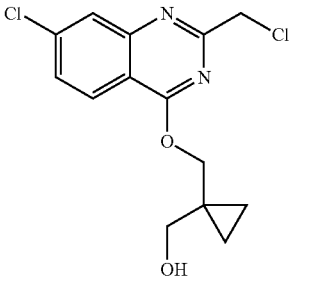 [SMILES: OCC1(COc2nc(CCl)nc3cc(Cl)ccc23)CC1] | 2a3-18 |
| 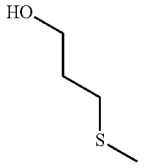 | 2a2-15 with 2a1-6 | Aldrich | 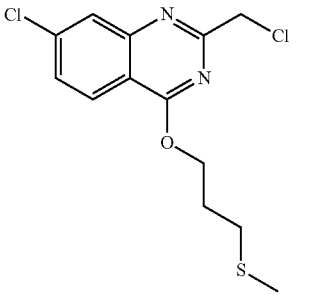 [SMILES: CSCCCOc1nc(CCl)nc2cc(Cl)ccc12] | 2a3-19 |
| 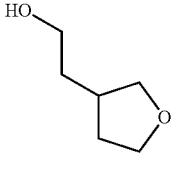 | 2a2-16 with 2a1-6 | Oakwood | 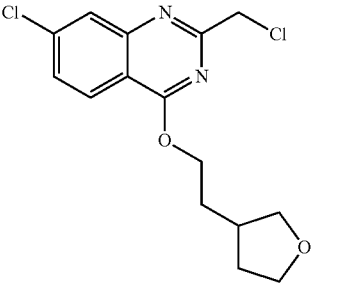 [SMILES: ClCc1nc(OCCC2CCOC2)c2ccc(Cl)cc2n1] | 2a3-20 |

-continued

| Alcohol used | no | source | Intermediate obtained | no |
|---|---|---|---|---|
| oxetan-3-ol | 2a2-17 with 2a1-6 | Accelachem | 7-chloro-2-(chloromethyl)-4-(oxetan-3-yloxy)quinazoline | 2a3-21 |
| (tetrahydrofuran-2-yl)methanol | 2a2-18 with 2a1-3 | Aldrich | 7-bromo-2-(chloromethyl)-4-((tetrahydrofuran-2-yl)methoxy)quinazoline | 2a3-22 |
| (tetrahydrofuran-3-yl)methanol | 2a2-2 with 2a1-2 | Aldrich | 6-bromo-2-(chloromethyl)-4-((tetrahydrofuran-3-yl)methoxy)quinazoline | 2a3-23 |
| (tetrahydrofuran-3-yl)methanol | 2a2-2 with 2a1-3 | Aldrich | 7-bromo-2-(chloromethyl)-4-((tetrahydrofuran-3-yl)methoxy)quinazoline | 2a3-24 |
| (tetrahydrofuran-3-yl)methanol | 2a2-2 with 2a1-4 | Aldrich | 2-(chloromethyl)-6-fluoro-4-((tetrahydrofuran-3-yl)methoxy)quinazoline | 2a3-25 |

-continued
| Alcohol used | no | source | Intermediate obtained | no |
|---|---|---|---|---|
| 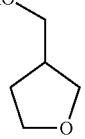 | 2a2-2 with 2a1-5 | Aldrich | 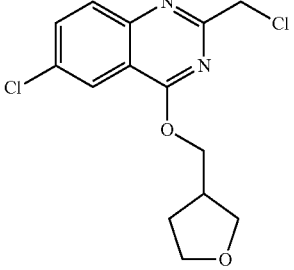 | 2a3-26 |
| 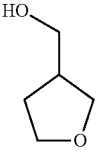 | 2a2-2 with 2a1-7 | Aldrich | 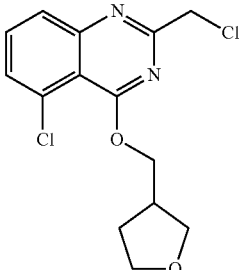 | 2a3-27 |
| 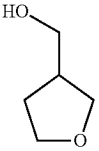 | 2a2-2 with 2a1-8 | Aldrich | 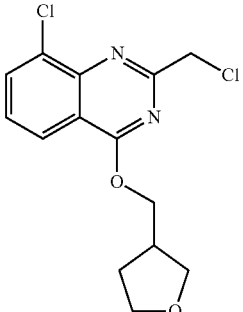 | 2a3-28 |
| 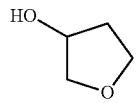 | 2a2-4 with 2a1-3 | Aldrich | 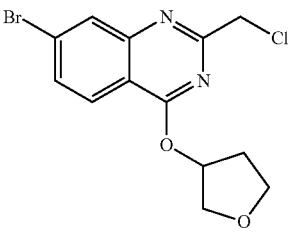 | 2a3-29 |

Example 3

(General Procedure C): Preparation of Compounds 3a2

Final Nucleophilic Substitution

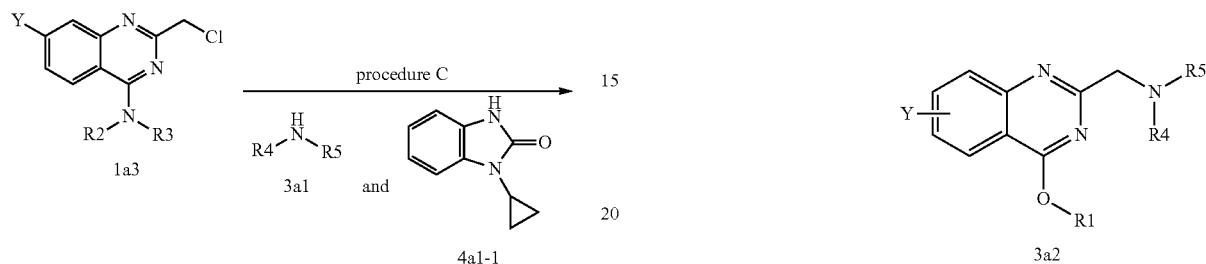

To a solution of the nucleophilic monomer 3a1 (1 to 1.5 equivalents) in a solvent such as DMA or DMF (0.05 mol/L to 0.3 mol/L) is added a base such as an aqueous solution of potassium hydroxide (in the case of DMA) (4 equivalents) or cesium carbonate (in the case of DMF) (2 equivalents) and the reagent 1a3 or 2a3 (1 equivalent) in DMA or DMF. The reaction mixture is stirred at RT for a period varying from 4 h to overnight or longer or is heated (eg at 80° C.). The mixture is

- directly purified by reverse phase HPLC column followed or not by lyophilization
- or water is added, a filtration is performed and the product is washed with hexanes.

This leads to compound 3a2.

| Amine used (supplier) | Products obtained from 3a1-1 |
|---|---|
| 3a1-1 (Enamine) | 1023 |

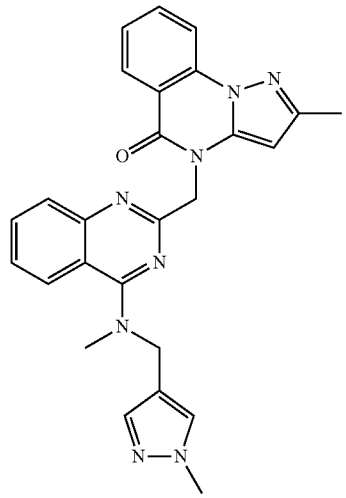
1027
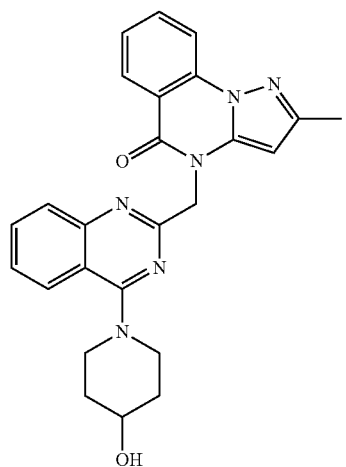
1110
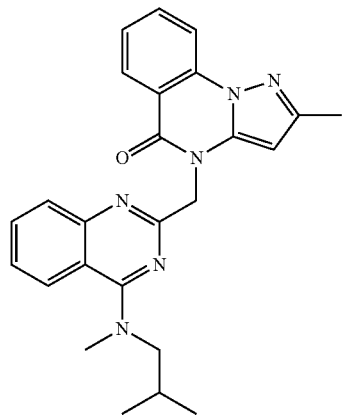
1121

-continued
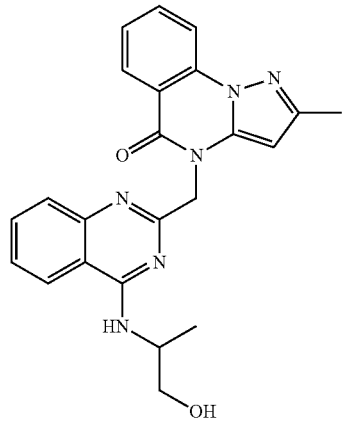
1127
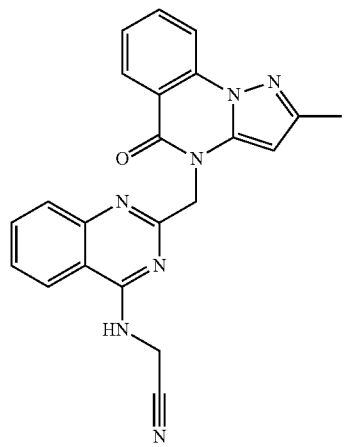
1129
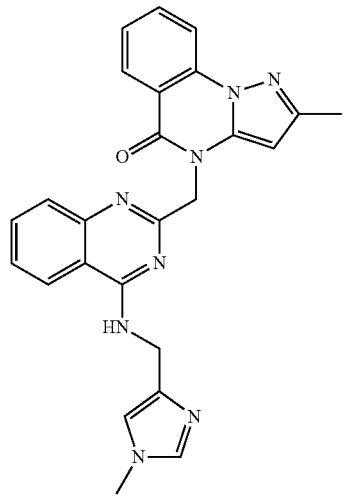
1130

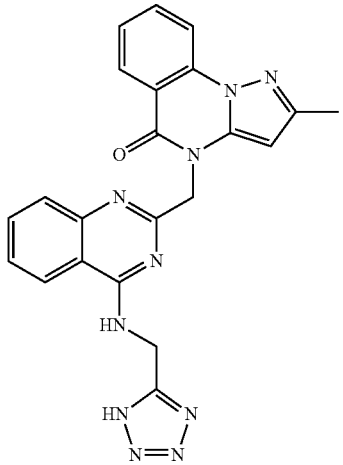
1133
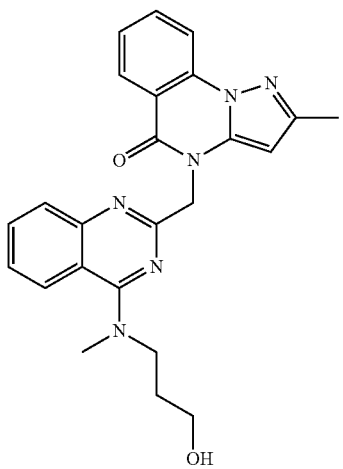
1136
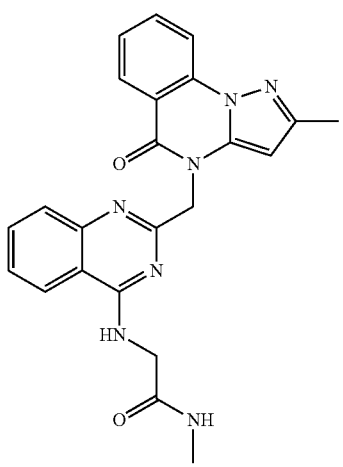
1138

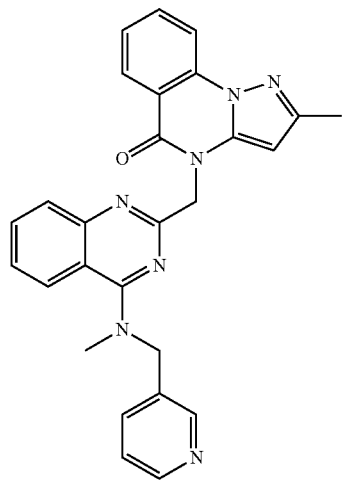
1139
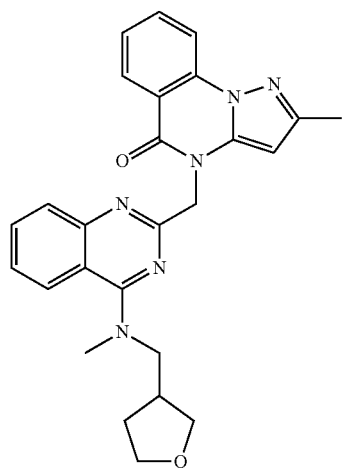
1140
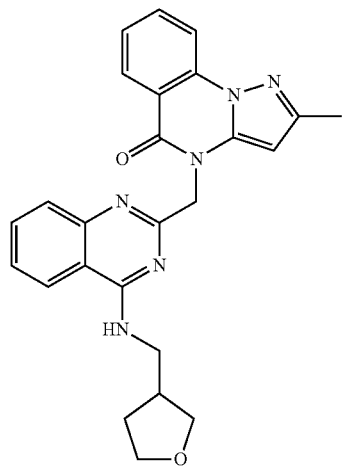
1141

-continued
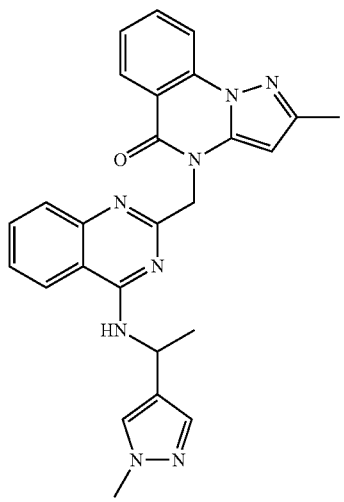
1180
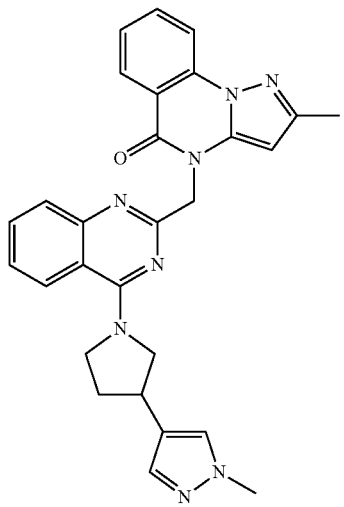
1137

-continued
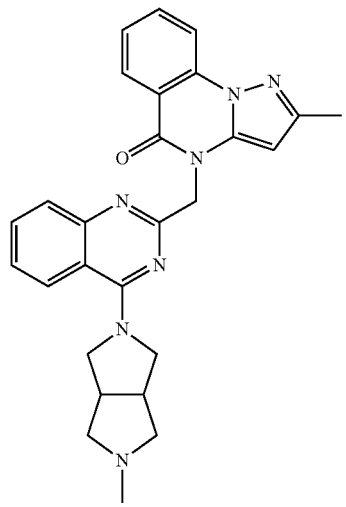
1128
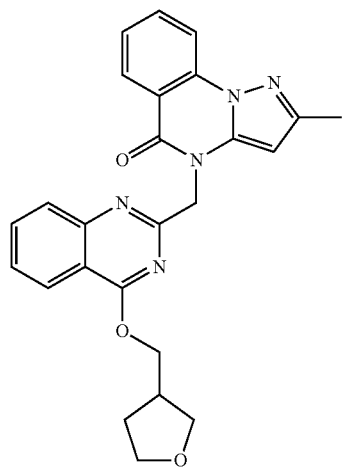
1070
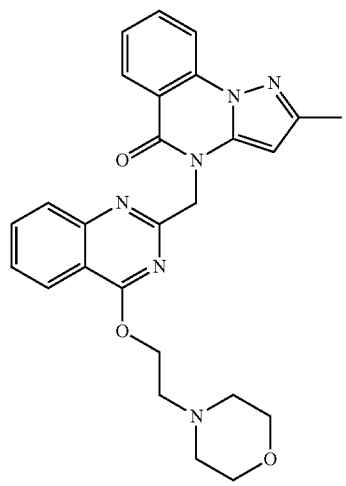
1147

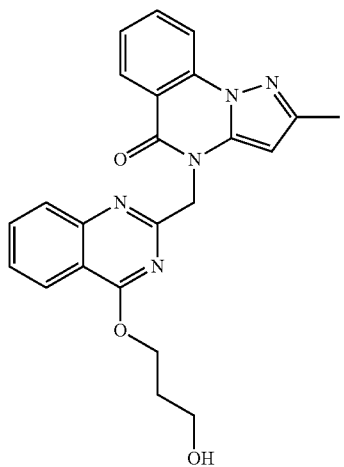 [SMILES: Cc1cc2n(Cc3nc(NC(C)CO)c4ccccc4n3)c(=O)c3ccccc3n2n1]
1152
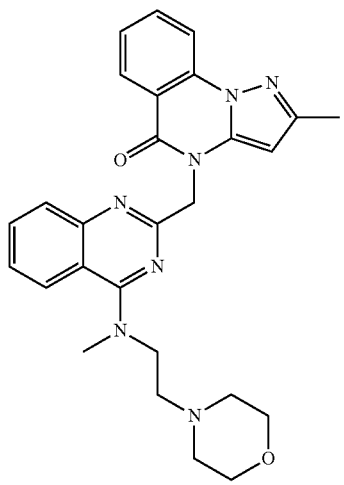
1158
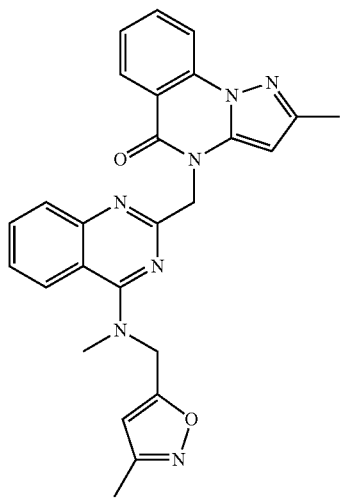
1166

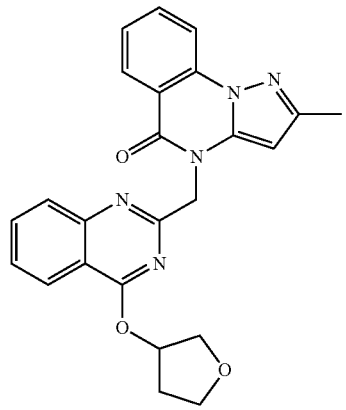
1205
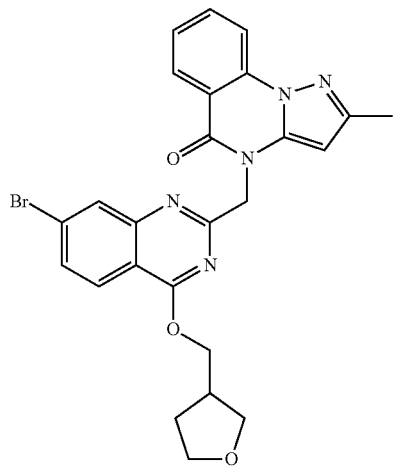
1047
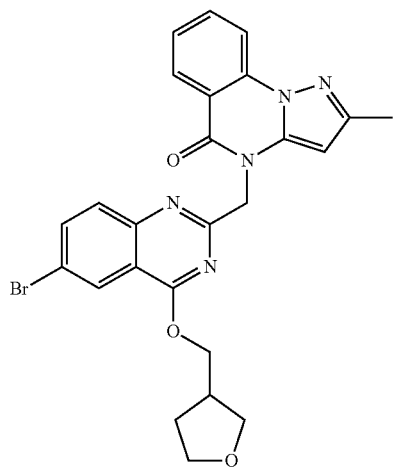
1073

-continued
| Amine used (supplier) | Products obtained from 3a1-2 |
|---|---|
| 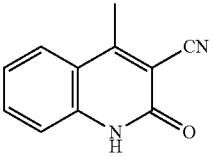<br>3a1-2<br>(Alinda Chem) | 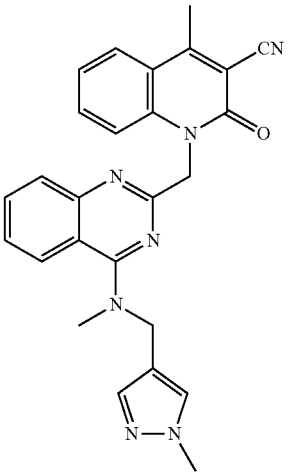<br>1019<br><br>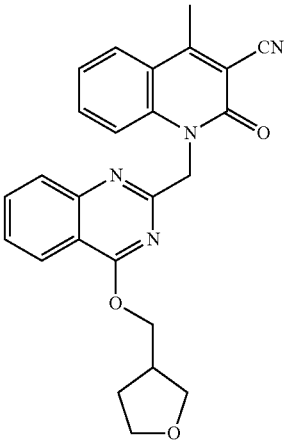<br>1143<br><br>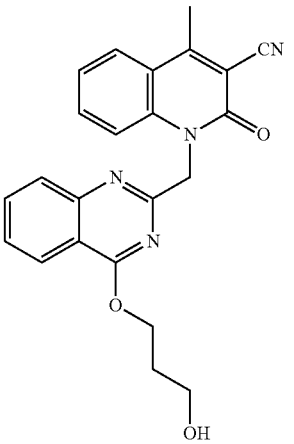<br>1155 |

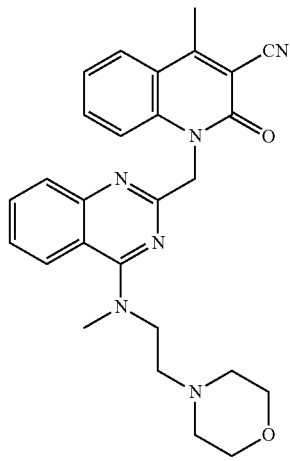
1161
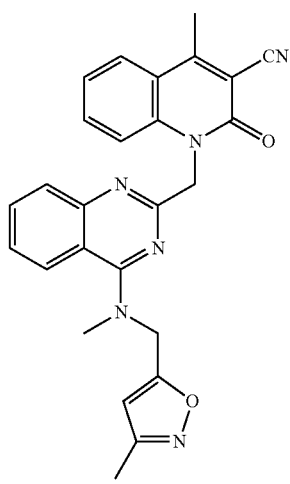
1165
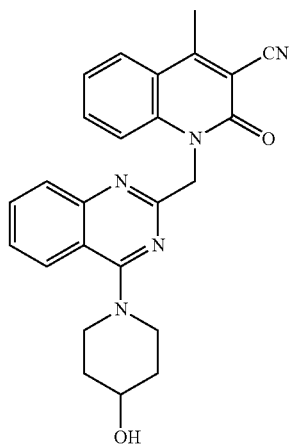
1169

-continued
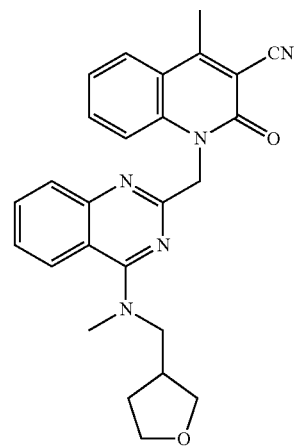
1170
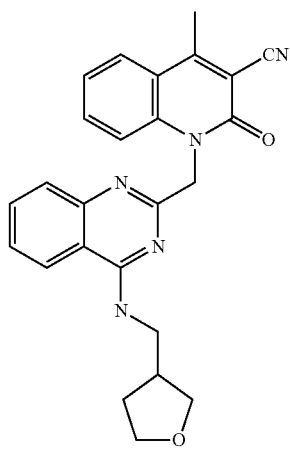
1172
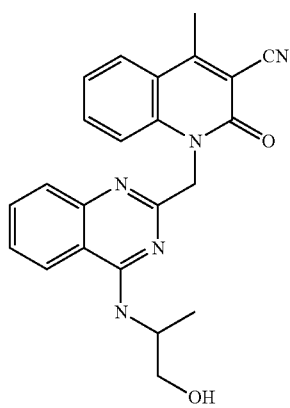
1176

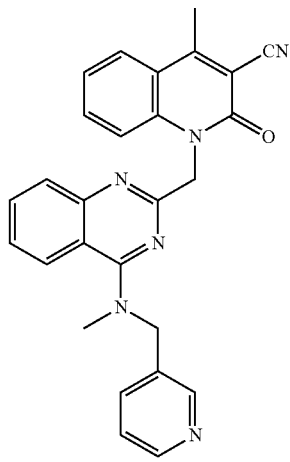
1177
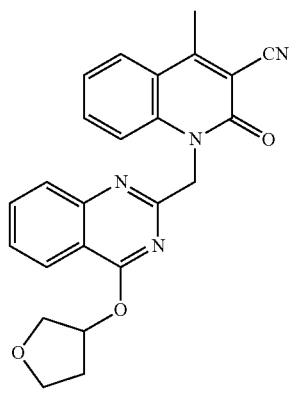
1204
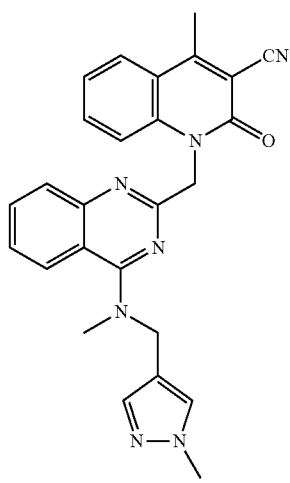
1019

| Amine used (source) | Products obtained from 3a1-3 |
|---|---|
| 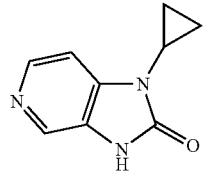<br>3a1-3<br>(Example 10) | 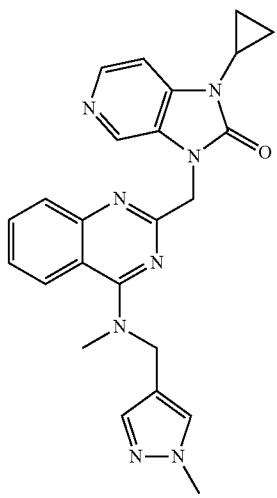<br>1024 |
| | 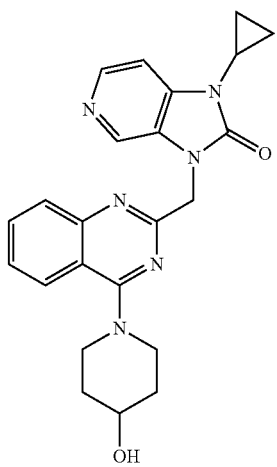<br>1111 |

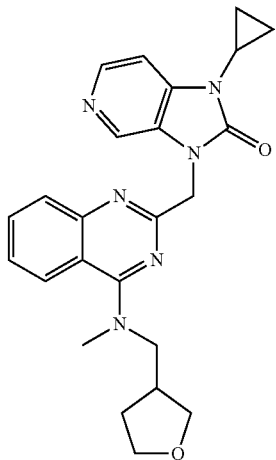
1114
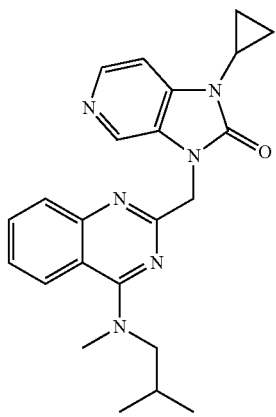
1122
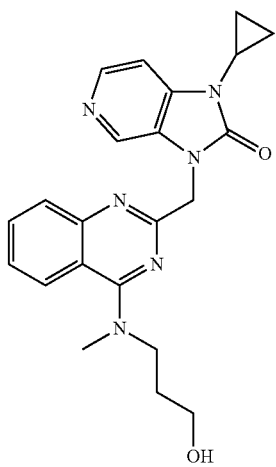
1125

-continued
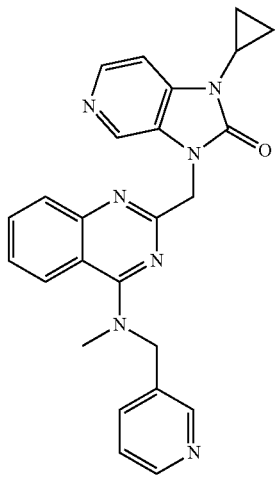
1131
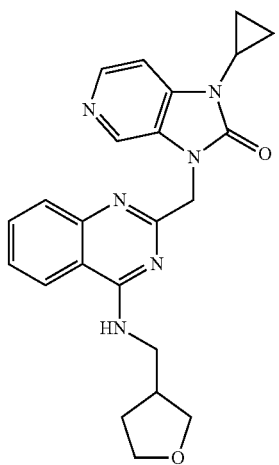
1134
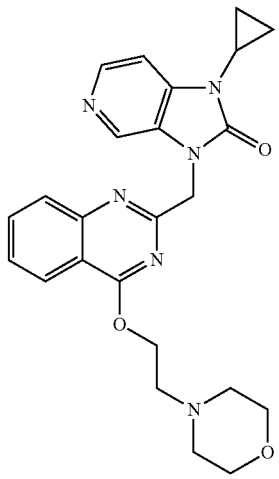
1145

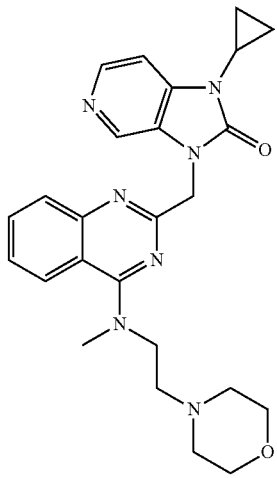
1157
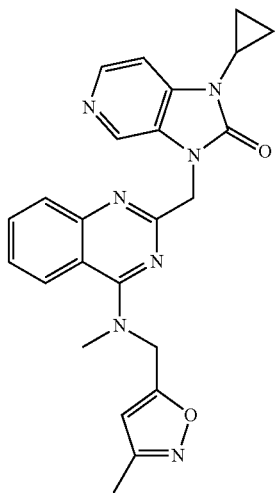
1163
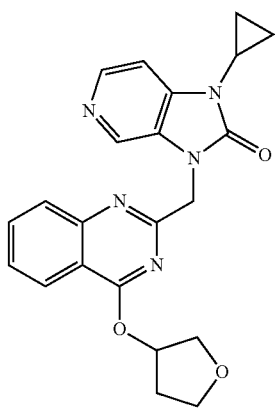
1206

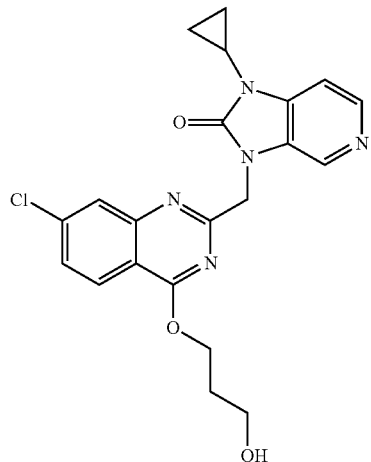
1053
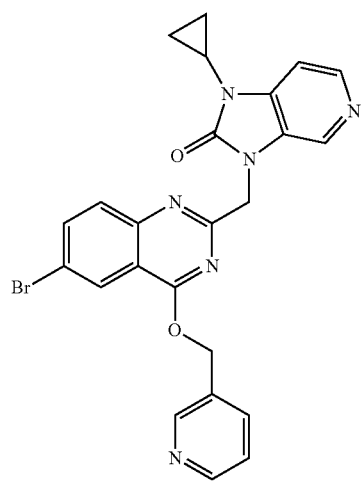
1076
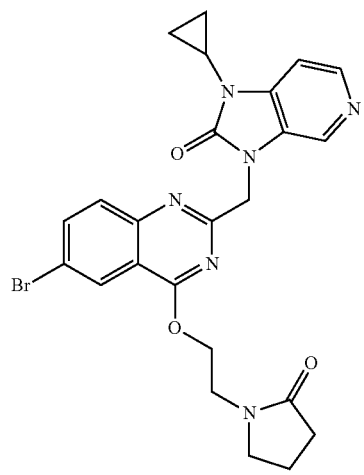
1077

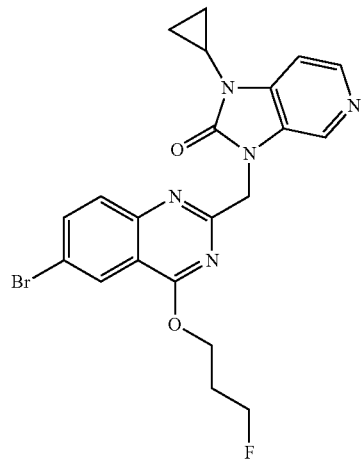
1078
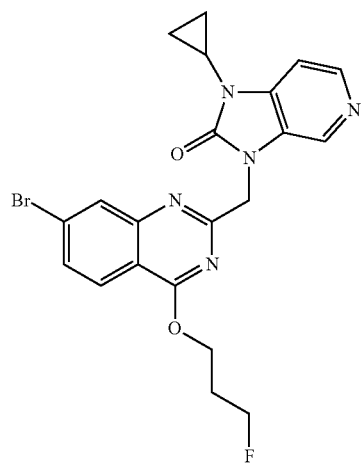
1079
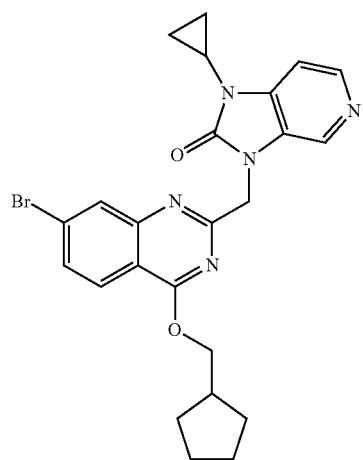
1080

-continued
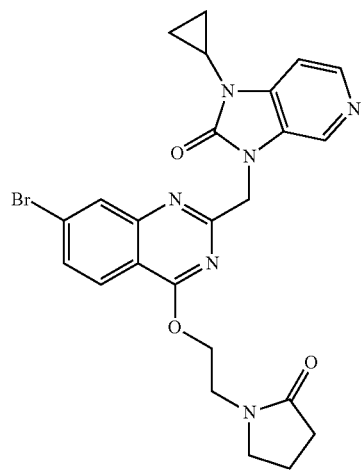
1081
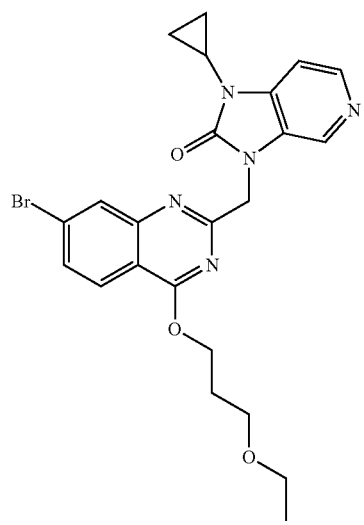 [SMILES: O=c1n(Cc2nc(OCCCF)c3ccc(Br)cc3n2)c2cnccc2n1C1CC1]
1083
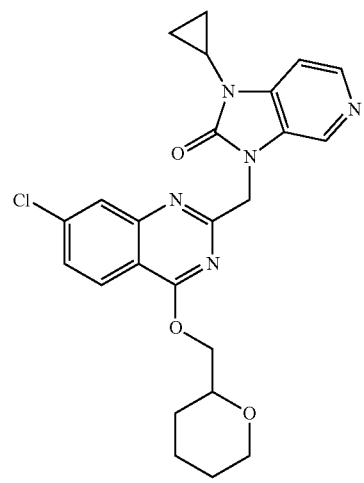
1058

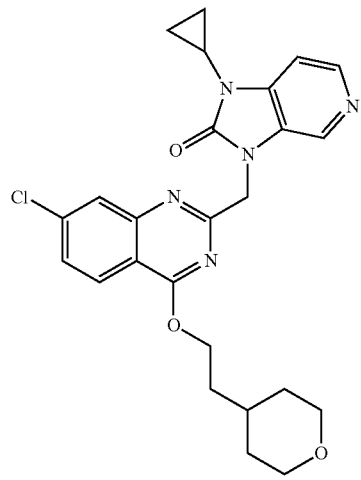
1059
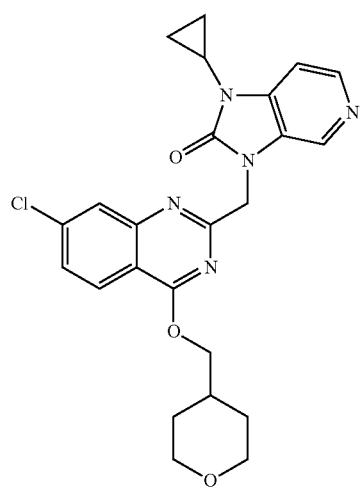
1060
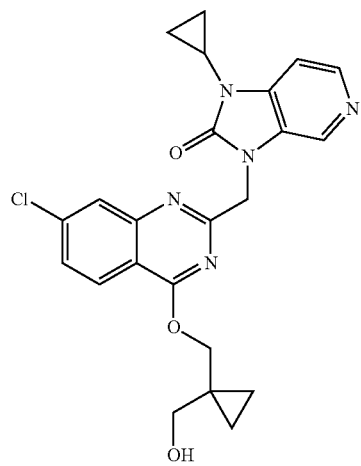
1063

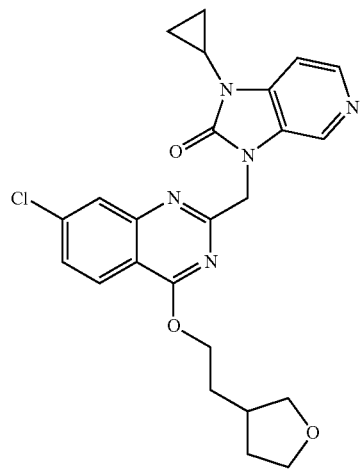
1067
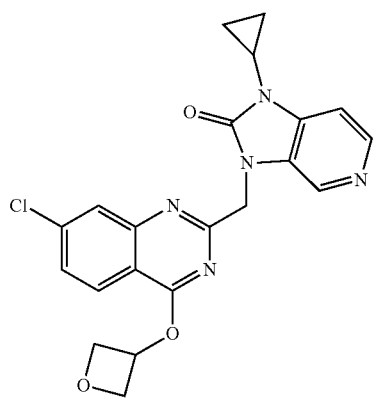
1068
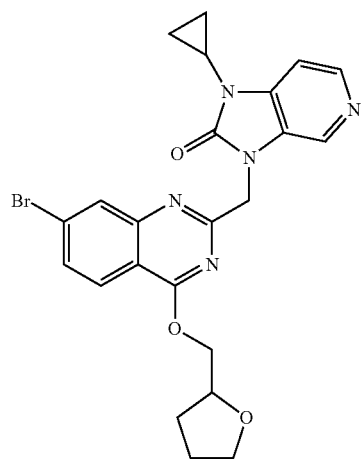
1082

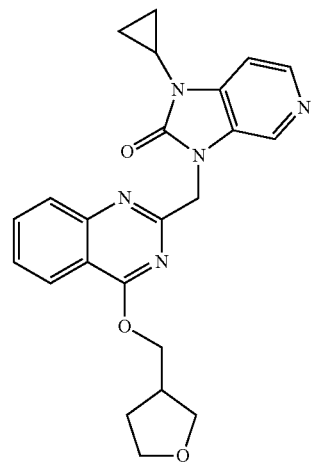
1017
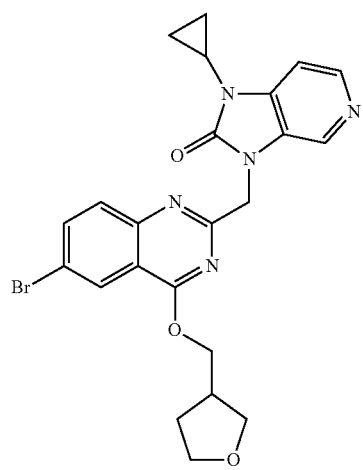
1031
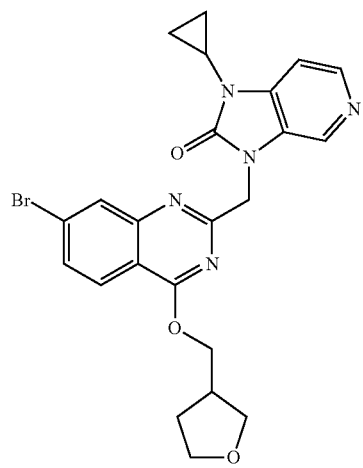
1032

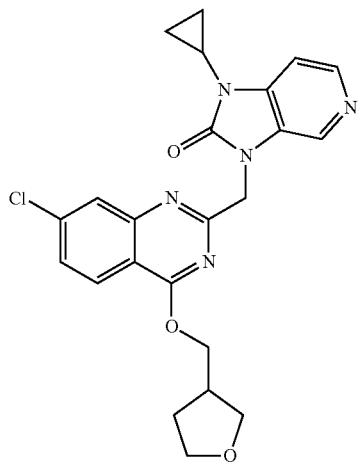
1033
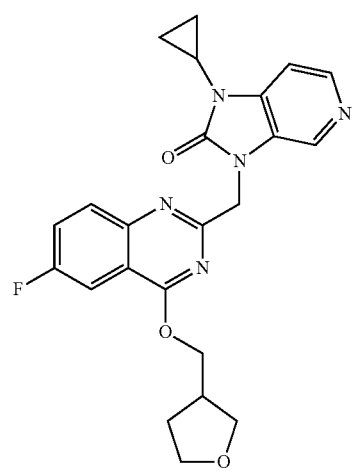
1035
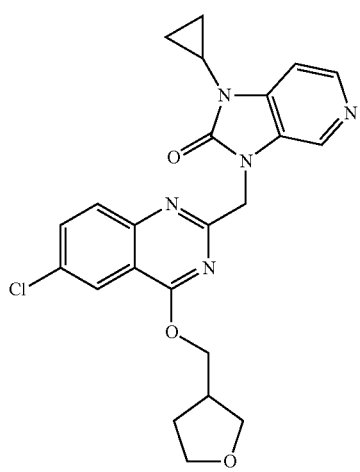
1054

-continued
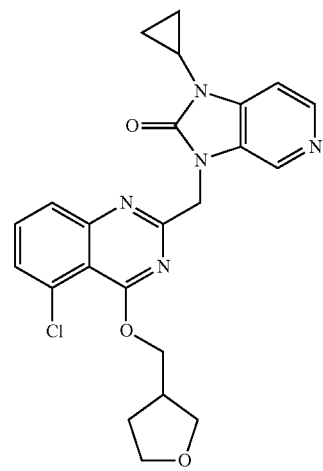
1085
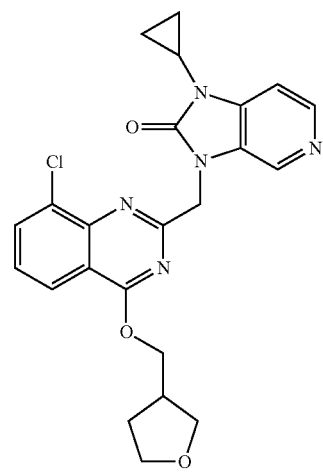
1090
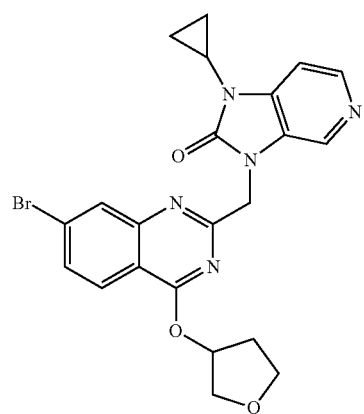
1084

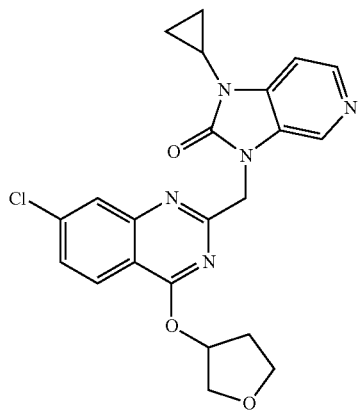
1061
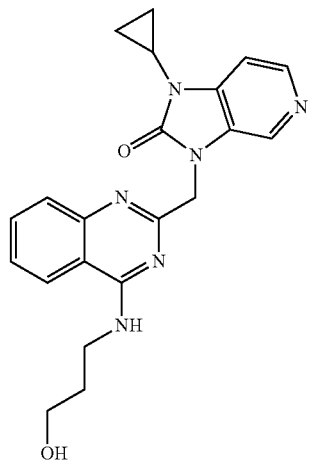
1001
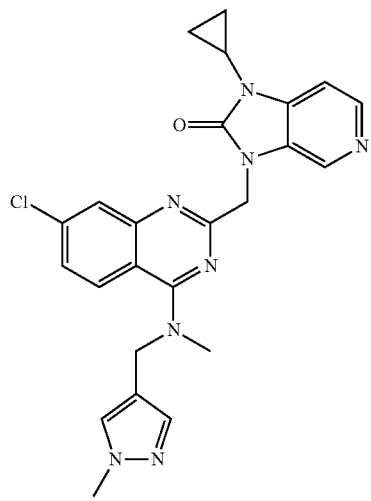
1066

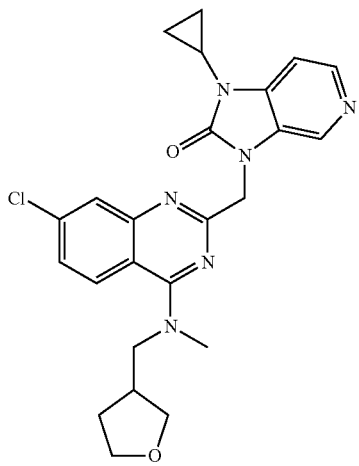
1088
| Amine used (supplier) | Products obtained from 3a1-4 |
|---|---|
| 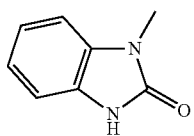<br>3a1-4<br>(Appolo) | 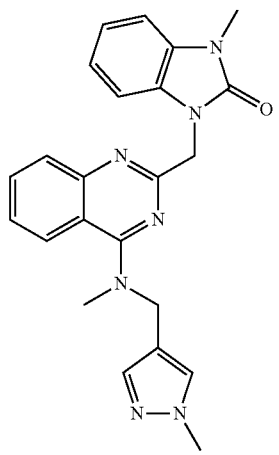<br>1025<br>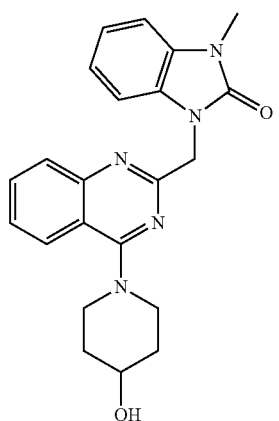<br>1112 |

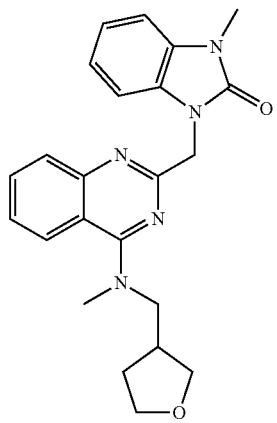
1115
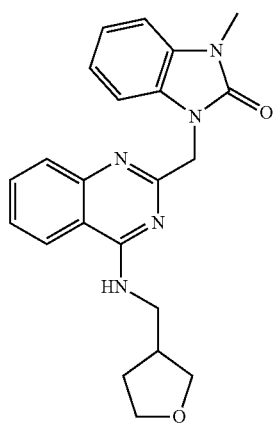
1120
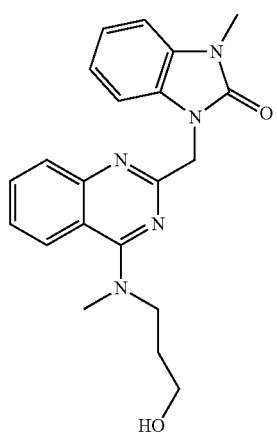
1126

-continued
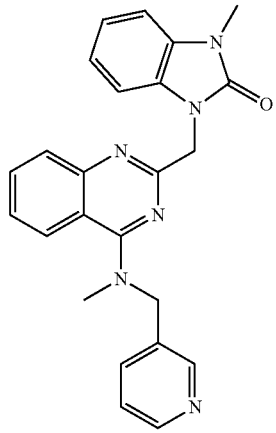
1132
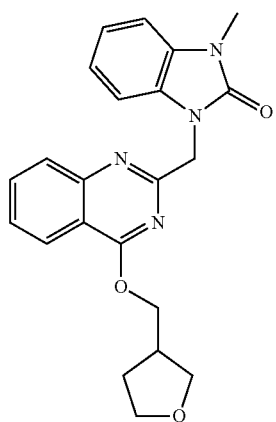
1142
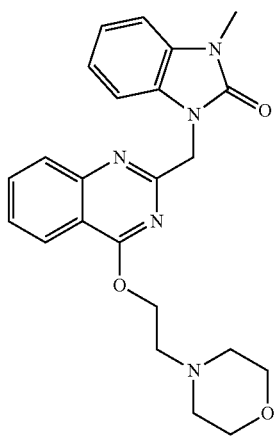
1148

-continued
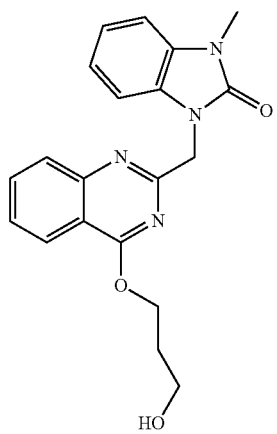
1153
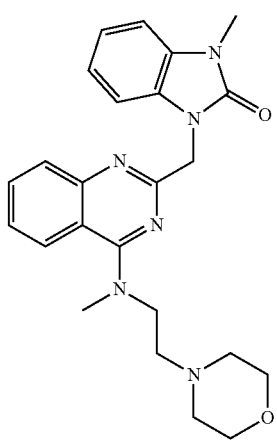
1159
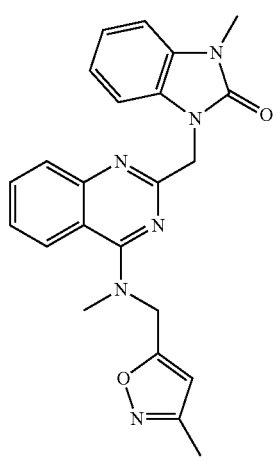
1167

| Amine used (supplier) | Products obtained from 3a1-5 |
|---|---|
| 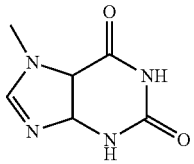<br>3a1-5<br>(Sigma) | 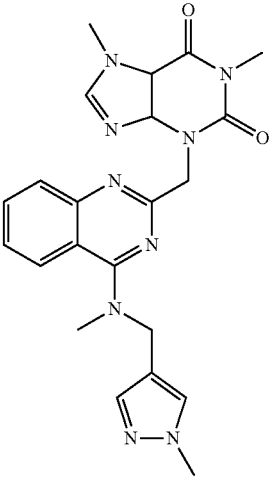<br>1109<br><br>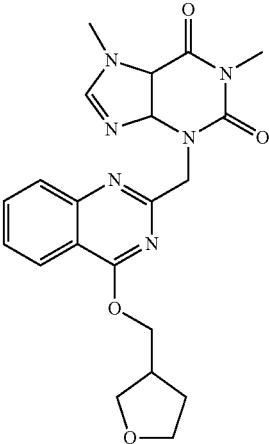<br>1144<br><br>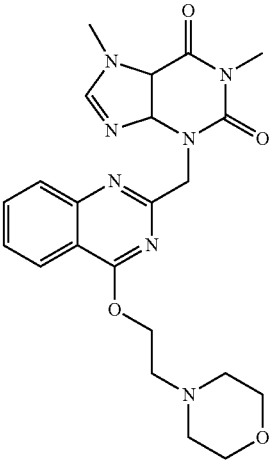<br>1150 |

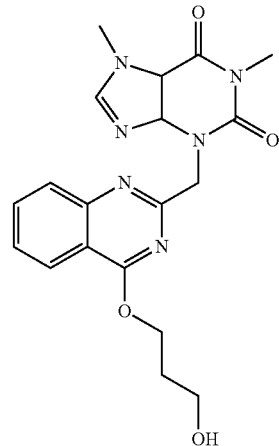
1156
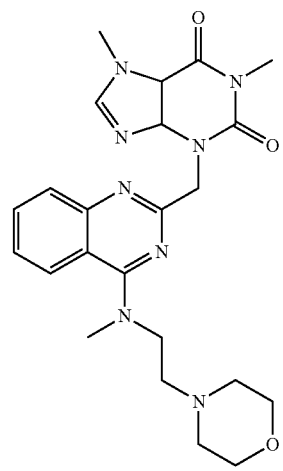
1162
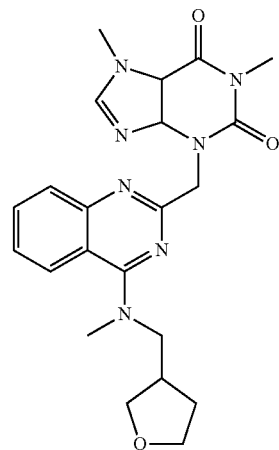
1171

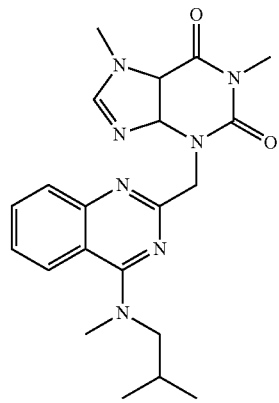
1173
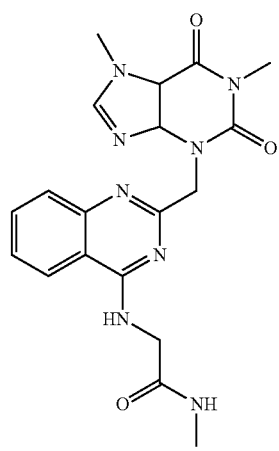
1174

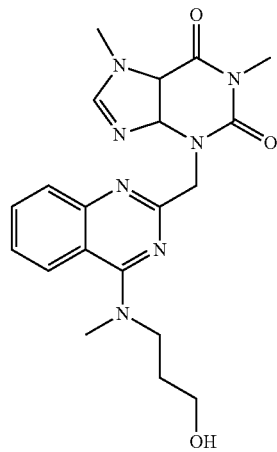
1175
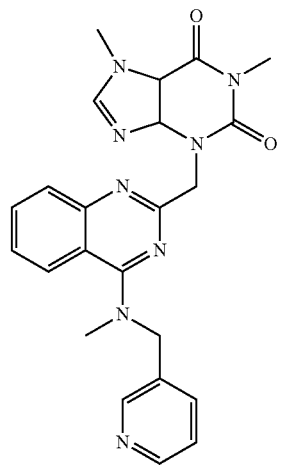
1178
| Amine used (supplier) | Products obtained from 3a1-6 |
|---|---|
| 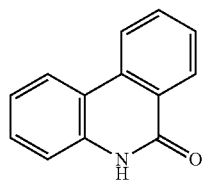<br>3a1-6<br>(Aldrich) | 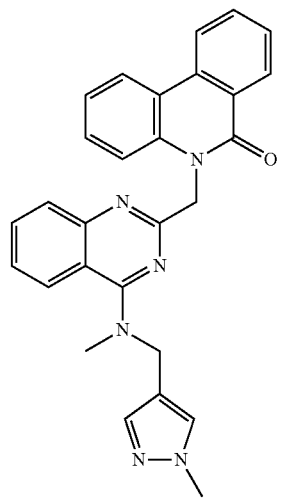<br>1021 |

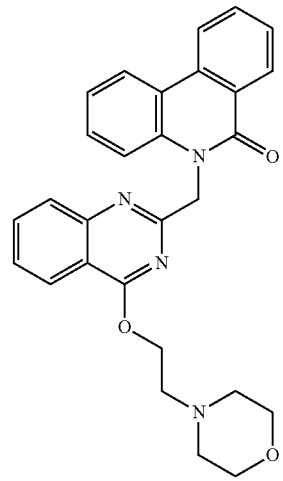
1149
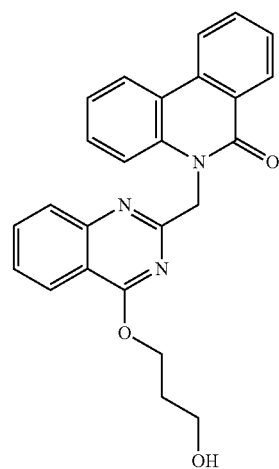
1154
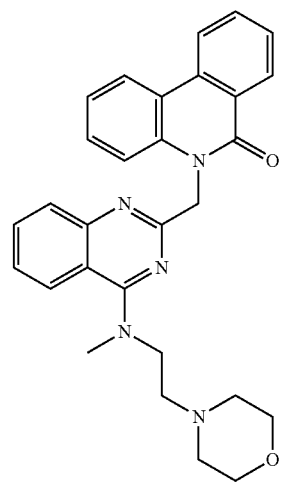
1160

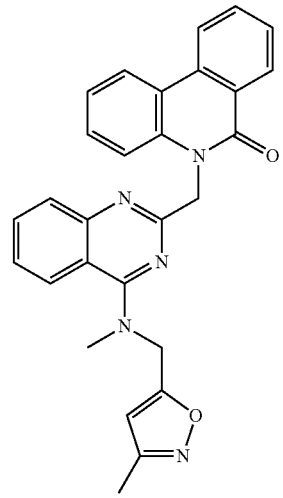
1168
| Amine used (source) | Products obtained from 3a1-7 |
|---|---|
| 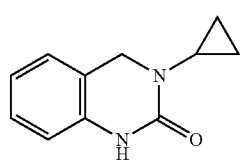<br>3a1-7<br>(Example 9) | 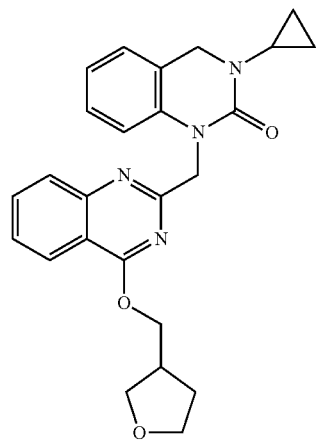<br>1071<br>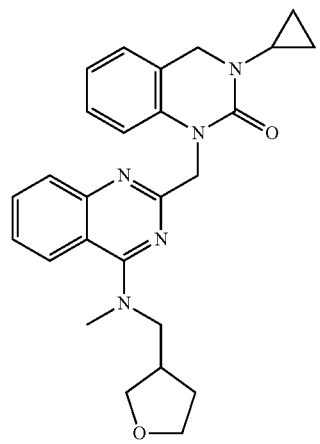<br>1118 |

-continued
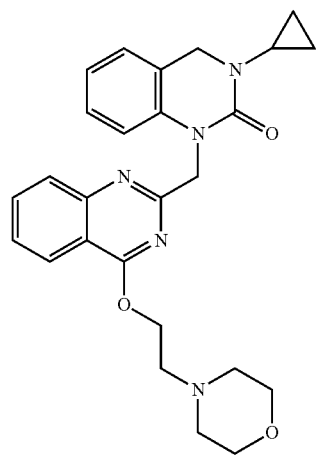
1146
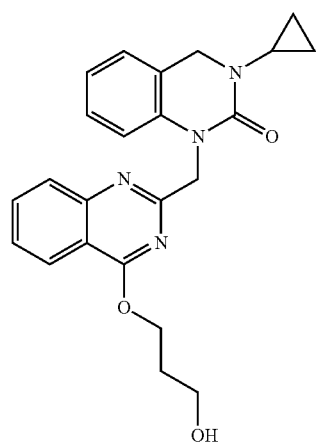
1151
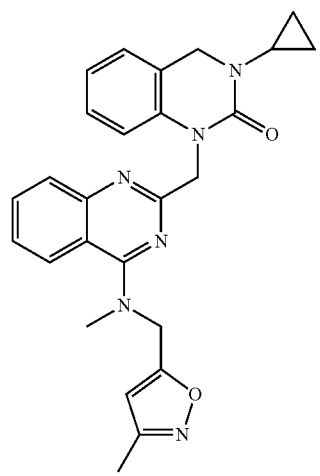
1164

| Amine used (source) | Products obtained from 3a1-8 |
|---|---|
| 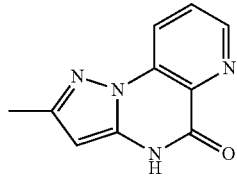<br>3a1-8<br>(Example 13) | 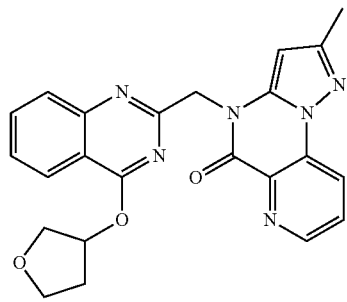<br>1207 |
| | 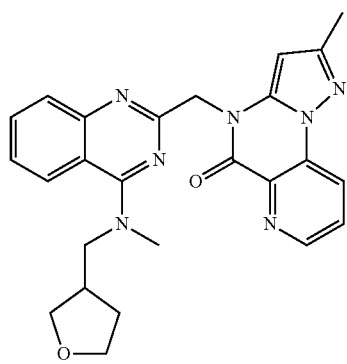<br>1209 |
| | 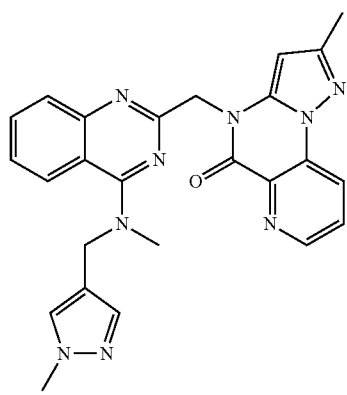<br>1210 |

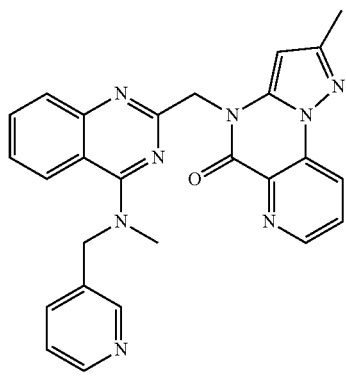
1211
| Amine used (supplier) | Products obtained from 3a1-9 |
|---|---|
| 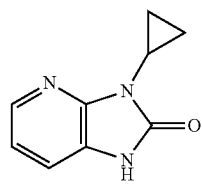<br>3a1-9<br>(Focus) | 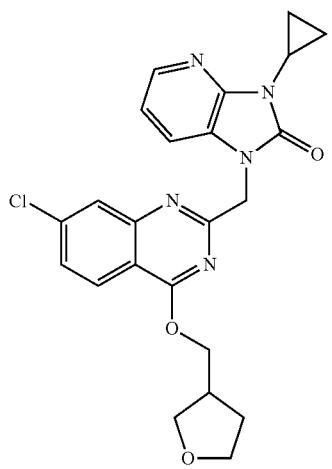<br>1217<br>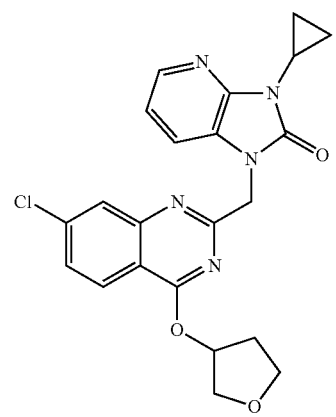<br>1218 |

-continued
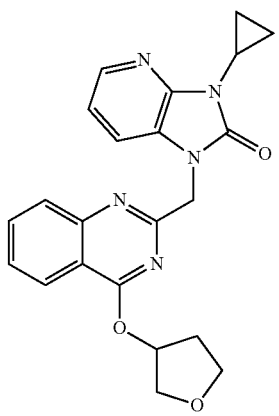
1220
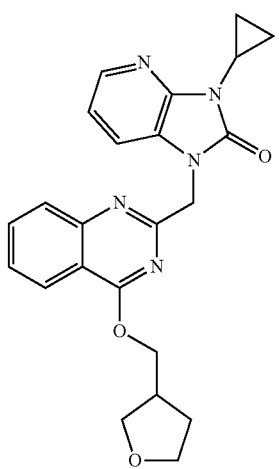
1222
| Amine used (source) | Products obtained from 3a1-10 |
|---|---|
| 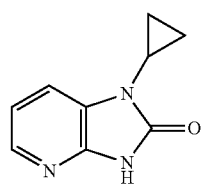
3a1-10
(Example 12) | 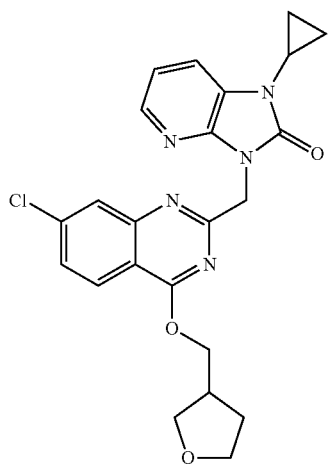
1216 |

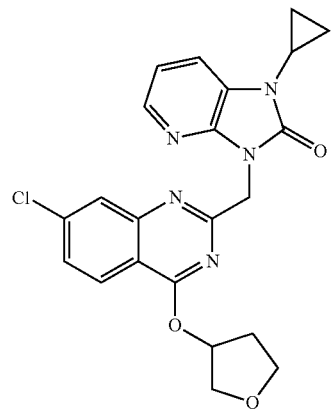
1219
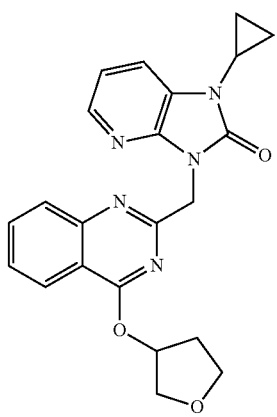
1221
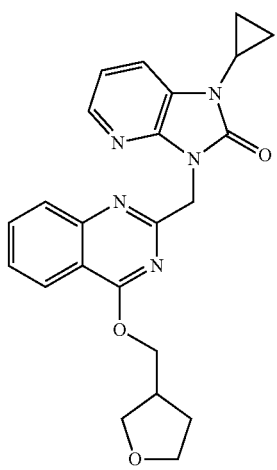
1020

-continued
| Amine used (supplier) | Products obtained from 3a1-11 |
|---|---|
| 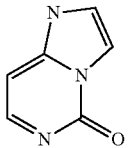<br>3a1-11<br>(Peakdale-Int) | 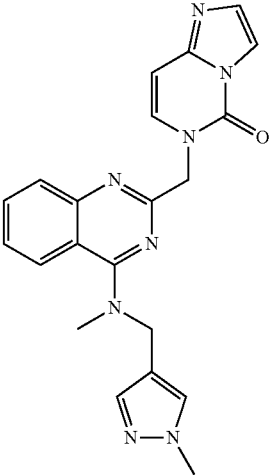<br>1030<br>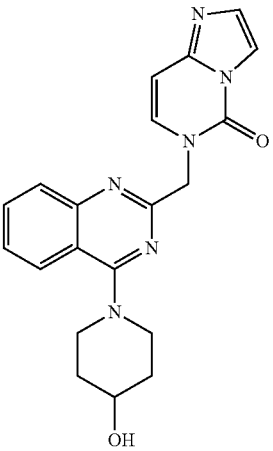<br>1113<br>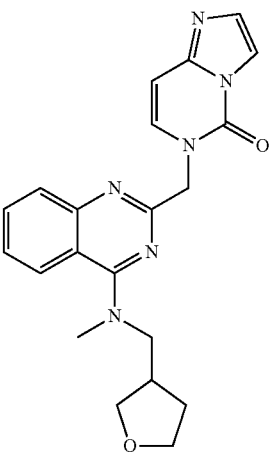<br>1119 |

-continued
| Amine used (supplier) | Products obtained from 3a1-12 |
|---|---|
| 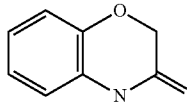<br>3a1-12<br>(Aldrich) | 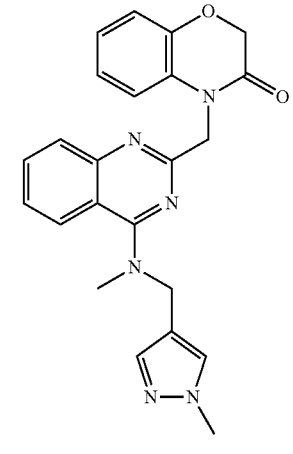<br>1022 |
| | 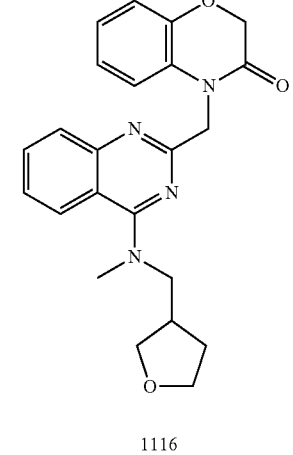<br>1116 |
| | 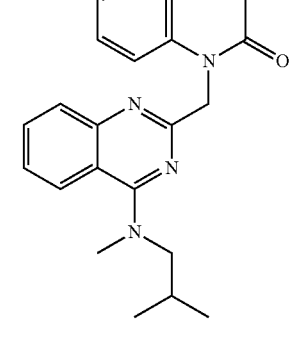<br>1123 |

-continued
| Amine used (source) | Products obtained from 3a1-13 |
|---|---|
| 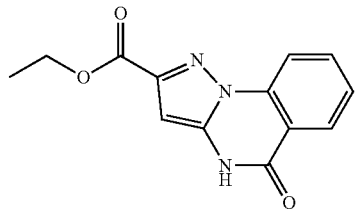<br>3a1-13<br>(Example 8) | 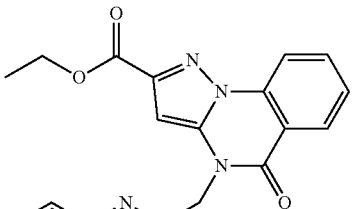<br>1182<br>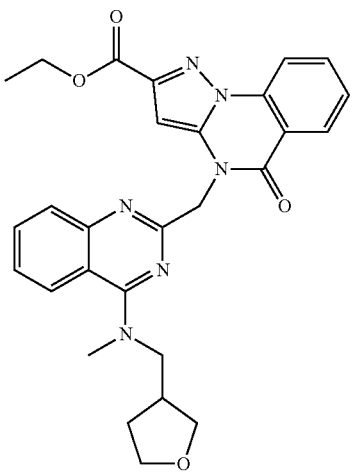<br>1188<br>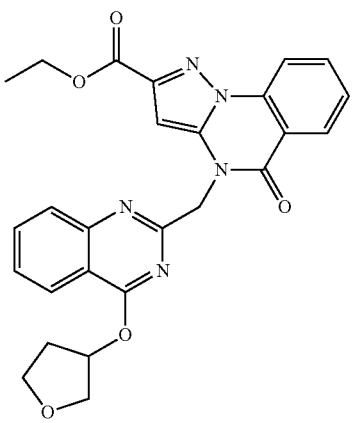<br>1195 |

| Amine used (source) | Products obtained from 3a1-14 |
|---|---|
| 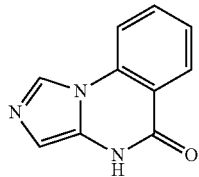
3a1-14
(Example 6) | 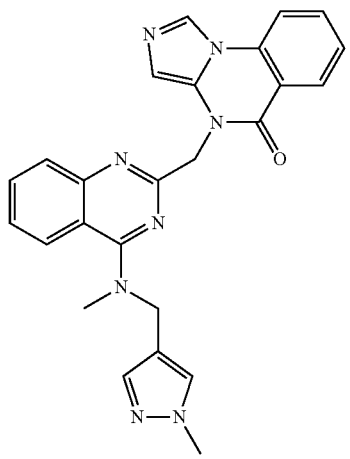
1183
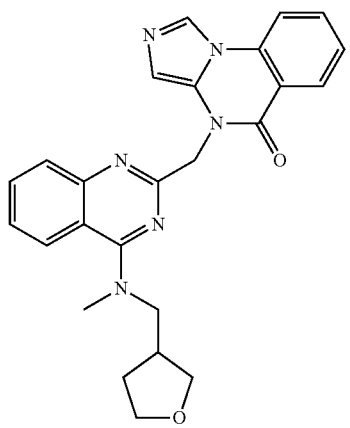
1189
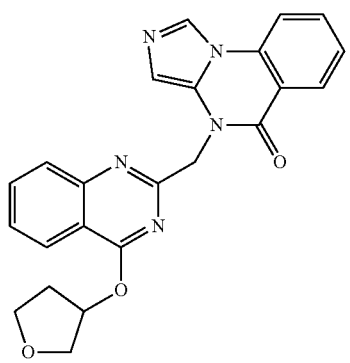
1196 |

-continued
| Amine used (source) | Products obtained from 3a1-15 |
|---|---|
| 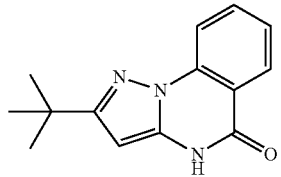
3a1-15
(Example 13) | 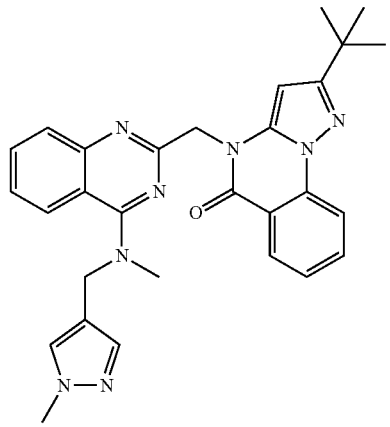 [SMILES: CN(CC1CCOC1)c1nc(Cn2c(=O)c3ccccc3n3nc(C(C)(C)C)cc23)nc2ccccc12]
1184
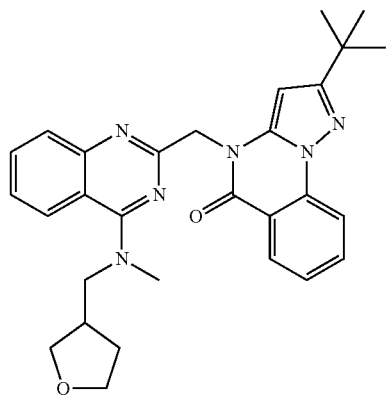
1190
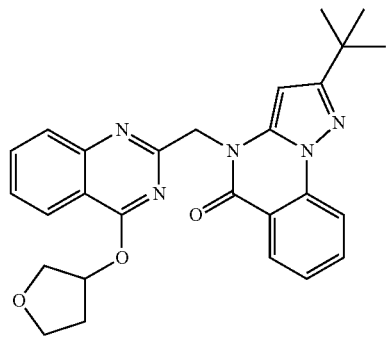
1197 |

| Amine used (source) | Products obtained from 3a1-16 |
|---|---|
| 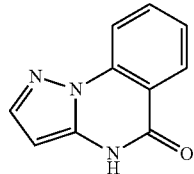<br>3a1-16<br>Example 14 | 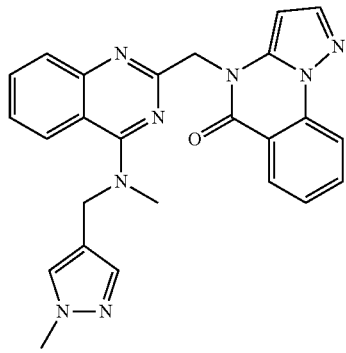 [SMILES: CN(CC1CCOC1)c1nc(Cn2c(=O)c3ccccc3n3nccc23)nc2ccccc12]<br>1185 |
| | 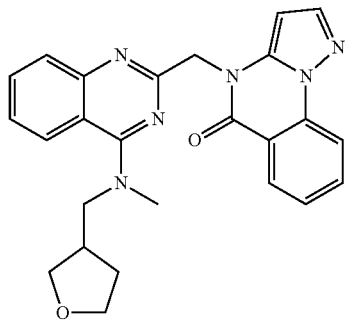<br>1191 |
| | 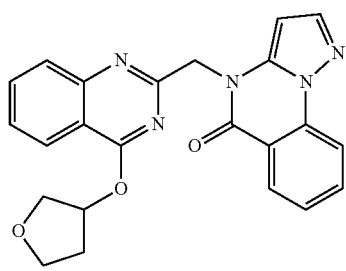<br>1198 |

| Amine used (source) | Products obtained from 3a1-17 |
|---|---|
| 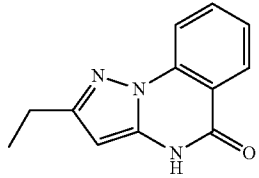<br>3a1-17<br>(Example 13) | 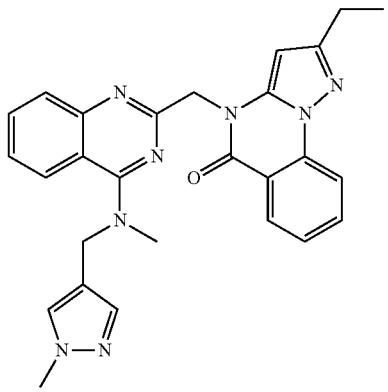 [SMILES: CCc1cc2n(Cc3nc(N(C)CC4CCOC4)c4ccccc4n3)c(=O)c3ccccc3n2n1]<br>1186 |
| | 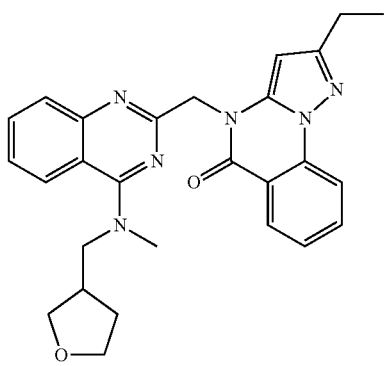<br>1192 |
| | 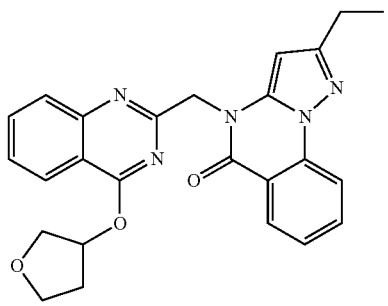<br>1199 |

-continued
| Amine used (supplier) | Products obtained from 3a1-18 |
|---|---|
| 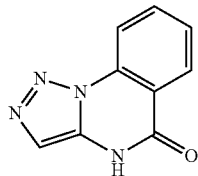<br>3a1-18<br>(Princeton) | 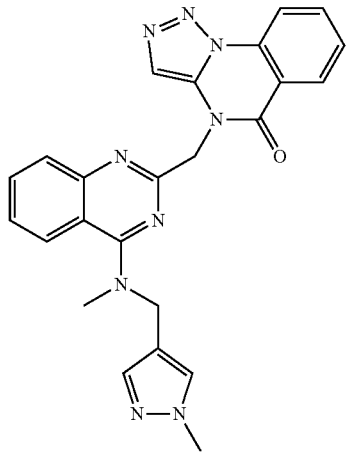<br>1187<br><br>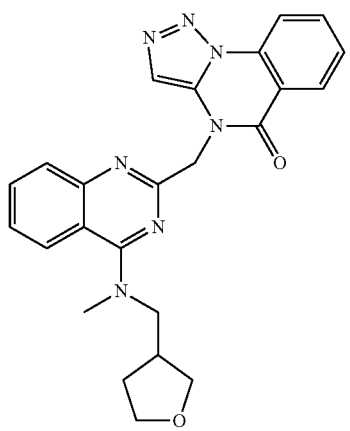<br>1193<br><br>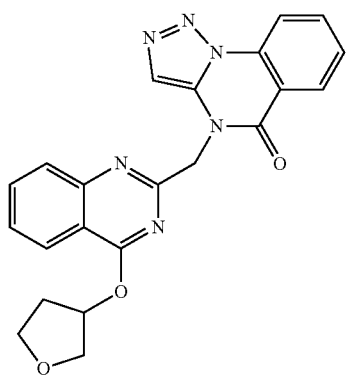<br>1200 |

-continued
| Amine used (supplier) | Products obtained from 3a1-19 |
|---|---|
| 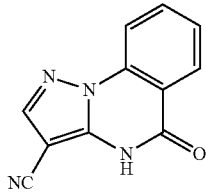
3a1-19
(Bionet) | 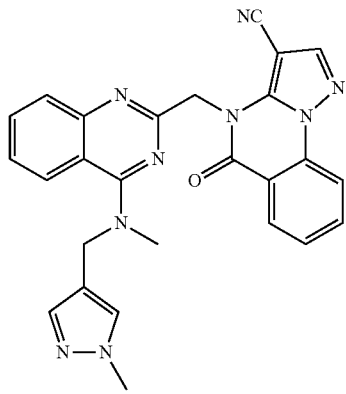
1179
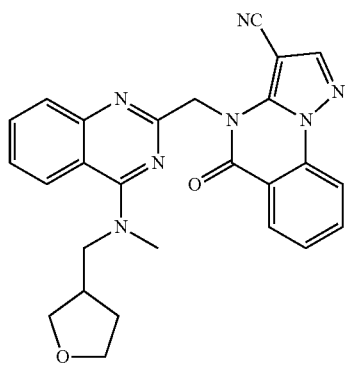
1194
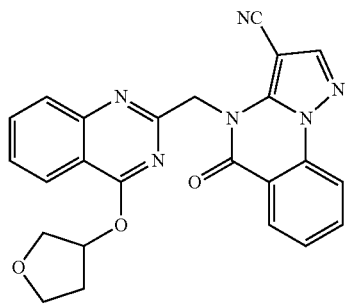
1202 |

-continued
| Amine used (supplier) | Products obtained from 3a1-20 |
|---|---|
| 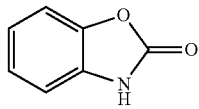<br>3a1-20<br>(Aldrich) | 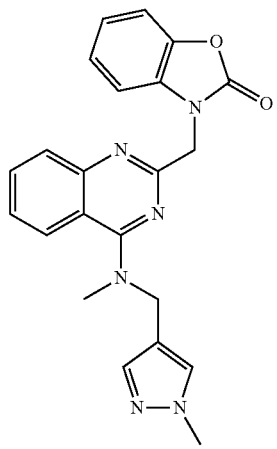<br>1026 |
|  | 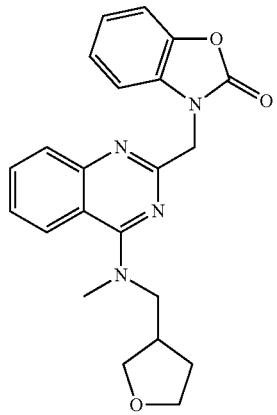<br>1117 |
| Amine used (supplier) | Products obtained from 3a1-21 |
|---|---|
| 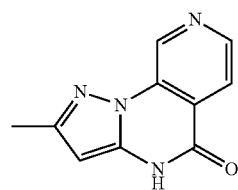<br>3a1-21<br>(Example 13) | 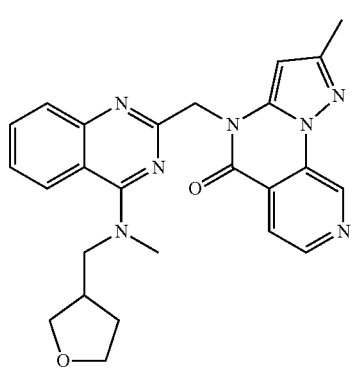<br>1208 |

-continued
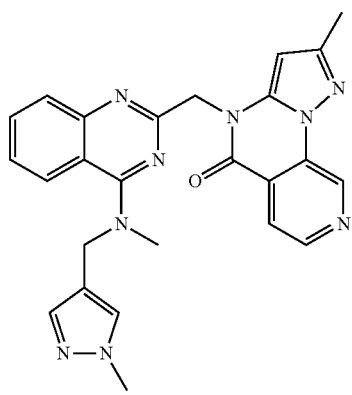
1212
| Amine used (supplier) | Products obtained from 3a1-22 |
|---|---|
| 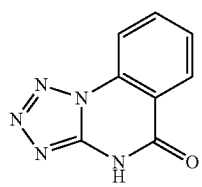<br>3a1-22<br>(Zerenex) | 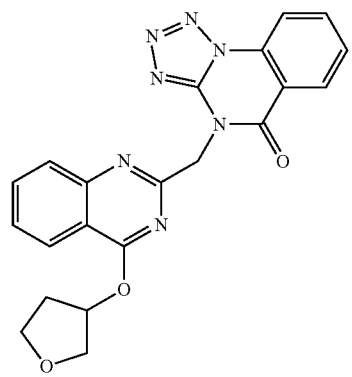<br>1201<br><br>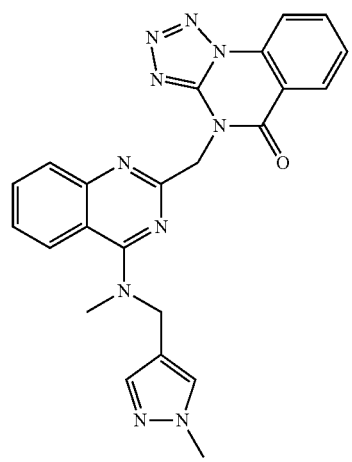<br>1203 |

-continued
| Amine used (supplier) | Products obtained from 3a1-23 |
|---|---|
| 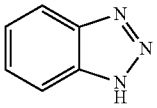<br>3a1-23<br>(Aldrich) | 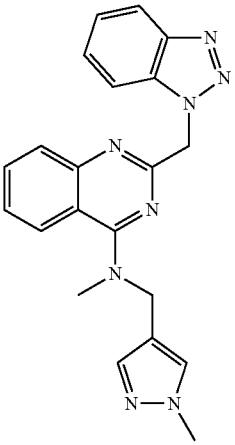<br>1028 |
| Amine used (supplier) | Products obtained from 3a1-24 |
|---|---|
| 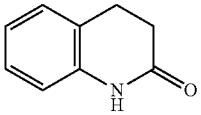<br>3a1-24<br>(Aldrich) | 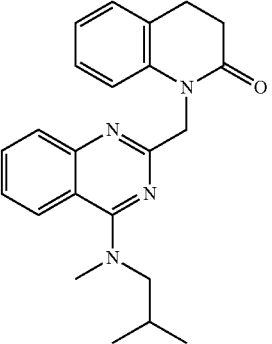<br>1124 |
| Amine used (source) | Products obtained from 3a1-25 |
|---|---|
| 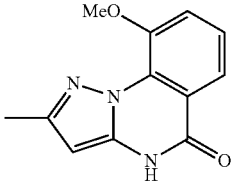<br>3a1-25<br>(see example 13) | 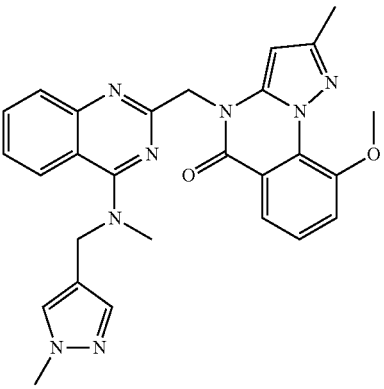<br>1215 |

| Amine used (source) | Products obtained from 3a1-26 |
|---|---|
| 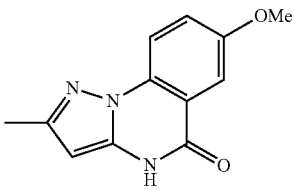 3a1-26 (see example 13) | 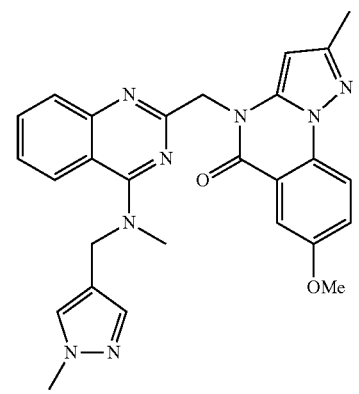 1135 |
| Amine used (source) | Products obtained from 3a1-27 |
|---|---|
| 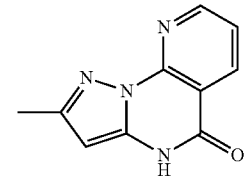 3a1-27 (see example 13) | 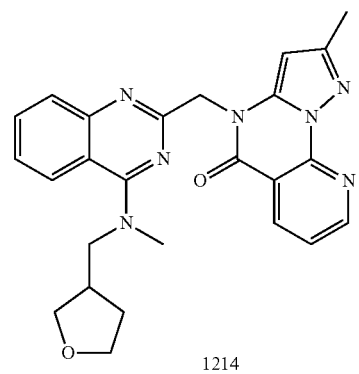 [SMILES: Cc1cc2n(Cc3nc(N(C)CC4CCOC4)c4ccccc4n3)c(=O)c3cccnc3n2n1] 1214 |
| Amine used (source) | Products obtained from 3a1-28 |
|---|---|
| 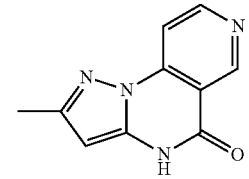 3a1-28 (see example 7) | 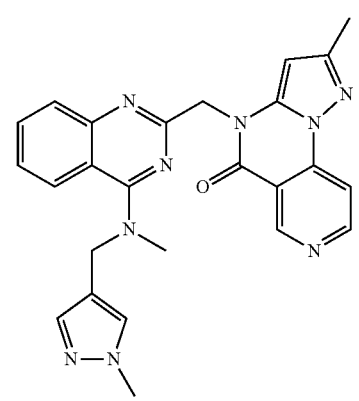 1213 |

| Amine used (supplier) | Products obtained from 3a1-29 |
|---|---|
| 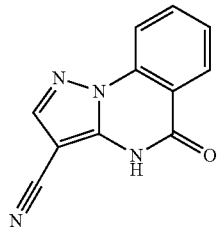<br>3a1-29<br>(Bionet-Frag) | 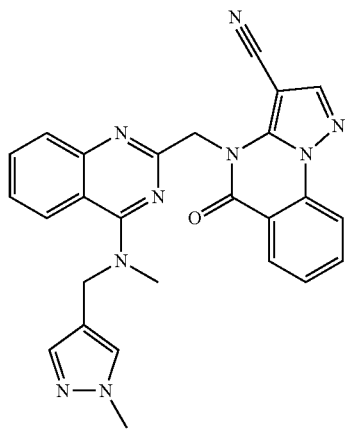<br>1179 |
| Amine used (supplier) | Products obtained from 3a1-30 |
|---|---|
| 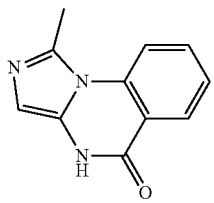<br>3a1-30<br>(see example 23) | 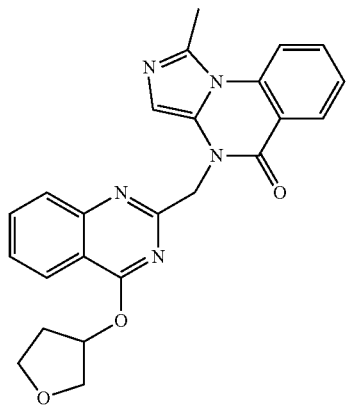<br>1097<br><br>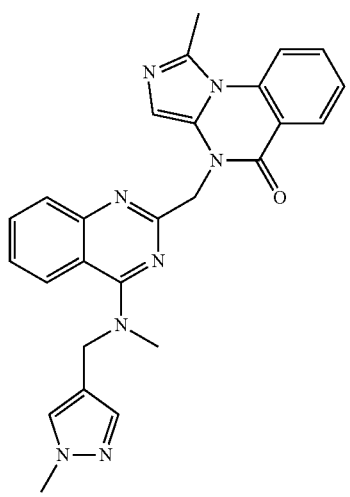<br>1098 |

-continued
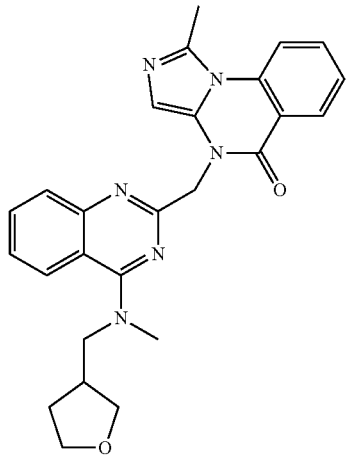
1099
| Amine used (source) | Products obtained from 3a1-31 |
|---|---|
| 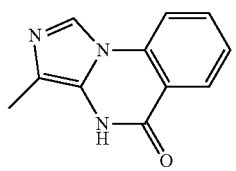<br><br>3a1-31<br>(see example 24) | 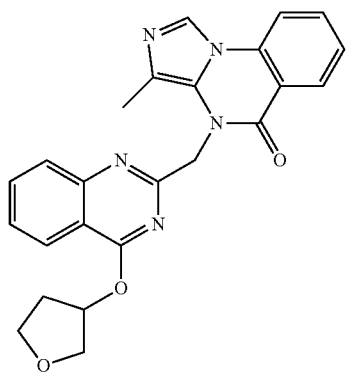<br><br>1100 |
| Amine used (source) | Products obtained from 3a1-32 |
|---|---|
| 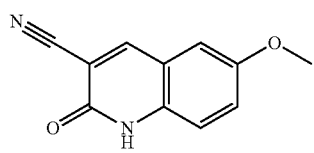<br><br>3a1-32<br>(see example 25) | 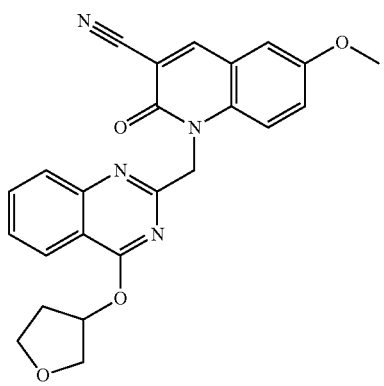<br><br>1105 |

-continued
| Amine used (supplier) | Products obtained from 3a1-33 |
|---|---|
| 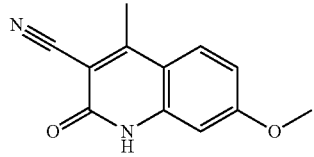
3a1-33
(see example 26) | 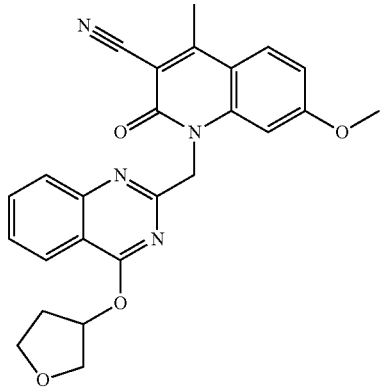
1107
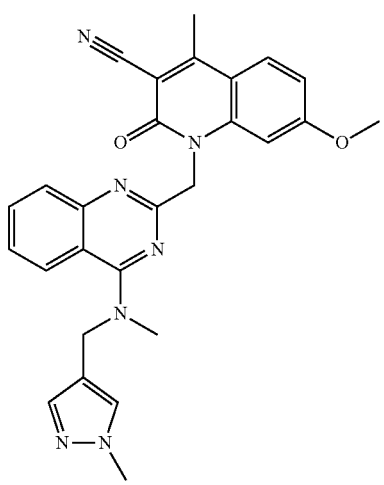
1101 |
| Amine used (source) | Products obtained from 3a1-34 |
|---|---|
| 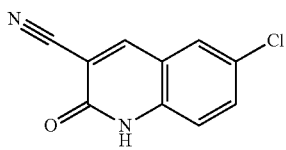
3a1-34
(see example 27) | 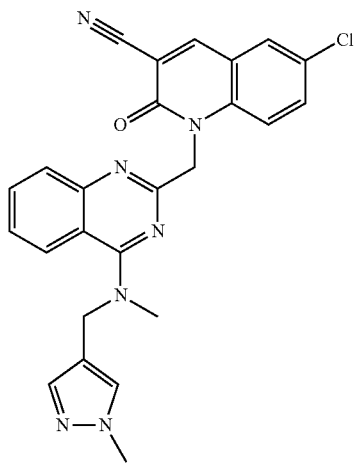
1102 |

-continued
| Amine used (source) | Products obtained from 3a1-35 |
|---|---|
| 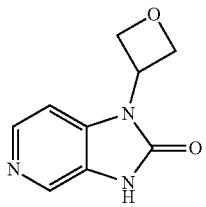<br>3a1-35<br>(see example 28) | 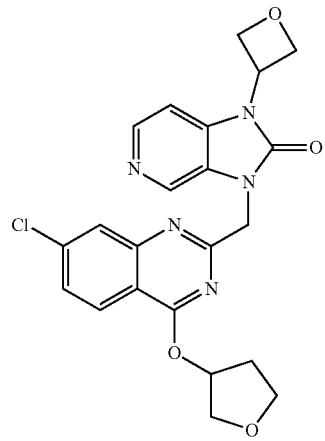<br>1072 |
| Amine used (source) | Products obtained from 3a1-36 |
|---|---|
| 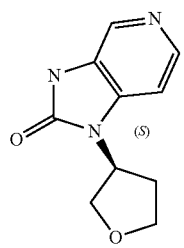<br>3a1-36<br>(see example 29) | 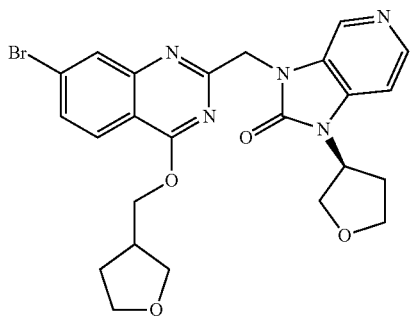<br>1055 |
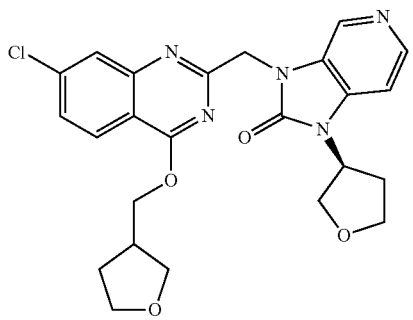
1094

-continued
| Amine used (source) | Products obtained from 3a1-37 |
|---|---|
| 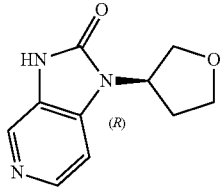<br>3a1-37<br>(see example 30) | 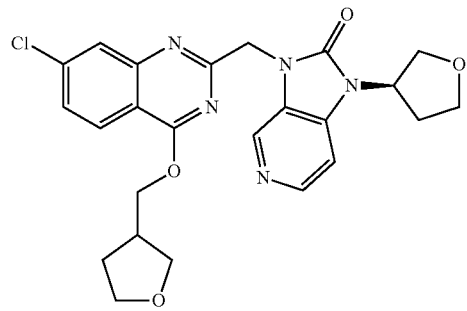<br>1093 |
| Amine used (source) | Products obtained from 3a1-38 |
|---|---|
| 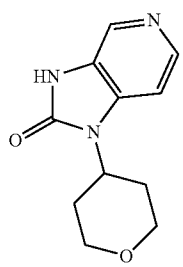<br>3a1-38<br>(see example 31) | 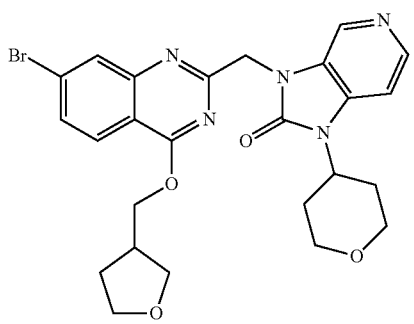<br>1056 |
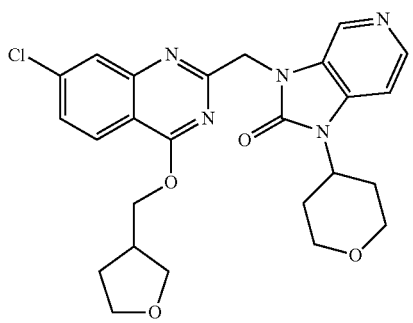
1095

-continued
| Amine used (source) | Products obtained from 3a1-39 |
|---|---|
| 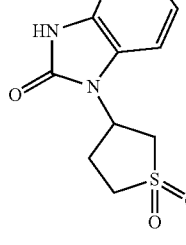<br>3a1-39<br>(see example 32) | 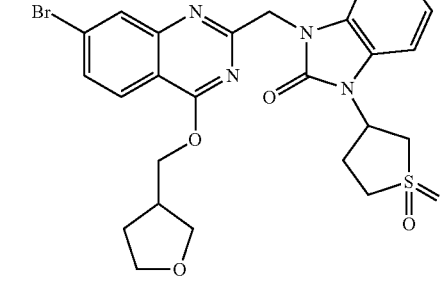<br>1057<br><br>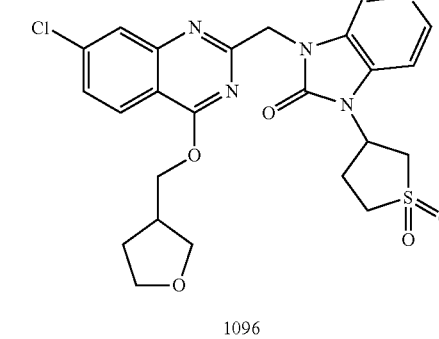<br>1096 |
| Amine used (supplier) | Products obtained from 3a1-40 |
|---|---|
| 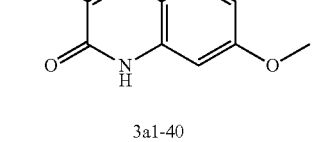<br>3a1-40<br>(Otava) | 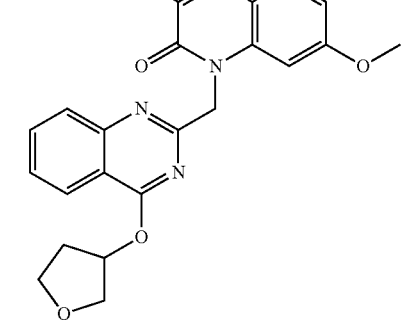<br>1106 |

-continued
| Amine used (supplier) | Products obtained from 3a1-41 |
|---|---|
| 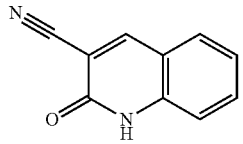<br>3a1-41<br>(Bionet) | 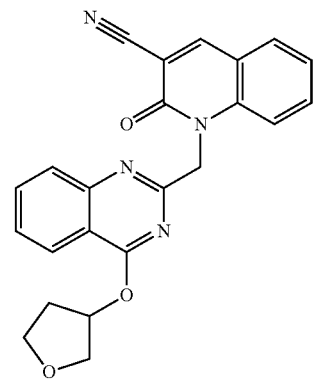<br>1108<br><br>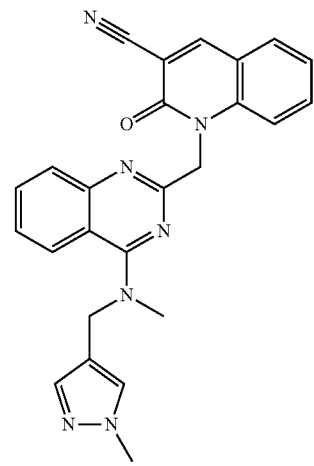<br>1103 |
| Amine used (source) | Products obtained from 4a1-1 |
|---|---|
| 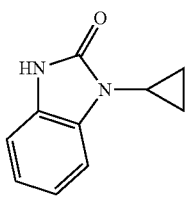<br>4a1-1<br>(see example 11) | 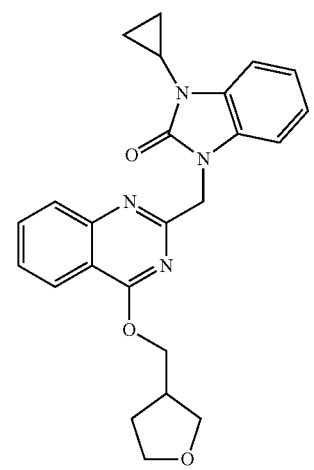 [SMILES: Cn1cncc1COc1nc(Cn2c(=O)n(C3CC3)c3ccccc32)nc2ccccc12]<br>1014 |

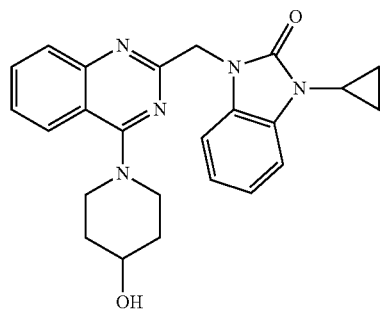
1003
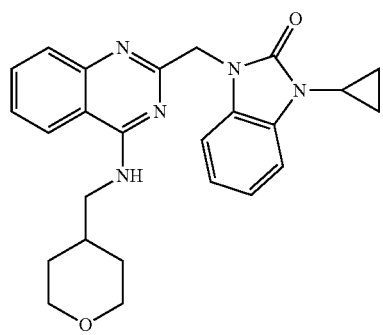
1004
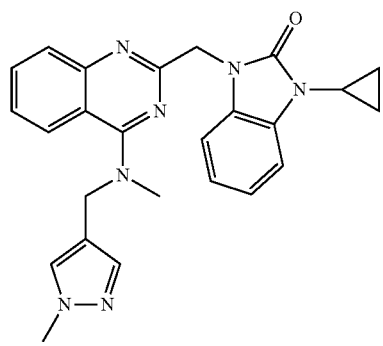
1005
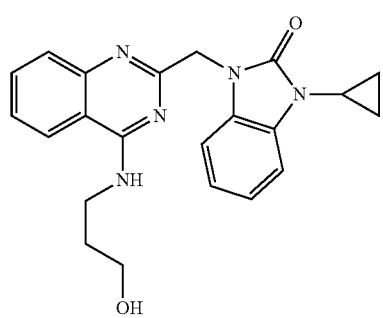
1006

Example 4

(General Procedure D): Preparation of Intermediate 4a2

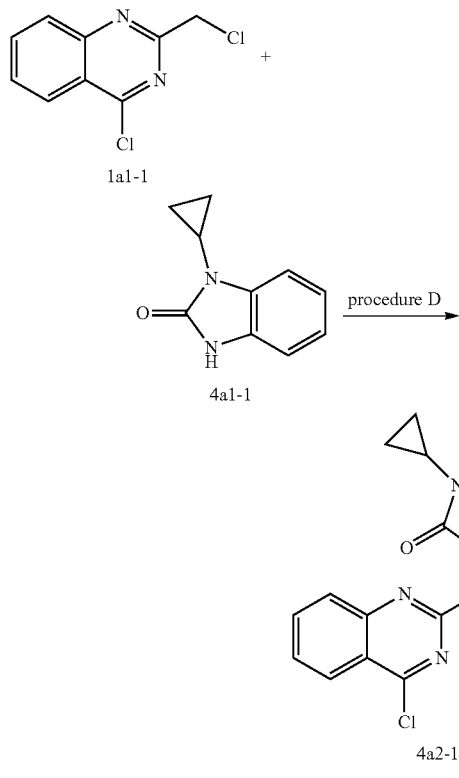

Example 5

(General Procedure E): Preparation of Intermediate 5a1

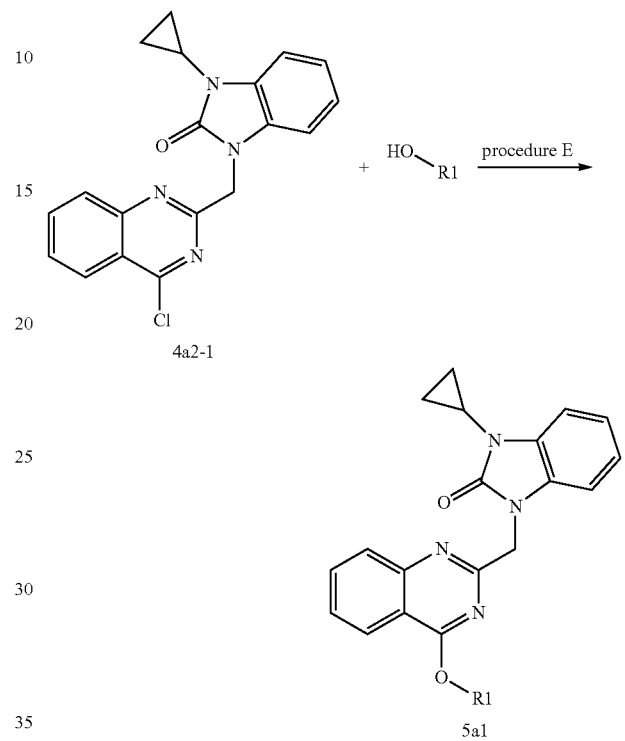

To a solution of the cyclic urea 4a1-1 (409 mg, 2.35 mmol) in DMA (3 mL) is added KOH (0.18 mL, 12.7 N). The reaction is stirred at RT for 10 min and the chloride 1a1-1 (Bioblocks, 500 mg, 2.35 mmol) is added as a solid to the mixture. The reaction is stirred at RT for 2 h. The mixture is diluted with EtOAc and water. The layers are separated and the aqueous layer is extracted twice with EtOAc. The organic layers are combined, washed twice with water, brine, dried over MgSO$_4$, filtered and concentrated. Purification by flash chromatography using EtOAc/hexane affords compound 4a2-1.

To a suspension of the reagent 4a2-1 (1 equivalent) in a mixture of THF:iPrOH (10:1, 0.02-0.1 mmol) or iPrOH (0.02-0.1 mmol) is added 2a2 (5 equivalents) followed by Et$_3$N (5 equivalents). The reaction mixture is stirred at 75° C. overnight and the solvent is then evaporated. The residue obtained is purified by mass directed purification on reverse phase HPLC column and lyophilized.

| Alcohol used | no | Alcohol source | Final product | Cmpd # |
|---|---|---|---|---|
| HO~~~OH | 2a2-1 | Aldrich | [structure] | 1069 |

-continued
| Alcohol used | no | Alcohol source | Final product | Cmpd # |
|---|---|---|---|---|
| 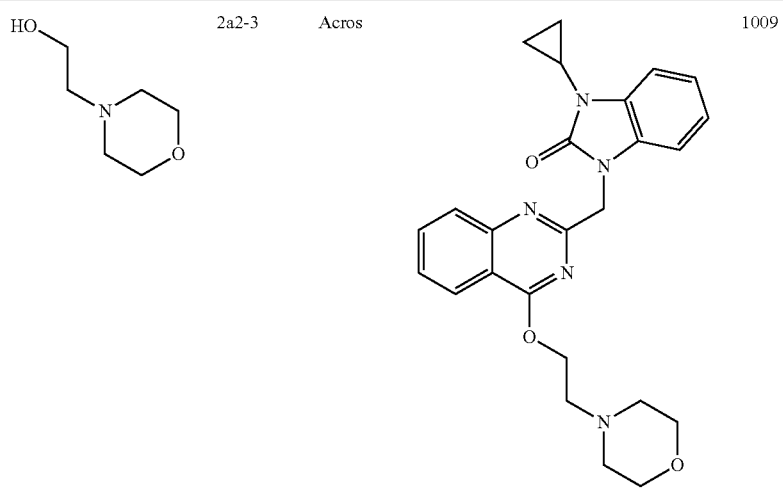 | 2a2-3 | Acros | | 1009 |
| 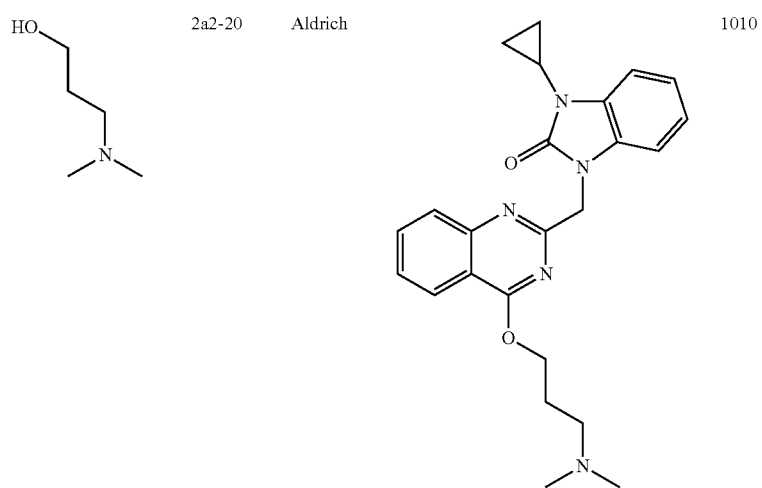 | 2a2-20 | Aldrich | | 1010 |
| 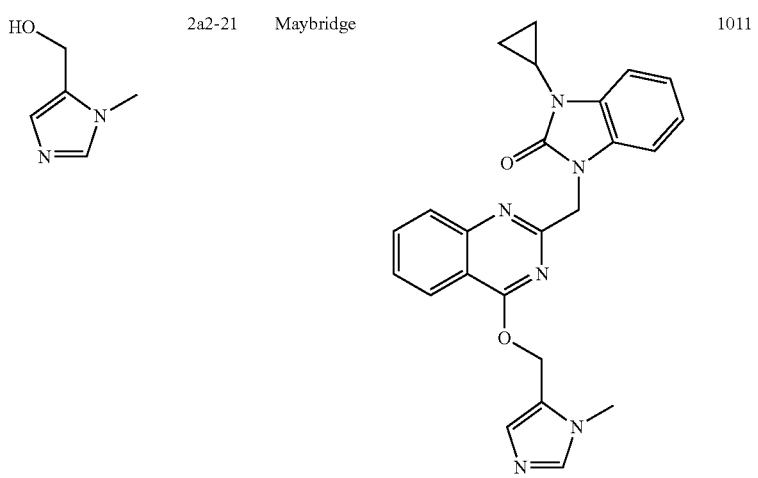 | 2a2-21 | Maybridge | | 1011 |

-continued

| Alcohol used | no | Alcohol source | Final product | Cmpd # |
|---|---|---|---|---|
| (HO-CH2-pyridin-3-yl) | 2a2-5 | Aldrich | (structure) | 1012 |
| (HO-CH2CH2-(1-methylpyrrolidin-2-yl)) | 2a2-22 | Acros | (structure) | 1013 |

Example 6

Preparation of Intermediate 3a1-14

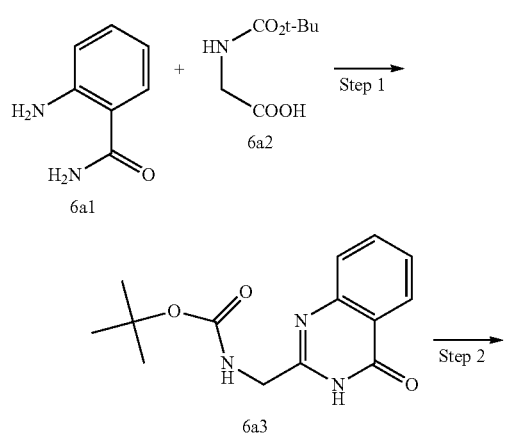

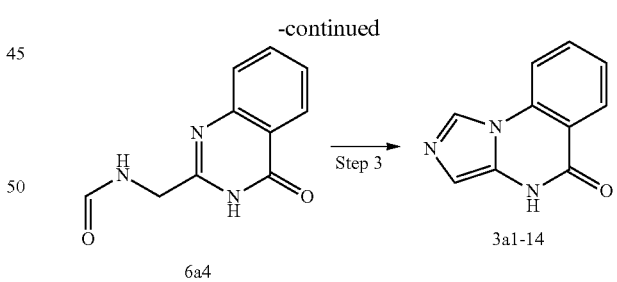

Step 1

In a sealed vial, isobutylchloroformate (2 mmol) is added to a cold solution (−15° C.) of 6a2 (2 mmol) (Aldrich) and N-methylmorpholine (2 mmol) in THF (10 mL). The mixture is stirred at −15° C. for 30 min. Compound 6a1 (2 mmol) (Aldrich) is then added and the sealed vial is irradiated in a microwave at 120° C. for 20 min (100 W). After cooling to RT, a solution of 2M EtONa in EtOH (2 mL) is added to the mixture and is heated in the microwave at 120° C. for 10 min (100 W). After evaporation under reduced pressure, the resulting residue is hydrolyzed with 1M HCl (10 mL) until a precipitate forms. The precipitate is recrystallized from EtOH to afford compound 6a3.

Step 2

A solution of 6a3 (1 mmol) and TFA (2.5 mL) in DCM (20 mL) is refluxed for 2 h. The solvent is concentrated in vacuo, then Et₃N (2 mL) and ethyl formate (10 mL) are added. The resulting mixture is refluxed overnight. Trituration of the residue after solvent evaporation with water provides a solid which is recrystallized from EtOH to afford intermediate 6a4.

Step 3

A mixture of intermediate 6a4 (1 mmol) and PPA (3 g/mmol) in xylene (5 mL) is irradiated in a microwave at 120° C. for 15 min (20 W). The xylene is decanted and the remaining residue is washed twice with petroleum ether and is dissolved in water. The aqueous solution is filtrated and dropwise addition of 30% NaOH leads to precipitation of a product which is removed by filtration and recrystallized from EtOH to afford compound 3a1-14.

Example 7

Preparation of Intermediate 3a1-28

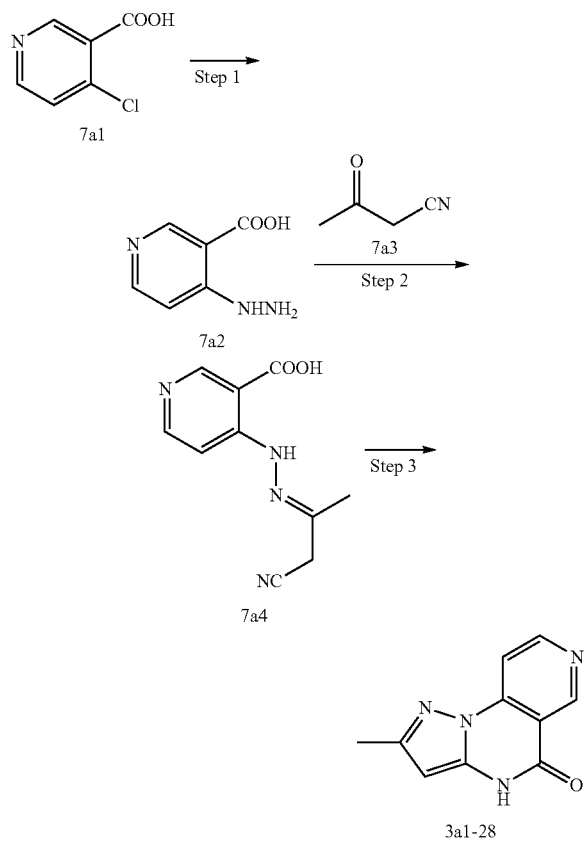

Step 1

A solution of the 7a1 (260 mg, 1.7 mmol) (Matrix) in hydrazine hydrate (2.2 mL) is heated at 100° C. for 4 h. After evaporation in vacuo, the residue is dissolved in water (~2.5 mL), then acidified with concentrated HCl to pH 2. The precipitate is filtrated, washed with EtOH and ether to afford intermediate 7a2.

Step 2

Intermediate 7a2 (160 mg, 1 mmol) is suspended in water (2 mL). Concentrated HCl (0.2 mL) and the keto-nitrile 7a3 (86 mg, 1 mmol) (J&W Pharmalab) are added to this suspension. The mixture is stirred at RT for 30 min, and then heated to reflux for 2 h. The solid in suspension is filtered, and then washed with ether to afford some 7a4. The filtrate is purified by mass directed purification on reverse phase HPLC column to afford compound 7a4 which is combined with the first crop.

Step 3

To a solution of intermediate 7a4 (65 mg, 0.3 mmol) in DMF (1.5 mL) is added 4N HCl/dioxane (0.3 mL, 0.9 mmol). The mixture is heated at 130° C. overnight. The mixture is cooled and purified by mass directed purification on reverse phase HPLC column to afford compound 3a1-28.

Example 8

Preparation of Intermediate 3a1-13

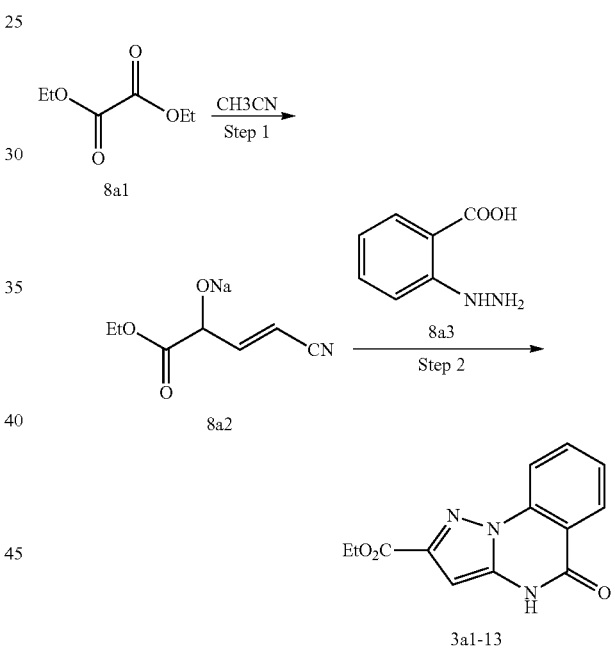

Step 1

To a solution of EtONa (5.1 g, 75.3 mmol) in EtOH (60 mL) is added 8a1 diethyloxalate (10 g, 68.4 mmol) and the mixture is stirred at 60° C. for 30 min. ACN (2.5 mL) is added to the mixture and the reaction mixture is refluxed for 5 h. The reaction mixture is cooled to RT and the precipitated product is collected by filtration and washed with cold ether to afford intermediate 8a2 which is used directly in the next step.

Step 2

A suspension of 8a3 (7 g, 46 mmol) and 8a2 (6.7 g, 46 mmol) in ethanolic HCl (120 mL; HCl gas bubbled to EtOH) is refluxed overnight. The reaction mixture is cooled to RT and the precipitated product is collected by filtration. The solid is crystallized from ethyl acetate and EtOH to afford compound 3a1-13.

Example 9

Preparation of Intermediate 3a1-7

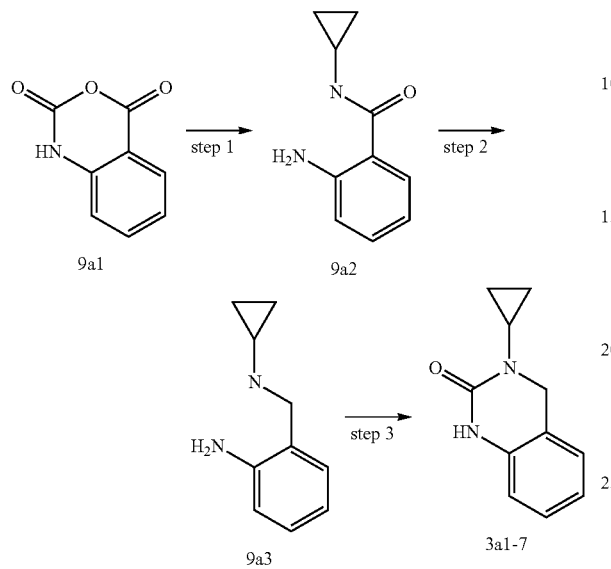

Step 1

To a stirred solution of 9a1 isatoic anhydride (10.0 g, 61.3 mmol) (Lancaster) in EtOH (100.0 mL) is added Et₃N (8.48 mL, 61.3 mmo). Cyclopropylamine (6.51 mL, 61.3 mmol) is added at such a rate that the reaction temperature does not rise above 30° C. After this addition, the reaction is heated to 70° C. for 16 h. The reaction mixture is cooled to RT and a precipitate is formed. The solid is collected by filtration and washed with diethyl ether. The solid is then stirred in diethyl ether for 1 h, filtered and washed with diethyl ether to give intermediate 9a2.

Step 2

To a stirred solution of lithium aluminium hydride (2.9 g, 76.7 mmol) in THF (77 mL) at 0° C. is added intermediate 9a2 (5.0 g, 28.4 mmol) in THF (60 mL) at such a rate that the reaction temperature does not rise above 10° C. After this addition, the reaction is heated at 60° C. for 16 h. The reaction is quenched with a 1N aqueous solution of NaOH. The mixture is filtered through celite, and the filtrate is washed with EtOAc and water. The aqueous layer is separated and extracted with EtOAc. The combined organic extracts are dried over sodium sulphate, filtered and concentrated in vacuo. The crude material is purified by flash chromatography (50:50 EtOAc/Petroleum ether) to afford intermediate 9a3.

Step 3

To a stirred solution of intermediate 9a3 (2.0 g, 12.3 mmol) in THF (22.0 mL) is added carbonyldiimidazole (3.0 g, 18.5 mmol) and the resulting mixture is stirred at RT overnight. The reaction mixture is concentrated in vacuo. The crude product is diluted with DCM and washed with water. The organic layer is washed with a 1M aqueous solution of HCl, dried over sodium sulphate, filtered and concentrated. The crude material is purified by flash chromatography to afford intermediate 3a1-7.

Example 10

Preparation of Intermediate 3a1-3

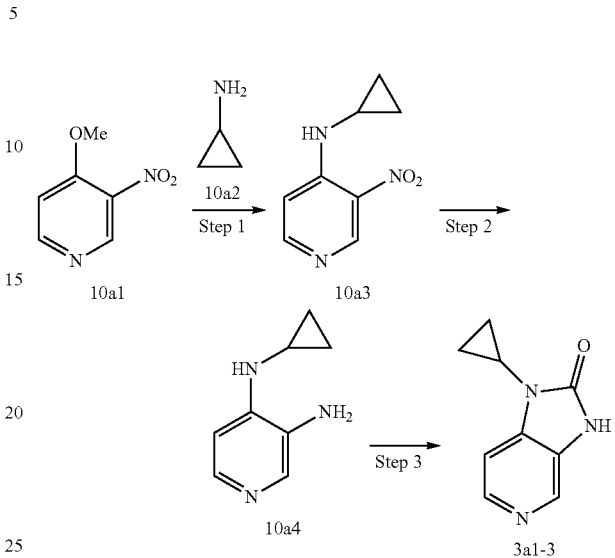

Step 1

A solution of 10a1 (4 g, 26 mmol) (Molekula), cyclopropylamine 10a2 (4.5 mL, 64.9 mmol) (Avra) and N,N-diisopropylethylamine (8.9 mL, 54 mmol) in EtOH (15 mL) is refluxed for 3 h. The reaction mixture is cooled to 0° C. and the solid in suspension is collected by filtration. The solid obtained is washed with cold EtOH to afford intermediate 10a3.

Step 2

A solution of intermediate 10a3 (3.8 g, 21 mmol) and Pd/C 10% (760 mg) in EtOH (32 mL) is stirred under hydrogen atmosphere at 50 psi for 2 h. The catalyst is filtrated through Celite. The filtrate is evaporated under reduced pressure to afford intermediate 10a4.

Step 3

To a solution of intermediate 10a4 (2 g, 13.4 mmol) in ACN (40 mL) at 0° C., is added carbonyldiimidazole (2.2 g, 13.4 mmol). The mixture is stirred at RT for 1 h. The precipitate is collected by filtration to afford intermediate 3a1-3.

Example 11

Preparation of Intermediate 4a1-1

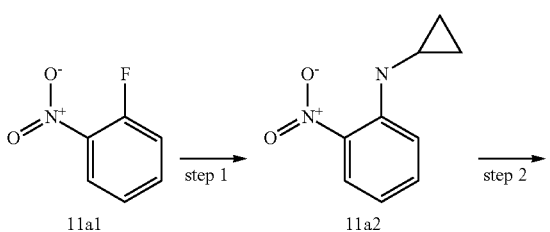

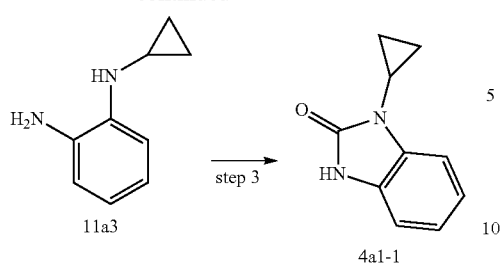

11a3

4a1-1

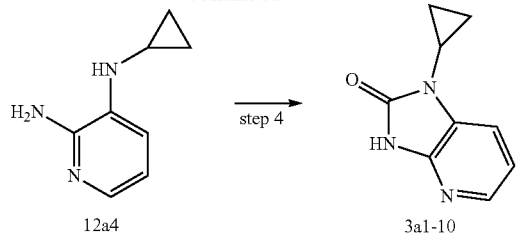

12a4

3a1-10

Step 1

To a stirred solution of reagent 11a1 (40.0 g, 283.5 mmol) (Avra) in THF (400 mL) is added cyclopropylamine (49.0 mL, 708.7 mmol). The resulting solution is refluxed overnight. The reaction is cooled to 0° C., diluted with water and DCM. The layers are separated and the organic extracts are washed with water, dried over $Na_2SO_4$, filtered and concentrated. The intermediate 11a2 is directly used in the next step.

Step 2

A solution of intermediate 11a2 (10.0 g, 56.1 mmol) and 10% Pd/C (2.4 g, 2.3 mmol) in EtOH (980 mL) is stirred for 2 h under a hydrogen pressure of 50 psi. The reaction mixture is filtered through celite and concentrated to afford intermediate 11a3.

Step 3

To a stirred solution of intermediate 11a3 (20.0 g, 135.0 mmol) in THF (400 mL) at 0° C. is added carbonyldiimidazole (43.8 g, 270.0 mmol) and the resulting mixture is warmed to RT and stirred overnight. The mixture is diluted with water and extracted with EtOAc. The organic layer is dried over sodium sulphate and concentrated in vacuo. The crude material is purified by flash chromatography to afford intermediate 4a1-1.

Example 12

Preparation of Intermediate 3a1-10

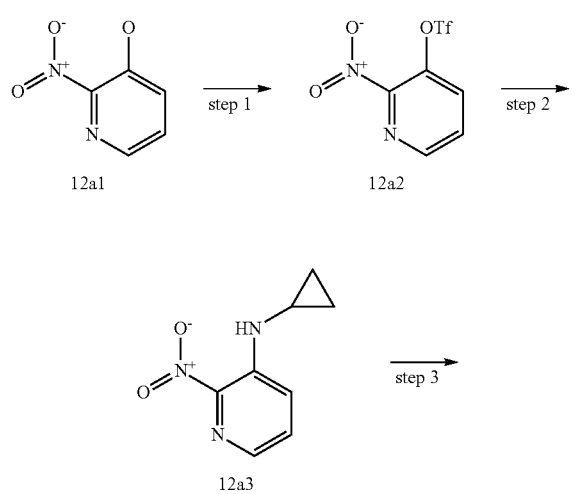

Step 1

To a stirred solution of reagent 12a1 (55.0 g, 393 mmol) (Aldrich) in DCM (825.0 mL) is added $Et_3N$ (81.3 mL, 583.3 mmol) and triflic anhydride (80.3 mL, 477.3 mmol) at 0° C. The reaction mixture is stirred for 2 h at RT. The suspension is diluted with water and extracted with DCM. The organic layer is dried over $Na_2SO_4$, filtered, concentrated and purified by flash chromatography to afford intermediate 12a2.

Step 2

To a stirred solution of intermediate 12a2 (5.0 g, 19.0 mmol) in toluene (50.0 mL) is added cyclopropylamine (2.3 mL, 33.2 mmol). The reaction mixture is stirred for 1 h at 90° C. The suspension is diluted with water and extracted with DCM. The organic layer is dried over $Na_2SO_4$, filtered, concentrated and purified by flash chromatography to afford intermediate 12a3.

Step 3

A solution of 12a3 (30.0 g, 167.0 mmol) and 10% Pd/C (6.5 g, 6.1 mmol) in EtOH (567 mL) is stirred for 1 h under a hydrogen pressure of 50 psi. The reaction mixture is filtered through celite, concentrated and purified by flash chromatography to afford intermediate 12a4.

Step 4

To a stirred solution of intermediate 12a4 (20.0 g, 135.0 mmol) in THF (625 mL) at 0° C. is added carbonyldiimidazole (45.7 g, 281.5 mmol). The resulting reaction mixture is warmed to RT and stirred overnight. The reaction mixture is diluted with water and extracted with EtOAc. The organic layer is dried over sodium sulphate and concentrated under reduced pressure. The crude material is washed with EtOAc and cooled ACN to give intermediate 3a1-10.

Example 13

(General Method for Tricyclic Lactam): Preparation of Intermediates 3a1-26 and 3a1-8, 3a1-15, 3a1-17, 3a1-21, 3a1-25, 3a1-27

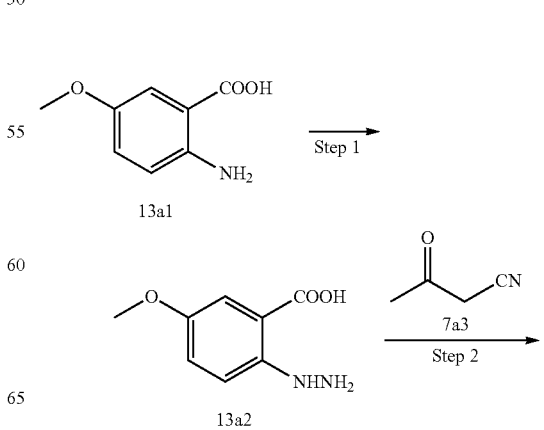

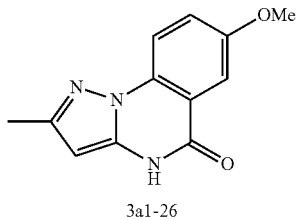

3a1-26

Step 1

To a solution of the 13a1 (1 g, 6 mmol) (Acros) in concentrated HCl (10 mL) at 0 to −10° C. is added a solution of NaNO$_2$ (0.45 g, 6.5 mmol) in water (1 mL). The reaction mixture is stirred at 0° C. for 1 h. Then a solution of SnCl$_2$-2H$_2$O (3 g, 23.8 mmol) in concentrated HCl (5 mL) is added. The reaction mixture is allowed to warm to RT and stirred for 1 h. The solid in suspension is filtered, then is washed with water and EtOAc or Et$_2$O to afford intermediate 13a2 which is used as such in the next step.

Step 2

A solution of the intermediate 13a2 (200 mg, 0.91 mmol) in 2M HCl (1.5 mL) and the keto-nitrile 7a3 (200 mg, 2.4 mmol) (J&W Pharmalab) is refluxed for 2 h. The solid in suspension is filtered, and then is washed with water and EtOAc to afford intermediate 3a1-26 which is used as such in the next step or the reaction mixture is purified by mass directed purification on reverse phase HPLC column.

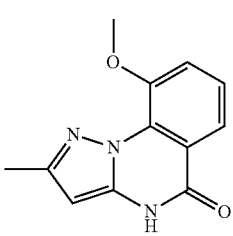

3a1-25

3a1-27

Intermediates 3a1-8, 3a1-15, 3a1-21, 3a1-25 and 3a1-27 are prepared with an analogous synthetic pathway using a keto-nitrile and an aryl or heteroaryl hydrazine (step 2) obtained from diazotation of the corresponding aniline or heretroaromatic amine (step 1). Intermediate 3a1-17 is prepared using an analogous pathway using the ethyl keto-nitrile (Matrix) and the commercially available 2-hydrazino-benzoic acid (Alfa).

Example 14

Preparation of Intermediate 3a1-16

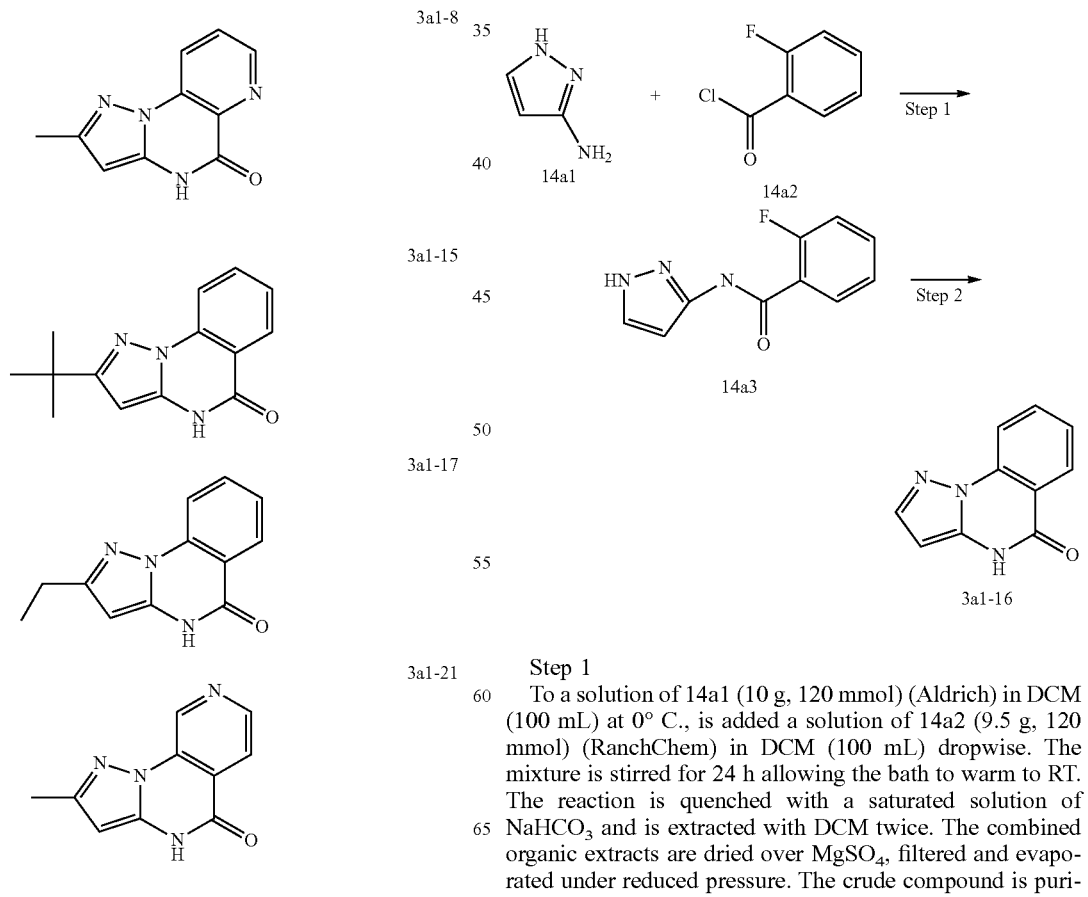

Step 1

To a solution of 14a1 (10 g, 120 mmol) (Aldrich) in DCM (100 mL) at 0° C., is added a solution of 14a2 (9.5 g, 120 mmol) (RanchChem) in DCM (100 mL) dropwise. The mixture is stirred for 24 h allowing the bath to warm to RT. The reaction is quenched with a saturated solution of NaHCO$_3$ and is extracted with DCM twice. The combined organic extracts are dried over MgSO$_4$, filtered and evaporated under reduced pressure. The crude compound is purified by flash chromatography to afford intermediate 14a3 which is used as such in the next step.

Step 2

A solution of the 14a3 (3 g, 15 mmol) and K$_2$CO$_3$ (4 g, 29 mmol) in DMF (80 mL) is heated at 140° C. for 3 h. The solvent is concentrated in vacuo and then purified by flash chromatography to afford intermediate 3a1-16 which is used as such in the next step.

Example 15

Preparation of Compound 2a1-2

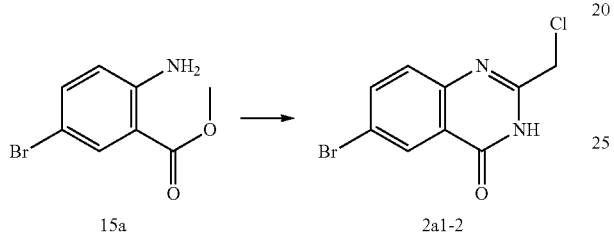

15a            2a1-2

In a flask, anthranilic ester 15a (Lancaster, 9.50 g, 41.3 mmol) and chloroacetonitrile (4.68 g, 61.9 mmol) are mixed and a HCl solution (4M in dioxane, 27.9 mL) is added under stirring. The mixture is heated at 50° C. overnight and is cooled to RT. Diethyl ether is added and the mixture is stirred, sonicated and filtered. The collected solid is taken up in water, basified with NaOH 5M or NaHCO$_3$ until solubilized (sonication and vigorous stirring are required). The solution is neutralized back with HCl 2M, under stirring. When the pH is about 7, the suspension is filtered on filter paper, washed with water and then washed with hexanes to give 2a1-2.

Example 16

Preparation of Compound 2a1-3

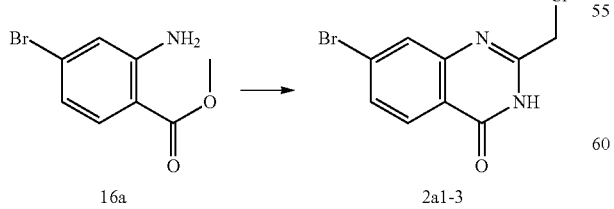

16a            2a1-3

Compound 2a1-3 is prepared analogously to the procedure described in Example 15, but using methyl 2-amino-4-bromobenzoate 16a (Apollo) in place of 15a.

Example 17

Preparation of Compound 2a1-4

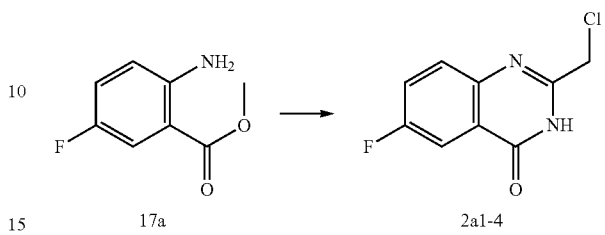

17a            2a1-4

Compound 2a1-4 is prepared analogously to the procedure described in Example 15, but using methyl 2-amino-5-fluorobenzoate 17a (Aldrich) replacing 15a.

Example 18

Preparation of Compound 2a1-5

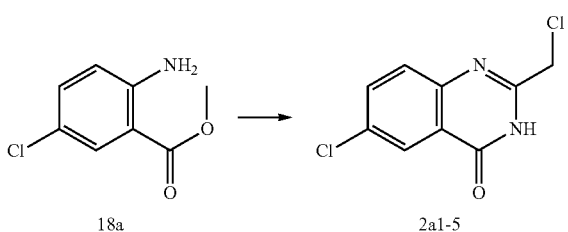

18a            2a1-5

Compound 2a1-5 is prepared analogously to the procedure described in Example 15, but with methyl 2-amino-5-chlorobenzoate 18a (Lancaster) replacing 15a.

Example 19

Preparation of Compound 2a1-6

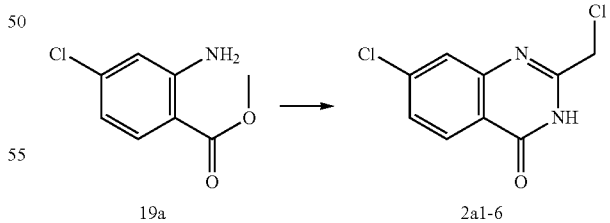

19a            2a1-6

In a flask, anthranilic ester 19a (Lancaster, 12.0 g, 64.7 mmol) and chloroacetonitrile (6.35 g, 84.0 mmol) are mixed and a HCl solution (4M in dioxane, 43.6 mL) is added under stirring. The mixture is heated at 50° C. overnight and is cooled to RT. The solvent is removed in vacuo, the residue is suspended in water and the mixture sonicated. The solid is filtered, washed with water several times and the resulting product is dried under high vacuum to afford 2a1-6.

Example 20

Preparation of Compound 2a1-7

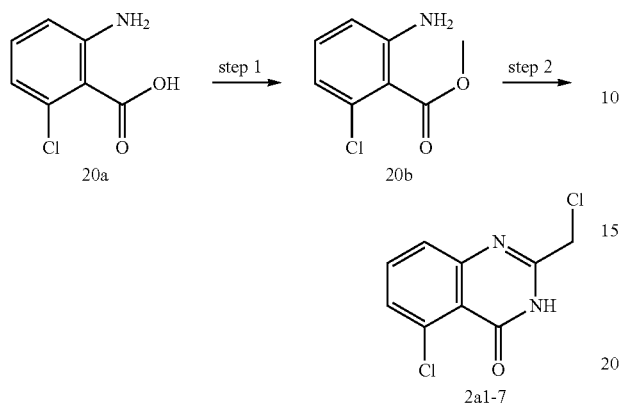

Step 1

2-amino-6-chlorobenzoic acid 20a (Aldrich, 5 g; 29 mmol) is dissolved in toluene/MeOH (40 mL)/(10 mL) and a solution of (trimethylsilyl)diazomethane (2 M in Et$_2$O; 16 mL) is added at RT. The solution is stirred for 30 min at RT and quenched with few drops of AcOH. The solution is diluted with EtOAc, washed with water, saturated solution of NaCl, dried over Na$_2$SO$_4$ and concentrated to afford 20b.

Step 2

In a flask, anthranilic ester 20b (Lancaster, 3.44 g, 18.5 mmol) and chloroacetonitrile (1.65 ml, 25.9 mmol) are mixed and a HCl solution (4M in dioxane, 12.5 mL) is added under stirring. The mixture is heated at 50° C. overnight and is cooled to RT. The solvent is removed in vacuo, the residue is suspended in water and the mixture sonicated. The solid is filtered, washed with water several times and the product dried under high vacuum to afford 2a1-7.

Example 21

Preparation of Compound 2a1-8

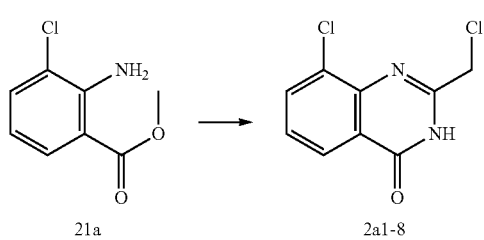

In a flask, anthranilic ester 21a (Combi-Blocks, 5.00 g, 26.9 mmol) and chloroacetonitrile (2.38 ml, 37.5 mmol) are mixed and a HCl solution (4M in dioxane, 18.2 mL) is added under stirring. The mixture is heated at 50° C. overnight and is cooled to RT. The solvent is removed in vacuo, the residue is suspended in water and the mixture sonicated. The solid is filtered, washed with water several times, followed by Et$_2$O and the product dried under high vacuum to afford 2a1-8.

Example 22

Preparation of Compound 1a1-2

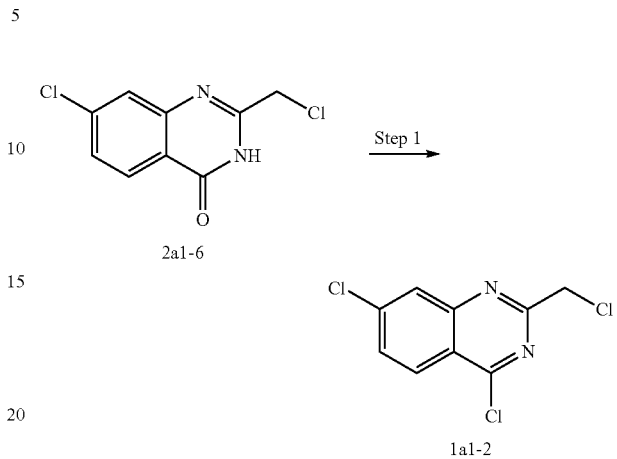

Intermediate 2a1-6 (901 mg, 3.93 mmol) is dissolved in chloroform (40 mL). 2,6-lutidine (978 µl, 8.40 mmol) and phosphoryl chloride (900 µl, 9.83 mmol) are added in succession. The reaction mixture is heated to 80° C. (reflux) for 16 h. The reaction mixture is concentrated under reduced pressure. The residue is taken up in DCM and washed with water. The aqueous layer is extracted twice with DCM. The combined organic layers are washed with brine, dried over magnesium sulfate, filtered and evaporated under reduced pressure. This procedure afforded Intermediate 1a1-2.

Example 23

Preparation of Compound 3a1-30

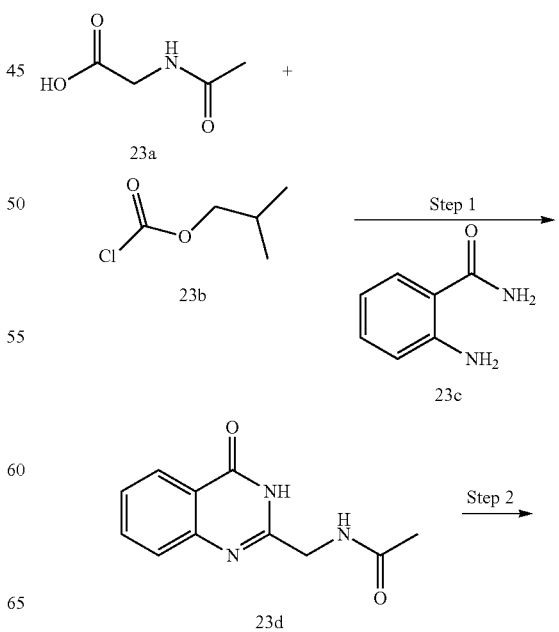

-continued

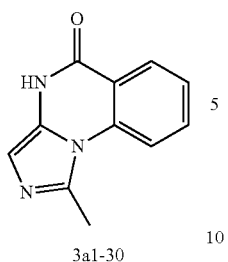

3a1-30

Step 1

To a suspension of N-acetylaminoacetic acid 23a (Aldrich, 502 mg, 3.67 mmol) and N-methylmorpholine (0.40 mL, 3.67 mmol) in THF (15 mL) at −15° C., is added isobutyl chloroformate (Aldrich, 0.41 mL, 3.67 mmol). After stirring for 30 min, 2-aminobenzamide 23c (Aldrich, 500 mg, 3.67 mmol) is added and the mixture heated in a microwave at 120° C. during 20 min. NaOEt (Lancaster, 4 mL, 21% in EtOH) is added and the mixture is heated in a microwave at 120° C. for 10 min. The mixture is concentrated, suspended in $H_2O$, neutralized with HCl (1N), filtered and rinsed with hexanes to give intermediate 23d.

Step 2

In a sealed tube, PPA (3.0 g) and xylene (10 mL) are heated at 120° C. and intermediate 23d (440 mg, 2.03 mmol) is added. The tube is sealed and heated at 120° C. overnight. The xylene phase is removed and the residue is washed with toluene. The resulting solid is dissolved in $H_2O$ and NaOH (10N) is added until precipitation. The suspension is filtered, rinsed with $H_2O$, $Et_2O$ and dried to give compound 3a1-30.

Example 24

Preparation of Compound 3a1-31

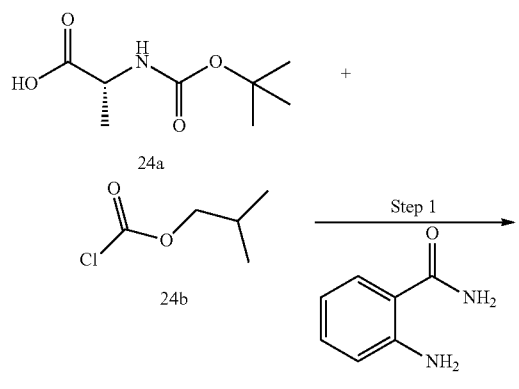

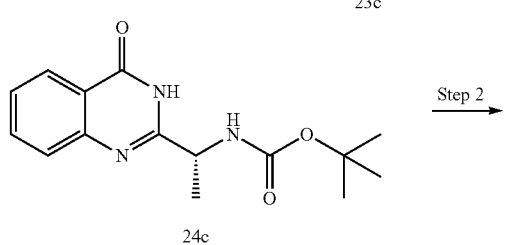

-continued

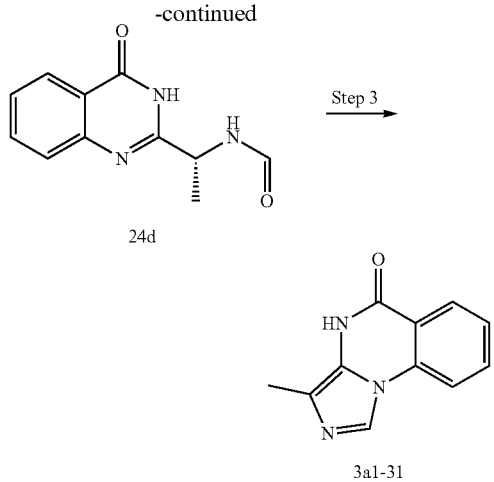

Step 1

To a suspension of (R)-2-tert-butoxycarbonylaminopropionic acid 24a (Bachem, 695 mg, 3.67 mmol) and N-methylmorpholine (0.40 mL, 3.67 mmol) in THF (15 mL) at −15° C., is added isobutyl chloroformate (Aldrich, 0.41 mL, 3.67 mmol). After stirring for 30 min., 2-aminobenzamide 23c (Aldrich, 500 mg, 3.67 mmol) is added and the mixture heated in a microwave at 120° C. for 20 min. NaOEt (Lancaster, 4 mL, 21% in EtOH) is added and the mixture is heated in a microwave at 120° C. for 10 min. The mixture is concentrated, suspended in $H_2O$, neutralized with HCl (1N), filtered and rinsed with hexanes to give intermediate 24c.

Step 2

To a solution of intermediate 24c (350 mg, 1.21 mmol) in DCM (10 mL), is added TFA (3 mL) and the solution is stirred at RT during 15 min. The mixture is concentrated, $Et_3N$ (2 mL, 14.3 mmol) and ethyl formate (10 mL, 123 mol) are added and the solution is refluxed overnight. The mixture is concentrated, the residue triturated with $H_2O$ and filtered to give intermediate 24d.

Step 3

In a sealed tube, PPA (2.0 g) and xylene (5 mL) are heated at 120° C. and intermediate 24d (178 mg, 0.819 mmol) is added. The tube is sealed and heated at 120° C. overnight. The xylene phase is removed and the residue is washed with toluene. The resulting residue is dissolved in $H_2O$ and NaOH (10N) is added until precipitation. The obtained residue is purified by flash chromatography using $CH_2Cl_2$/MeOH to afford compound 3a1-31.

Example 25

Preparation of Compound 3a1-32

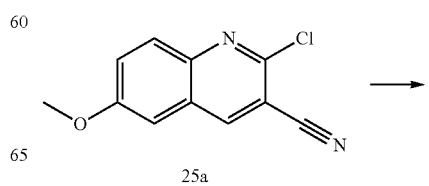

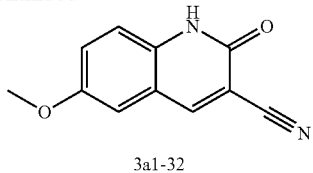

3a1-32

To a stirred solution of 2-chloro-6-methoxyquinoline-3-carbonitrile 25a (Bio-Blocks, 3.5 g, 16.1 mmol) in concentrated HCl (260 mL) is added MeOH (130 mL) and the reaction mixture is refluxed for 4 h. The reaction mixture is cooled and diluted with ethyl acetate. Ice water is added and the mixture is basified with saturated $Na_2CO_3$ (until the pH reaches 9.0). The compound is extracted with ethyl acetate and the organic layer is separated and washed with brine. The organic layer is dried over sodium sulphate, filtered and concentrated under reduced pressure. The obtained solid is washed with EtOH, filtered and dried to afford compound 3a1-32.

Example 26

Preparation of Compound 3a1-33

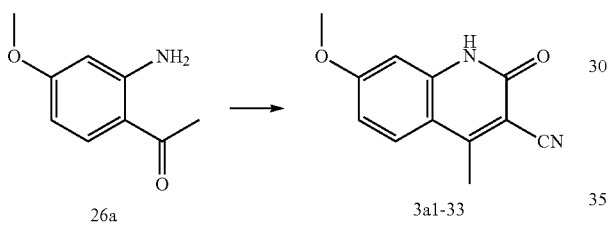

To 1-(2-amino-4-methoxy-phenyl)-ethanone 26a (JW-Pharmlab, 5.0 g, 30.2 mmol), ethyl cyanoacetate (6.8 g, 60.4 mmol) and ammonium acetate (11.7 g, 151.2 mmol) are added and heated under reflux for 5 h. The reaction mixture is cooled; the precipitate is filtered off and washed with EtOH to afford compound 3a1-33.

Example 27

Preparation of Compound 3a1-34

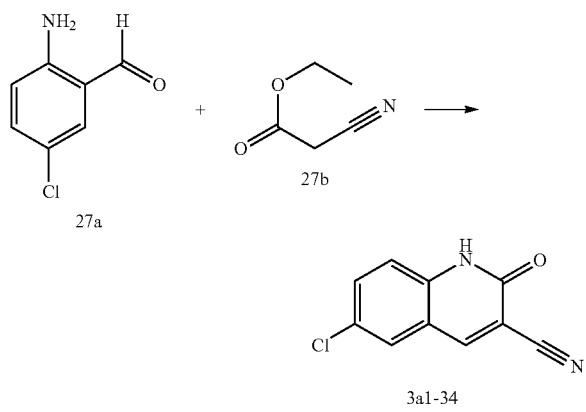

A solution of 2-amino-5-chlorobenzaldehyde 27a (Aldrich, 1.0 g, 6.43 mmol) in EtOH (13 mL) is treated with piperidine (0.32 mL, 3.21 mmol) then with ethyl cyanoacetate (Pfaltz-Bauer, 2.05 mL, 19.3 mmol). The mixture is heated at 100° C. for 15 min, after which a solid precipitates. The mixture is cooled to RT then filtered and washed with EtOH to afford compound 3a1-34.

Example 28

Preparation of Compound 3a1-35

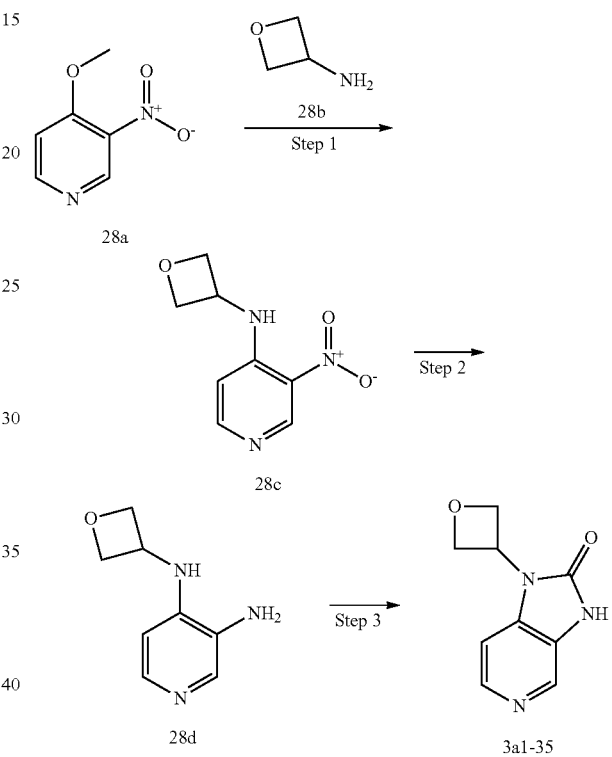

Step 1

A solution of 3-aminooxetane 28b (2.0 g, 27.4 mmol, Aldrich), 4-methoxy-3-nitropyridine 28a (8.43 g, 54.7 mmol, Combi-Blocks) and diisopropylethylamine (7.14 mL, 41.0 mmol) in EtOH (50 mL) is heated in a sealed tube for 16 h. The mixture is cooled to RT and concentrated under reduced pressure to half of the volume, and then cooled to 0° C. The resulting precipitate is filtered and triturated with hexane to afford compound 28c.

Step 2

Intermediate 28c (2.60 g, 13.3 mmol) is hydrogenated in anhydrous MeOH (50 mL) in the presence of 5% palladium on carbon (0.80 g) at 40 psi for 2.5 h at RT. The mixture is filtered through celite and the filter cake is washed with MeOH. The combined filtrate is concentrated under reduced pressure to afford compound 28d.

Step 3

Solid 1,1'-carbonyldiimidazole (1.47 g, 9.07 mmol) is added to a solution of 28d (1.0 g, 6.05 mmol) in anhydrous ACN (20 mL) and anhydrous THF (10 mL) at RT under $N_2$. The mixture is heated at reflux for 1.5 h. The solvents are evaporated under reduced pressure. The residue is dissolved in DCM (30 mL) and washed with water (20 mL). The aqueous phase is extracted with DCM, and the combined organic extracts are dried over sodium sulfate. After filtration and evaporation of the solvent under reduced pressure, the residue is purified by column chromatography on Biotage system (5:95 MeOH/EtOAc to 30:70 MeOH/EtOAc) to afford compound 3a1-35.

Example 29

Preparation of Compound 3a1-36

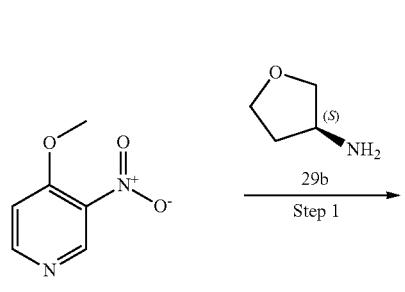

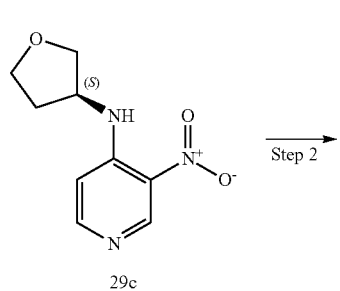

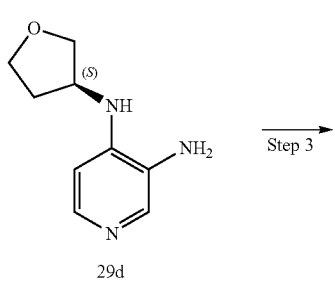

Intermediate 3a1-36 is made analogously to the procedure described for compound 3a1-35 (Example 28) using (S)-3-aminotetrahydrofuran (Small-Mol) 29b as the starting material in place of 28b.

Example 30

Preparation of Compound 3a1-37

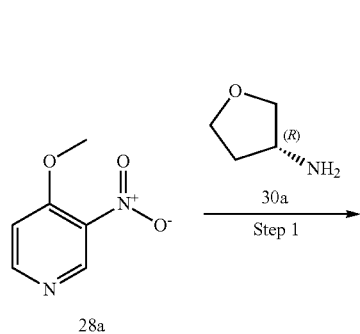

-continued

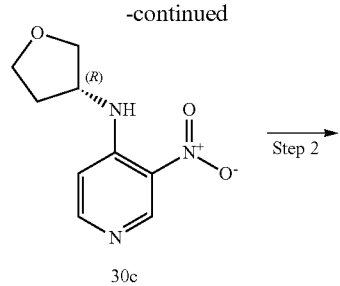

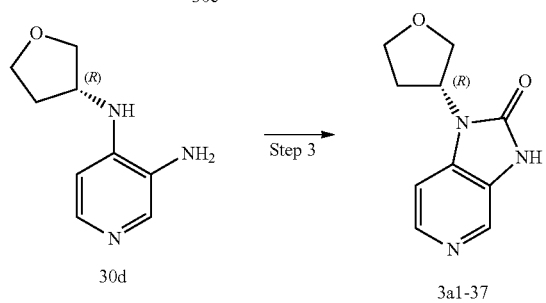

Intermediate 3a1-37 is made analogously to the procedure described for compound 3a1-35 (Example 28) using (R)-3-aminotetrahydrofuran (Small-Mol) 30a as starting material in place of 28b.

Example 31

Preparation of Compound 3a1-38

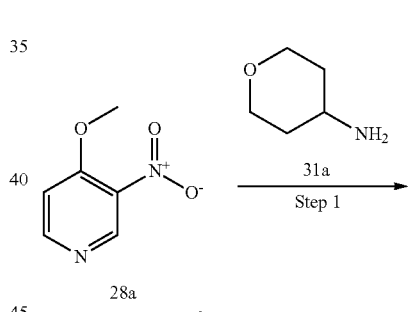

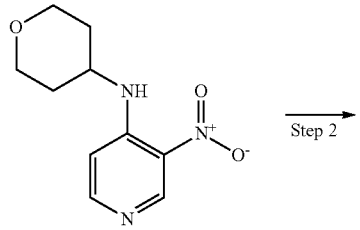

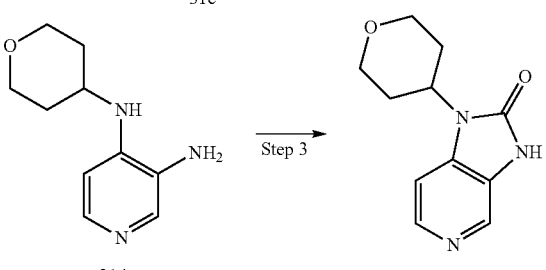

Intermediate 3a1-38 is made analogously to the procedure described for compound 3a1-35 (Example 28) using 4-aminotetrahydropyran (Combi-Blocks) 31a as the starting material in place of 28b.

Example 32

Preparation of Compound 3a1-39

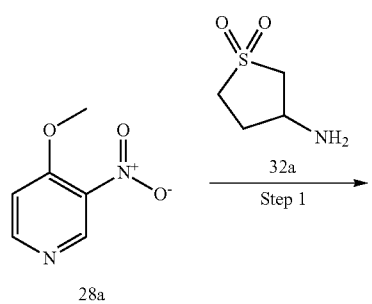

28a

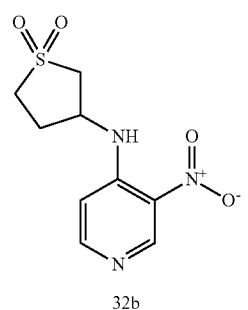

32b

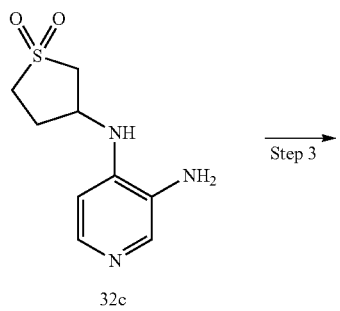

32c    3a1-39

Intermediate 3a1-39 is made analogously to the procedure described for compound 3a1-35 (Example 28) using 1,1-dioxidotetrahydrothien-3-ylamine 32a (Intermed) as the starting material in place of 28b.

Example 33

Preparation of Compound 1038

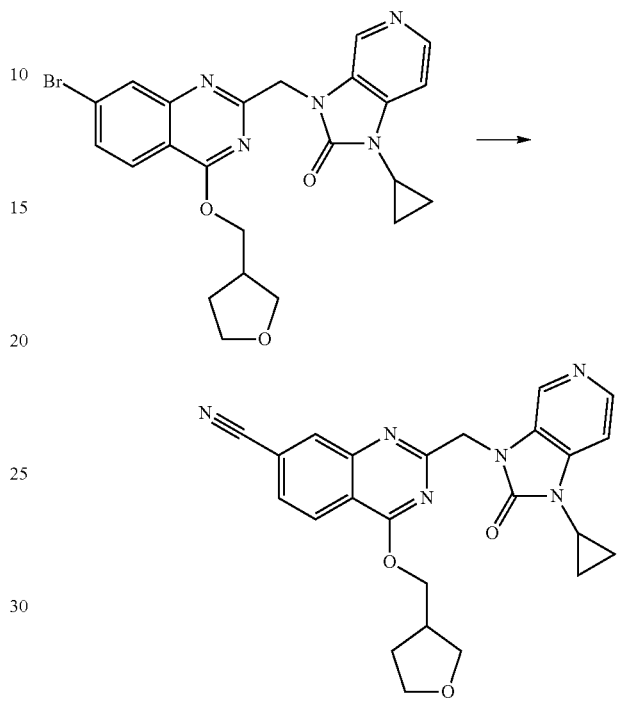

Compound 1032 (40 mg, 0.081 mmol), zinc cyanide (20 mg, 0.170 mmol) and palladium tetrakis(triphenylphosphine) are dissolved in DMA (0.80 mL). The reaction mixture is degassed with argon under sonication for 10 min and then heated to 125° C. using microwave irradiation for 30 min with stirring. The reaction mixture is diluted with acetic acid and purified using preparative HPLC. After lyophilization of the pure fractions Compound 1038 is obtained.

Example 34

Preparation of Compound 1036

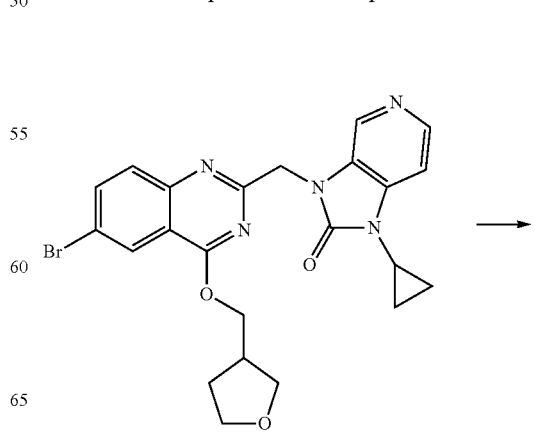

189
-continued

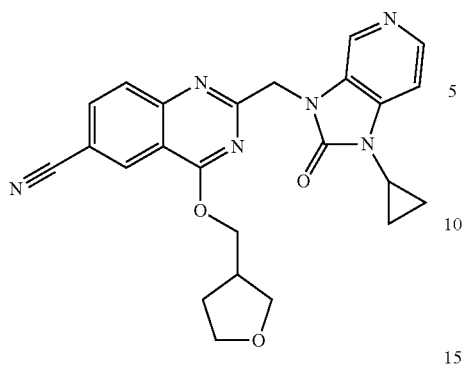

Compound 1036 is prepared using the method of Example 33, replacing 1032 with 1031.

Example 35

Preparation of Compound 1074

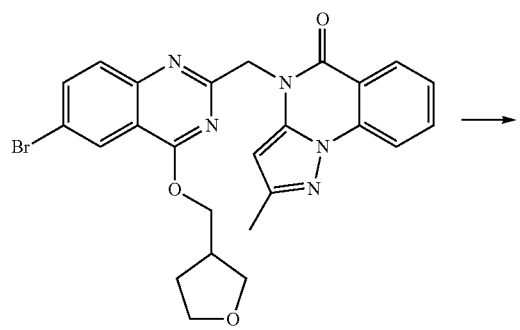

→

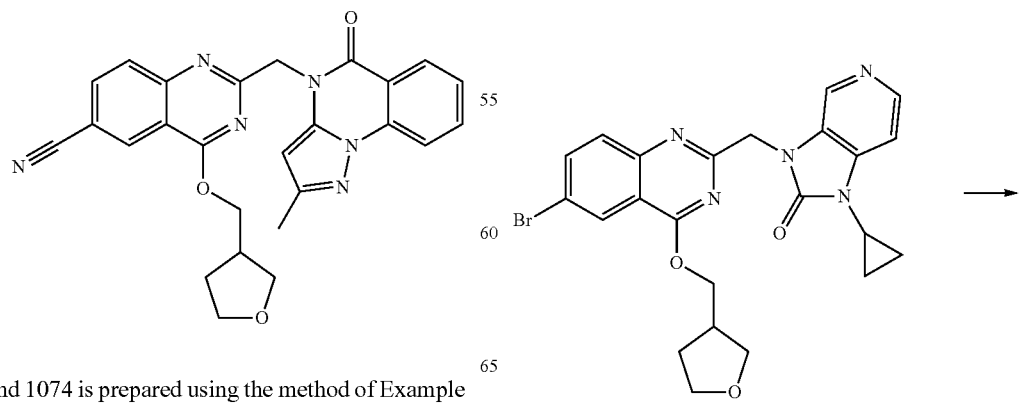

Compound 1074 is prepared using the method of Example 33, replacing 1032 with 1073.

190

Example 36

Preparation of Compound 1034

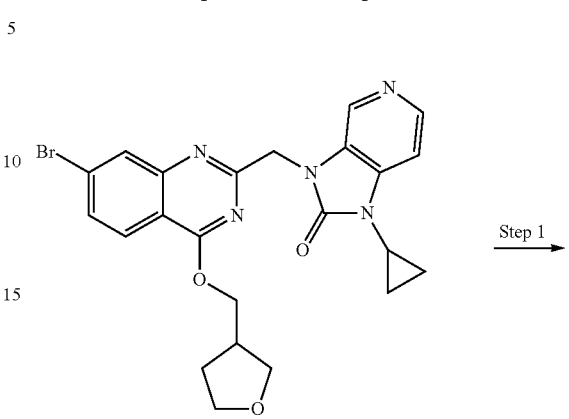

Step 1

Compound 1032 (40 mg, 0.081 mmol) and trans-dichlorobis(triphenylphosphine)palladium (Strem) (6.5 mg, 0.009 mmol) are suspended in argon degassed 1,4-dioxane (0.80 mL). To this mixture, cooled to 0° C., is added a trimethylaluminum solution (2M in hexanes, 0.185 mL, 0.37 mmol). The reaction mixture is heated to 60° C. with stirring. After 2 h, the reaction is quenched with a 1:1 mixture of acetic acid:MeOH and purified directly by preparative HPLC. After lyophilization of the pure fractions Compound 1034 is obtained.

Example 37

Preparation of Compound 1037

-continued
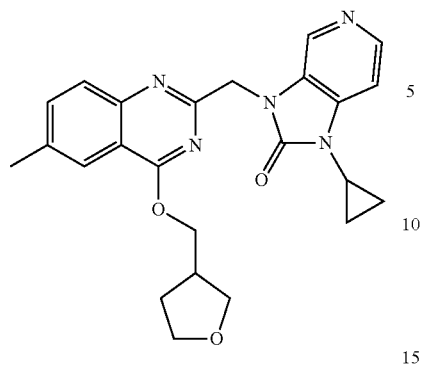
Compound 1037 is prepared using the method of Example 36, replacing 1032 with 1031.
Example 38
Preparation of Compound 1048
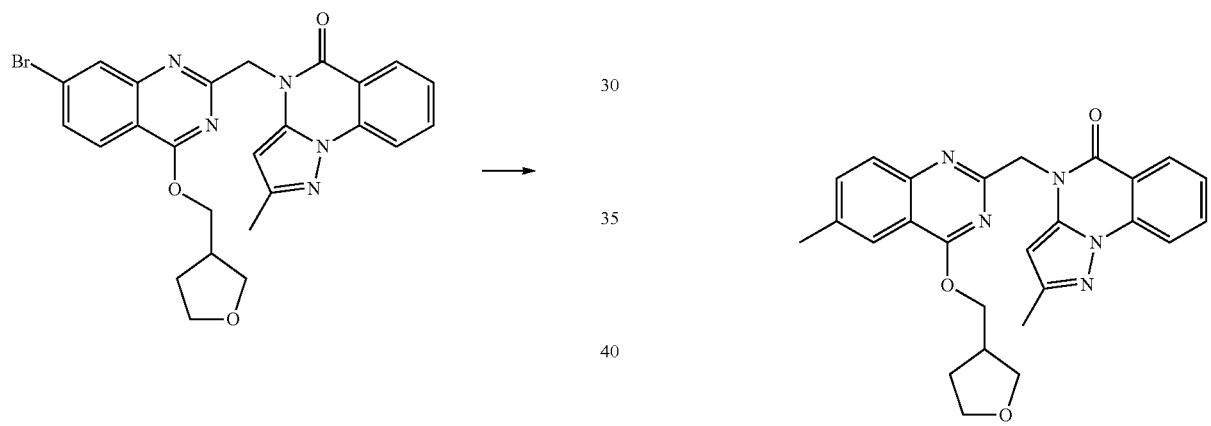
Compound 1048 is prepared using the method of Example 36, replacing 1032 with 1047.
Example 39
Preparation of Compound 1075
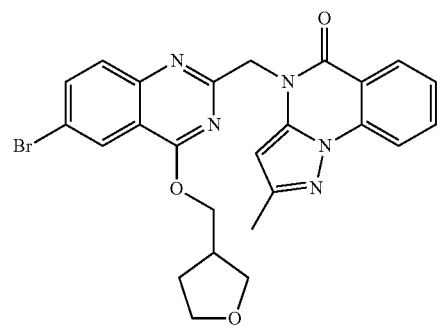
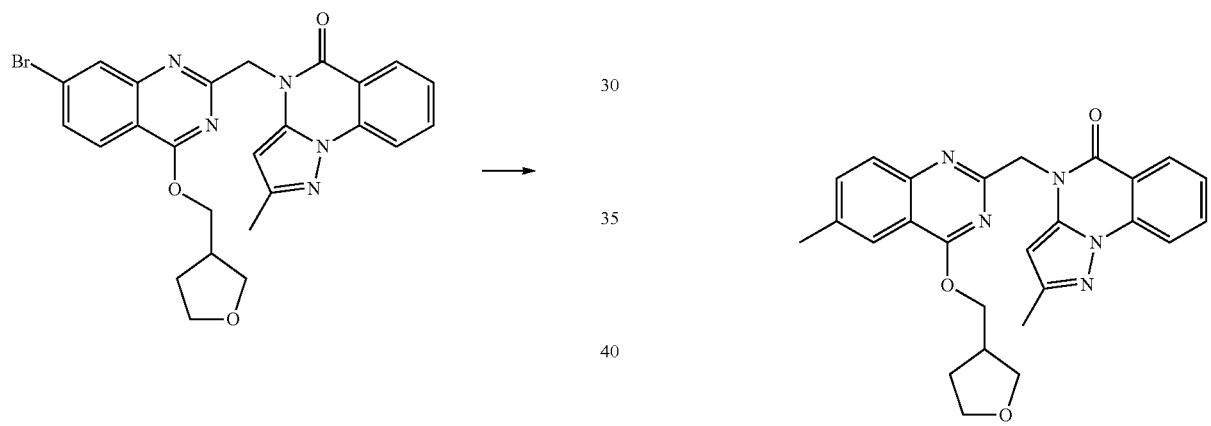
Compound 1075 is prepared using the method of Example 36, replacing 1032 with 1073.
Example 40
Preparation of Compound 1043
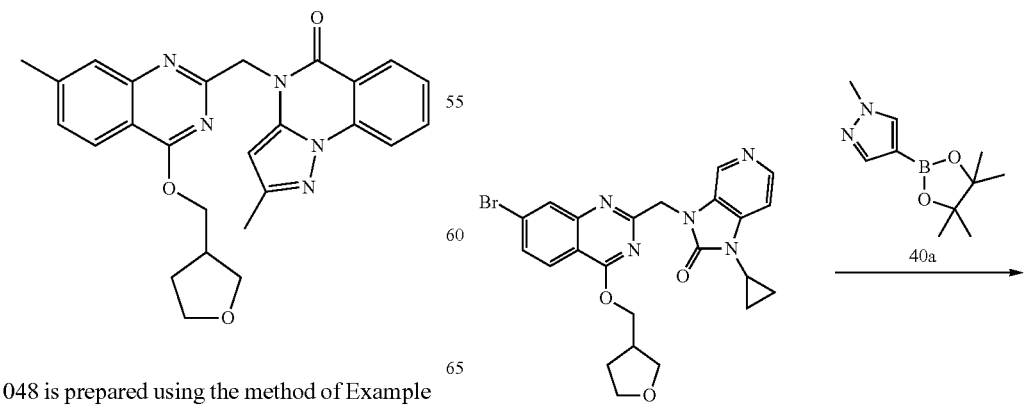

193
-continued

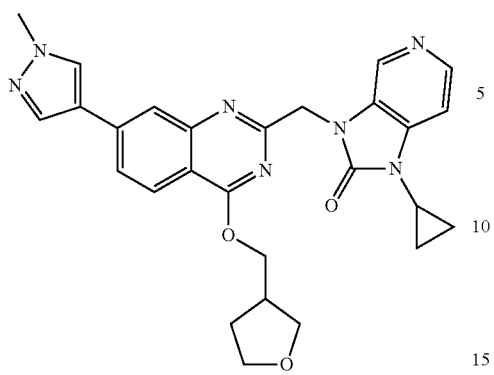

To a suspension of 1-Methyl-4-(4,4,5,5-tetramethyl-[1,3,2]dioxaborolan-2-yl)-1H-pyrazole 40a (Frontier Scientific) (62.9 mg, 0.302 mmol) in argon-degassed 1,4-dioxane (1.5 mL), is added compound 1032 (100 mg, 0.201 mmol), water (0.4 mL), potassium carbonate (83.5 mg, 0.604 mmol) and cesium fluoride (91.8 mg, 0.604 mmol). Palladium(dppf) dichloride:dichloromethane adduct (Strem) (16.5 mg, 0.020 mmol) is added and the reaction mixture is heated to 125° C. using microwave irradiation for 30 min with stirring. The organic phase is transferred to a vial and acetic acid (1 mL) is added. The product is purified using preparative HPLC. After lyophilization of the pure fractions Compound 1043 is obtained.

Example 41

Preparation of Compound 1039

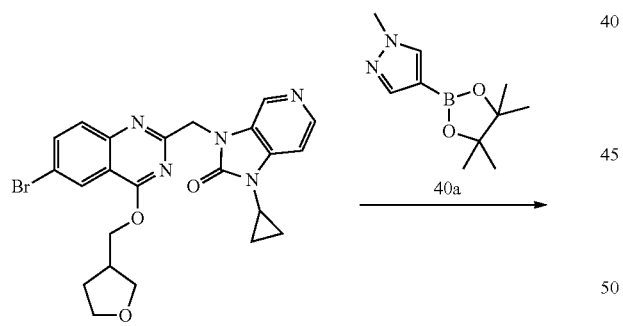

Compound 1039 is prepared using the method of Example 40, replacing 1032 with 1031.

194

Example 42

Preparation of Compound 1040

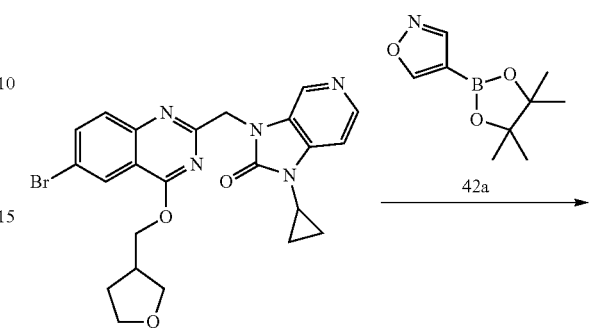

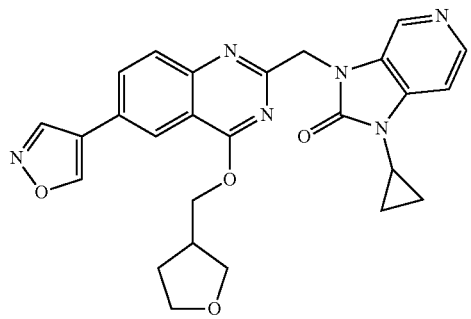

Compound 1040 is prepared using the method of Example 40, replacing 1032 with 1031, and replacing 1-methyl-4-(4,4,5,5-tetramethyl-[1,3,2]dioxaborolan-2-yl)-1H-pyrazole 40a with 4-(4,4,5,5-tetramethyl-[1,3,2]dioxaborolan-2-yl)-isoxazole 42a (Frontier Scientific).

Example 43

Preparation of Compound 1041

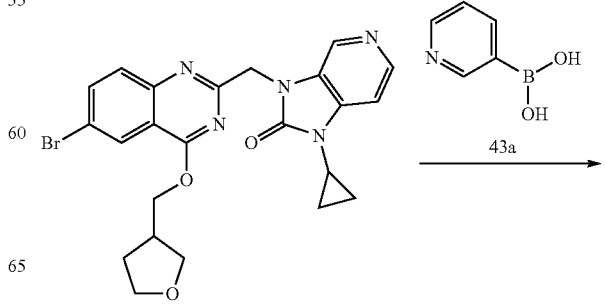

-continued

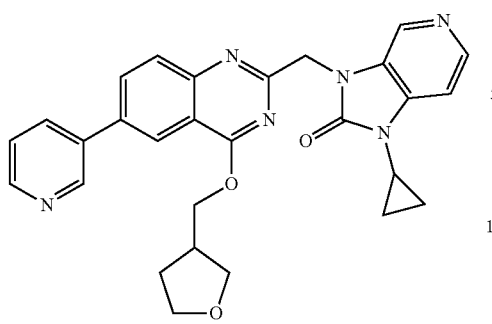

Compound 1041 is prepared using the method of Example 40, replacing 1032 by 1031, and replacing 1-methyl-4-(4,4,5,5-tetramethyl-[1,3,2]dioxaborolan-2-yl)-1H-pyrazole 40a with 3-pyridineboronic acid 43a (Aldrich).

Example 44

Preparation of Compound 1044

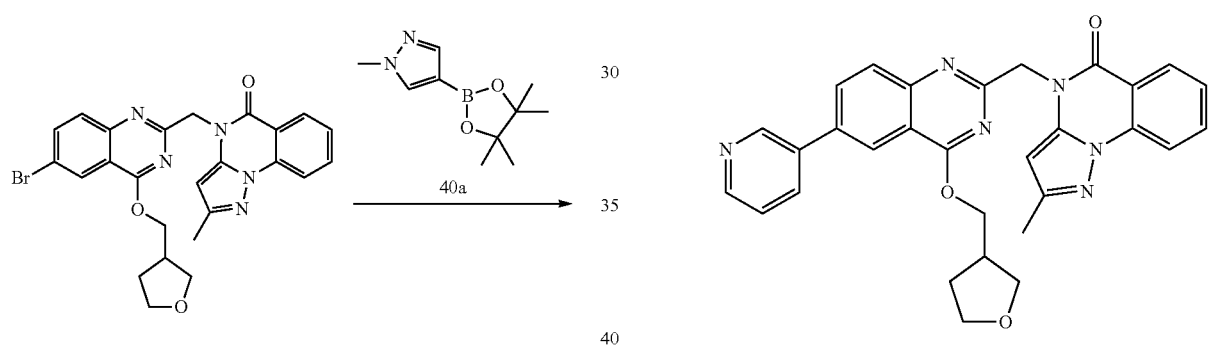

Compound 1044 is prepared using the method of Example 40, replacing 1032 by 1073.

Example 45

Preparation of Compound 1045

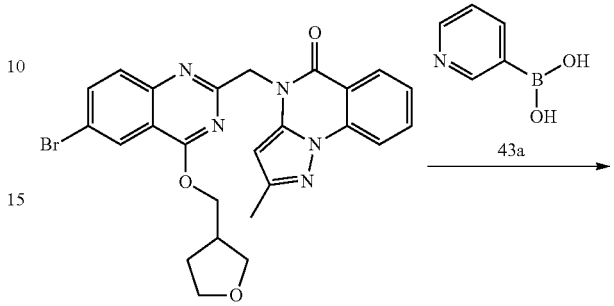

Compound 1045 is prepared using the method of Example 40, replacing 1032 by 1073, and replacing 1-Methyl-4-(4,4,5,5-tetramethyl-[1,3,2]dioxaborolan-2-yl)-1H-pyrazole 40a with 3-pyridineboronic acid 43a (Aldrich).

Example 46

Preparation of Compound 1042

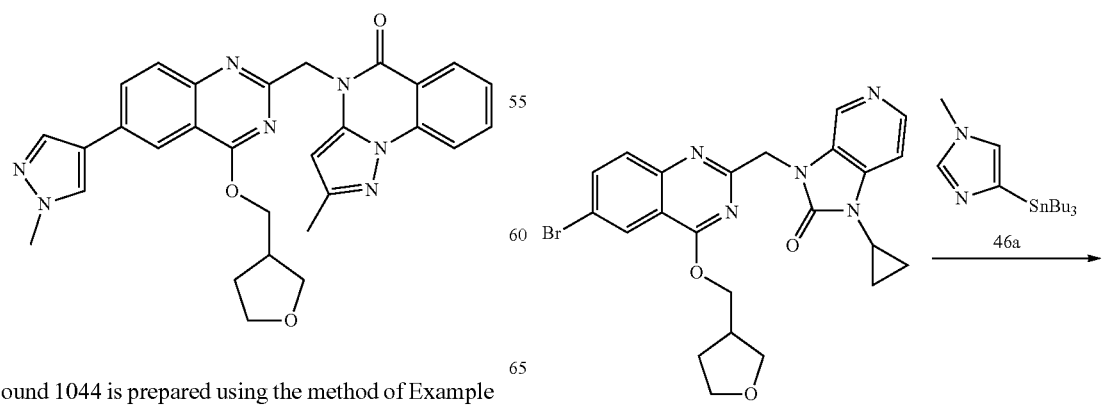

-continued

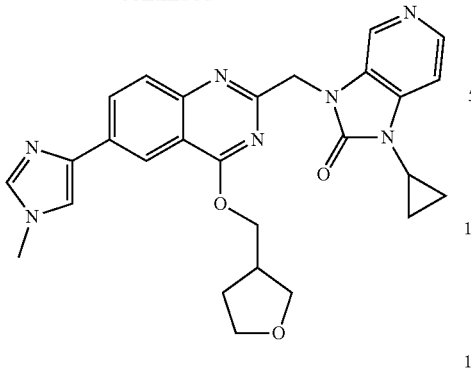

Compound 1031 (40 mg, 0.081 mmol), 1-Methyl-4-tributylstannanyl-1H-imidazole 46a (Aldrich) (37.4 mg, 0.101 mmol), and palladium(dppf)dichloride: dichloromethane adduct (6.6 mg, 0.008 mmol) are dissolved in DMF (0.98 mL). The reaction mixture is degassed with Argon and then heated to 125° C. using microwave irradiation for 15 min with stirring. The reaction mixture is diluted with acetic acid and purified using preparative HPLC. After lyophilization of the pure fractions Compound 1042 is obtained.

Example 47

Preparation of Compound 1046

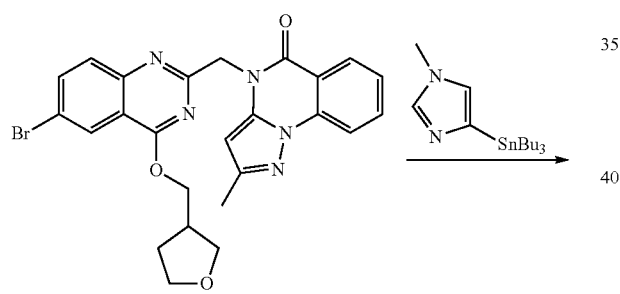

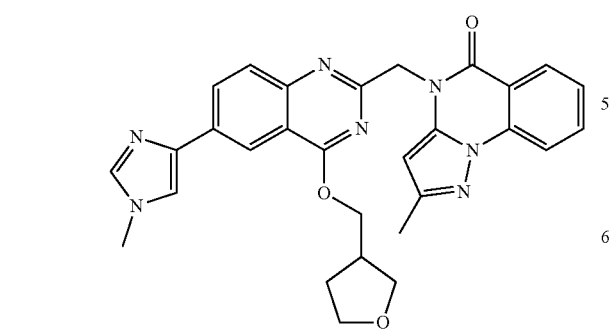

Compound 1046 is prepared using the method of Example 46, replacing 1031 by 1073.

Example 48

Preparation of Compound 1049

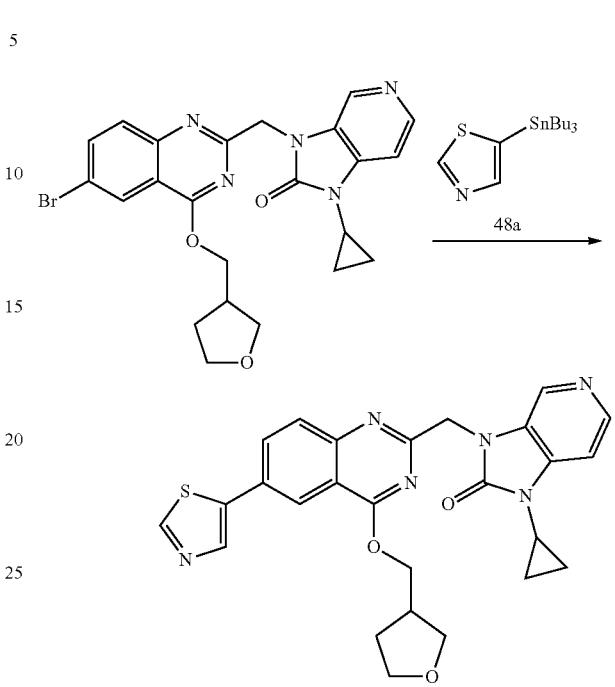

Compound 1049 is prepared using the method of Example 46, replacing 1-methyl-4-tributylstannanyl-1H-imidazole 46a by 5-tributylstannylthiazole 48a (Synthonix).

Example 49

Preparation of Compound 1050

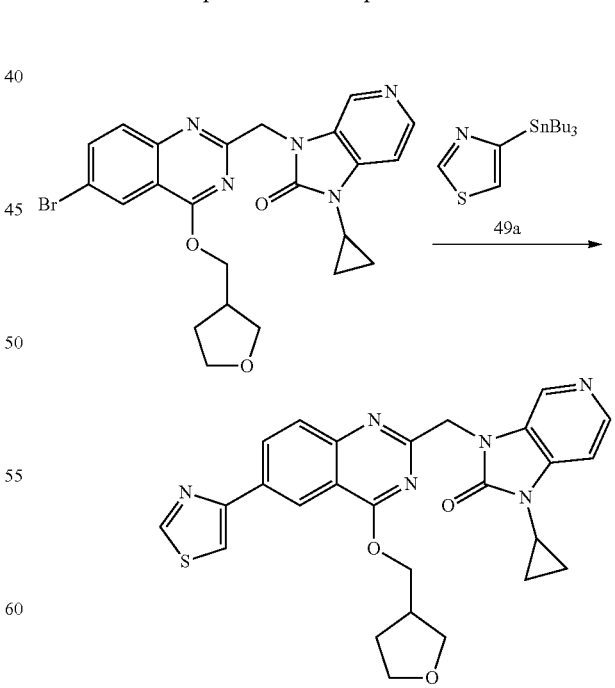

Compound 1050 is prepared using the method of Example 46, replacing 1-methyl-4-tributylstannanyl-1H-imidazole 46a by 4-tributylstannylthiazole 49a (Synthonix).

Example 50

Preparation of Compound 1051

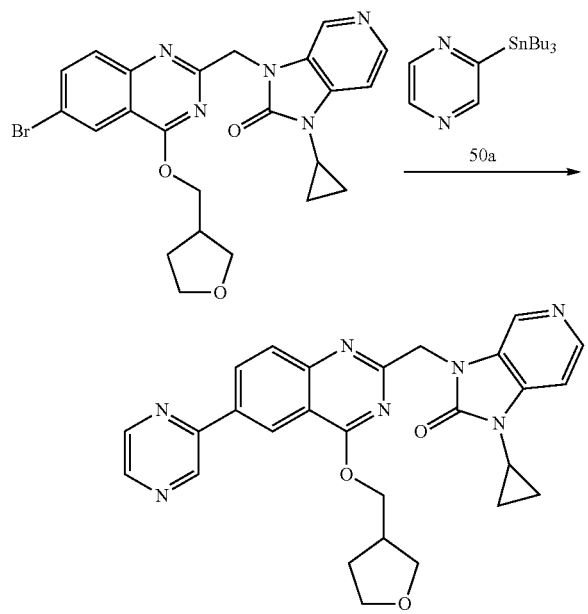

Compound 1051 is prepared using the method of Example 46, replacing 1-methyl-4-tributylstannanyl-1H-imidazole 46a by 2-tributylstannylpyrazine 50a (Aldrich).

Example 51

Preparation of Compounds 1007 and 1008

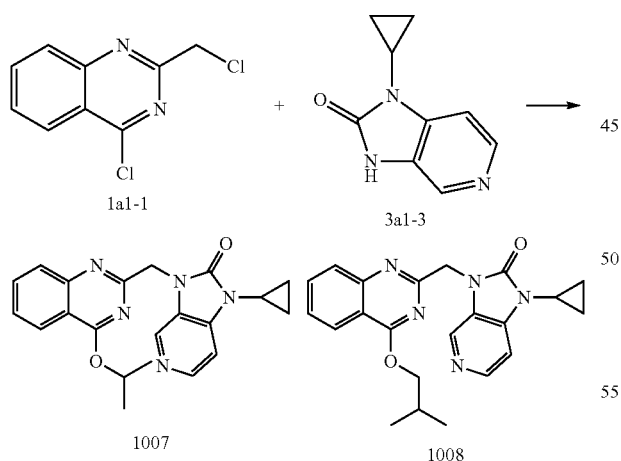

To an iPrOH (1.5 mL) suspension of 4-chloro-2-chloromethylquinazoline (Bioblocks, 35 mg, 0.164 mmol) is added 2-methyl-propan-1-ol (61 mg, 0.821 mmol) followed by Et₃N (0.046 mL, 0.328 mmol) and the reaction mixture is stirred at 75° C. for 1 h. The mixture is then diluted with EtOAc and washed with saturated NaHCO₃, dried over MgSO₄, filtered and concentrated to afford a residue. To a solution of the cyclic urea 3a1-3 (29 mg, 0.164 mmol) in DMA (1 mL) is added KOH (0.013 mL, 12.7 N). The solution is stirred at RT for 10 min and the previously obtained residue is added as a solution in DMA (0.5 mL). The resulting mixture is stirred at RT overnight, acidified with AcOH and purified by preparative HPLC to afford Compounds 1007 and 1008.

Example 52

Preparation of Compound 1062

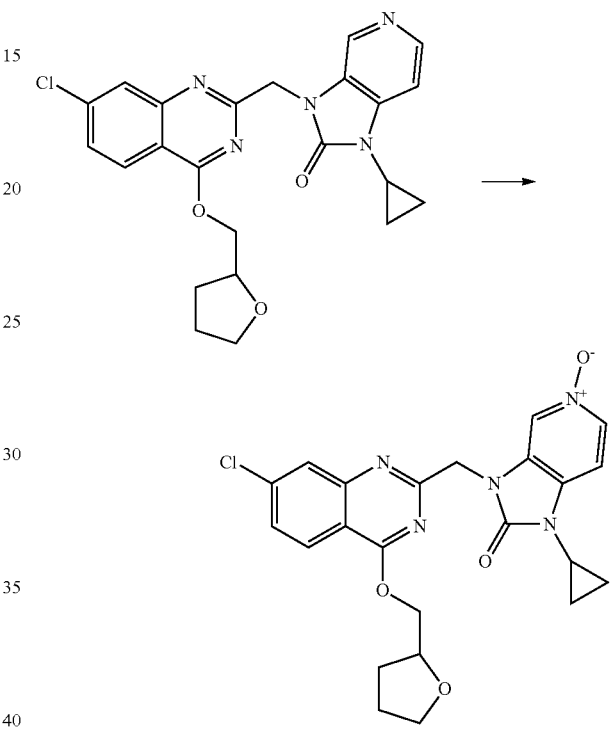

Compound 1033 (80 mg, 0.183 mmol) is dissolved in DCM (2 mL), cooled to 0° C., and m-CPBA (80% by weight, 39.4 mg, 0.183 mol) is added. The reaction mixture is stirred for 16 h. The volatiles are evaporated under reduced pressure, and the crude residue is dissolved in MeOH. The product is purified by preparative HPLC. After lyophilization of the pure fractions Compound 1062 is obtained.

Example 53

Preparation of Compound 1104

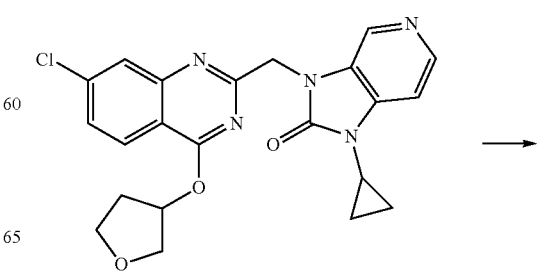

-continued

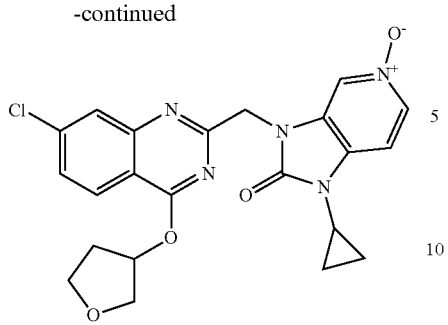

Compound 1104 is prepared using the method of Example 52, replacing 1033 with 1061.

Example 54

Preparation of Compound 1052

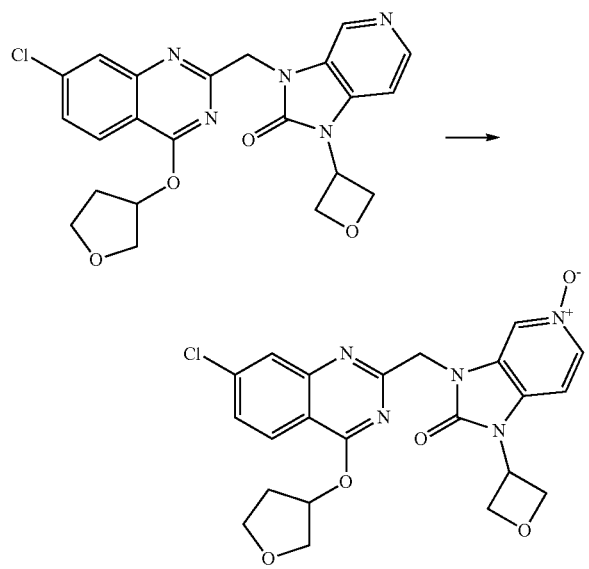

Compound 1052 is prepared using the method of Example 52, replacing 1033 with 1072.

Example 55

Preparation of Compound 1064

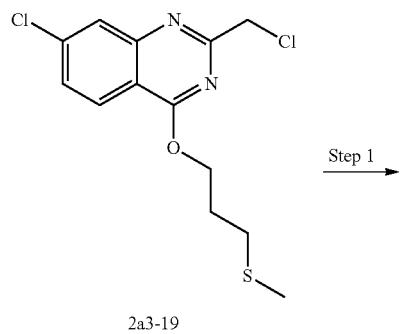

2a3-19

-continued

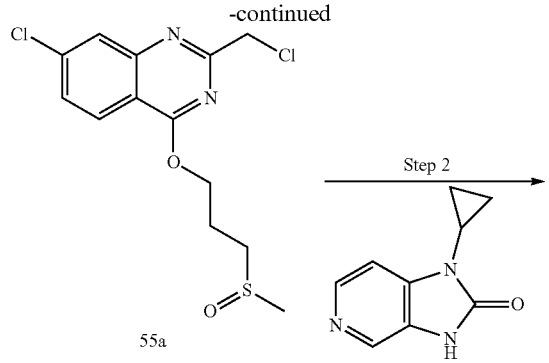

55a

3a1-3

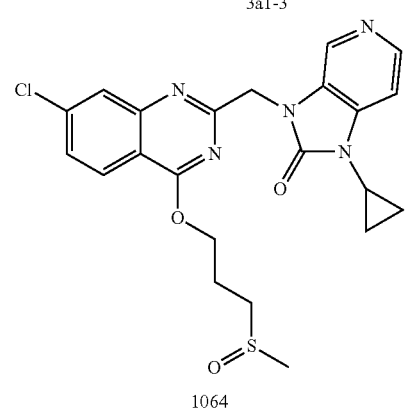

1064

Compound 2a3-19 (60 mg, 0.183 mmol) is dissolved in DCM (2 mL), cooled to 0° C., and m-CPBA (80% by weight, 44.9 mg, 0.208 mol) is added. The reaction mixture is stirred for 2 h, and then quenched with solid sodium thiosulfate. Saturated aqueous sodium bicarbonate and DCM are added. The mixture is shaken and after partitioning, the organic layer is collected, dried on sodium sulfate, filtered and evaporated under reduced pressure to provide Compound 55a.

Step 2

Compound 1064 is prepared according to general procedure C, using intermediate 55a and 3a1-3 as the starting materials. Purification using preparative HPLC and lyophilization affords 1064.

Example 56

Preparation of Compound 1065

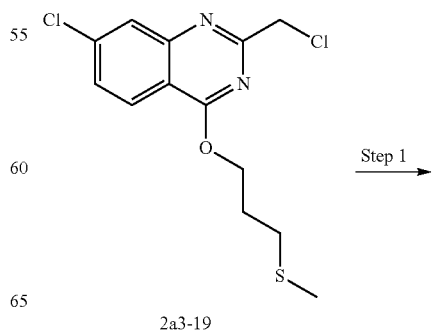

2a3-19

-continued

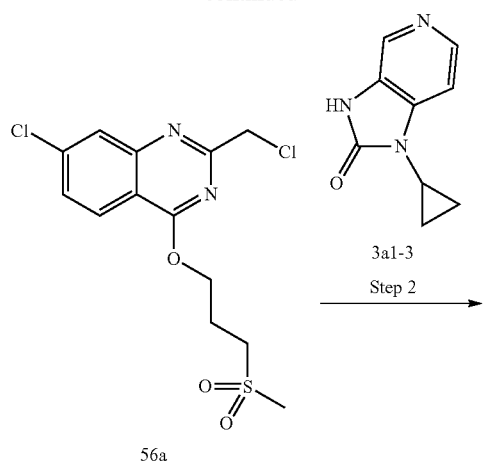

Step 1

Intermediate 56a is prepared according to Example 55, using 0.416 mmol of m-CPBA instead of 0.208 mmol in step 1.

Step 2

Compound 1065 is prepared according to general procedure C, using intermediate 56a and 3a1-3 as the starting materials. Purification using preparative HPLC and lyophilization affords Compound 1065.

Example 57

Preparation of Compound 1089

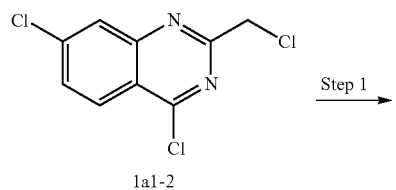

-continued

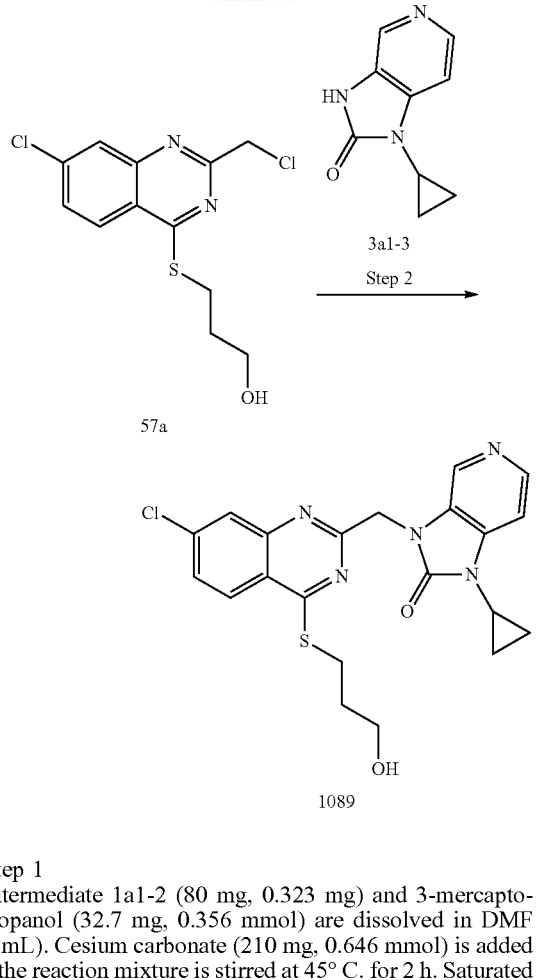

Step 1

Intermediate 1a1-2 (80 mg, 0.323 mg) and 3-mercapto-1-propanol (32.7 mg, 0.356 mmol) are dissolved in DMF (1.5 mL). Cesium carbonate (210 mg, 0.646 mmol) is added and the reaction mixture is stirred at 45° C. for 2 h. Saturated aqueous sodium bicarbonate is added to the mixture and extraction with EtOAc is performed twice. The combined organic layers are washed with brine, dried on sodium sulfate, filtered and evaporated under reduced pressure to afford 57a.

Step 2

Compound 1089 is prepared according to general procedure C, using intermediate 57a and 3a1-3 as the starting materials. Purification using preparative HPLC and lyophilization affords Compound 1089.

Example 58

Preparation of Compound 1086

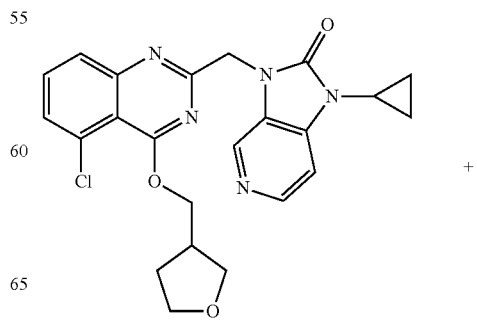

+

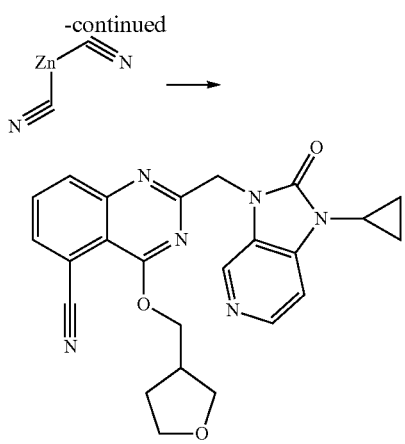

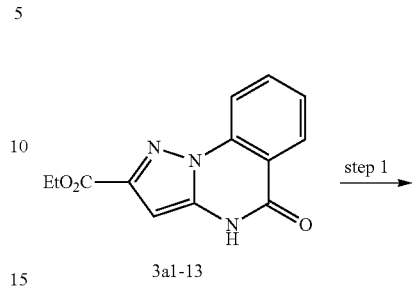

Example 60

Preparation of Compound 1029

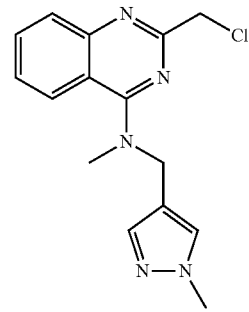

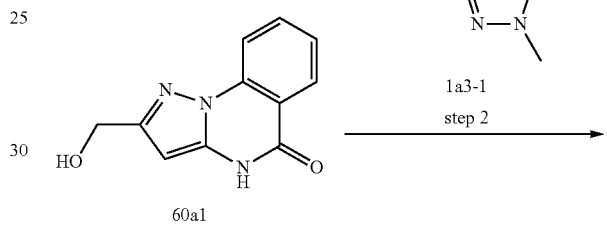

Compound 1085 (50 mg; 0.111 mmol), Zn(CN)₂ (Aldrich; 65 mg; 0.55 mmol) and bis(tri-t-butylphosphine)Pd(0) (28.2 mg; 0.055 mmol) are combined and dissolved in DMA (2 mL). The reaction mixture is heated in a microwave for 30 min at 150° C. The reaction mixture is taken up in EtOAc, washed with brine, dried (Na₂SO₄), filtered and concentrated to afford the crude product. Purification by preparative HPLC affords Compound 1086.

Example 59

Preparation of Compound 1087

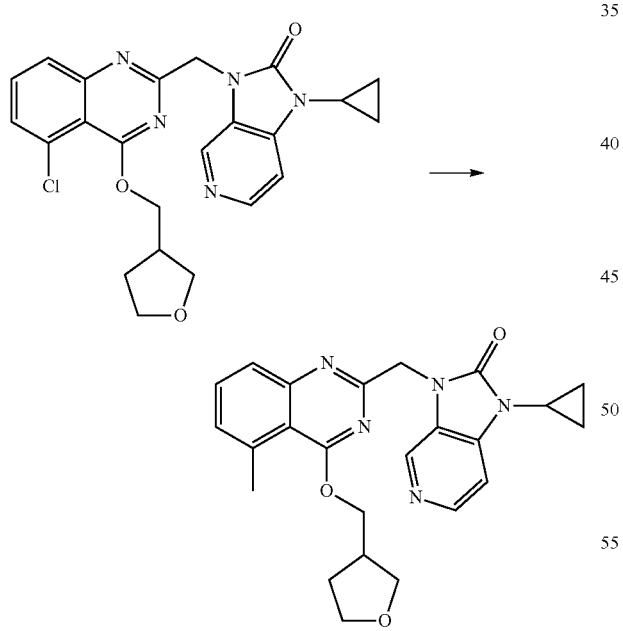

Compound 1085 (50 mg; 0.11 mmol), methyl boronic acid (39.7 mg; 0.66 mmol), CsF (50 mg; 0.33 mmol), bis(tri-t-butylphosphine)Pd(0) (28.2 mg; 0.055 mmol) are combined and dissolved in DMA (2 mL). The reaction mixture is heated in a microwave apparatus for 30 min at 150° C. The crude reaction is then purified by preparative-HPLC to afford Compound 1087.

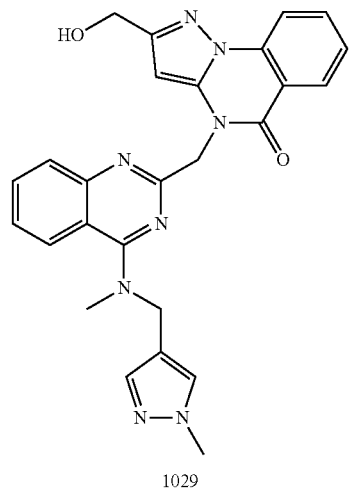

Step 1

To a suspension of the ester 3a1-13 in THF at 0° C., is added a 1.2 M solution of diisobutylaluminium hydride in hexane. The reaction mixture is stirred at 0° C. for 1 h, and then is warmed at RT overnight. A 1M HCl solution is added and the resulting mixture is stirred for 1 h. The solid in suspension is filtered and washed with a 1M HCl solution and EtOAc. This affords intermediate 60a1 which is directly used in the next step.

Step 2

A suspension of reagent 60a1 (21 mg, 0.098 mmol), reagent 1a3-1 (30 mg, 0.099 mmol) and cesium carbonate (40 mg, 0.123 mmol) in DMF/water (9/1) is stirred at 80° C.

Example 61

Preparation of Compound 1181

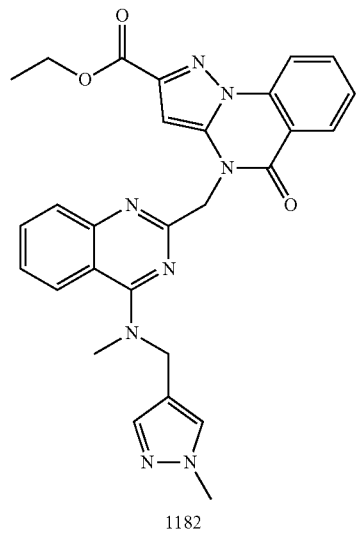

Example 62

Preparation of Compound 1091

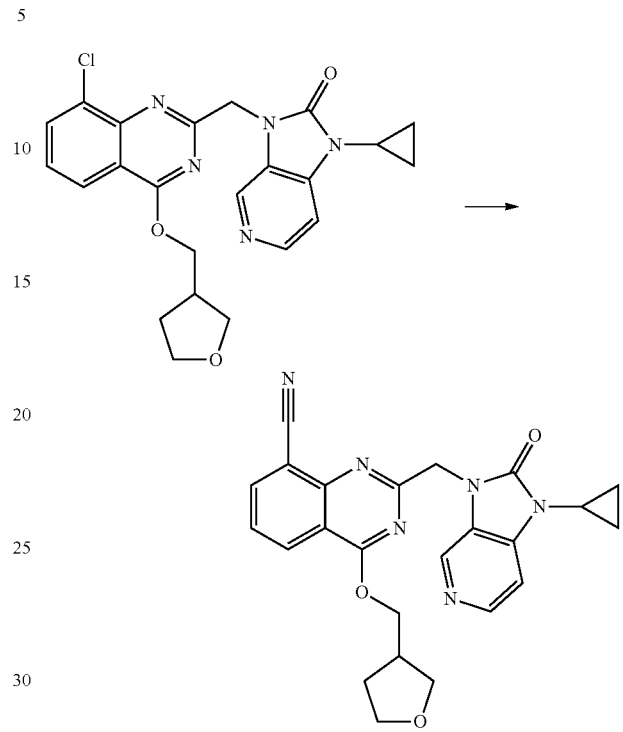

Compound 1091 is prepared using the method of Example 58, replacing 1085 by 1090.

Example 63

Preparation of Compound 1092

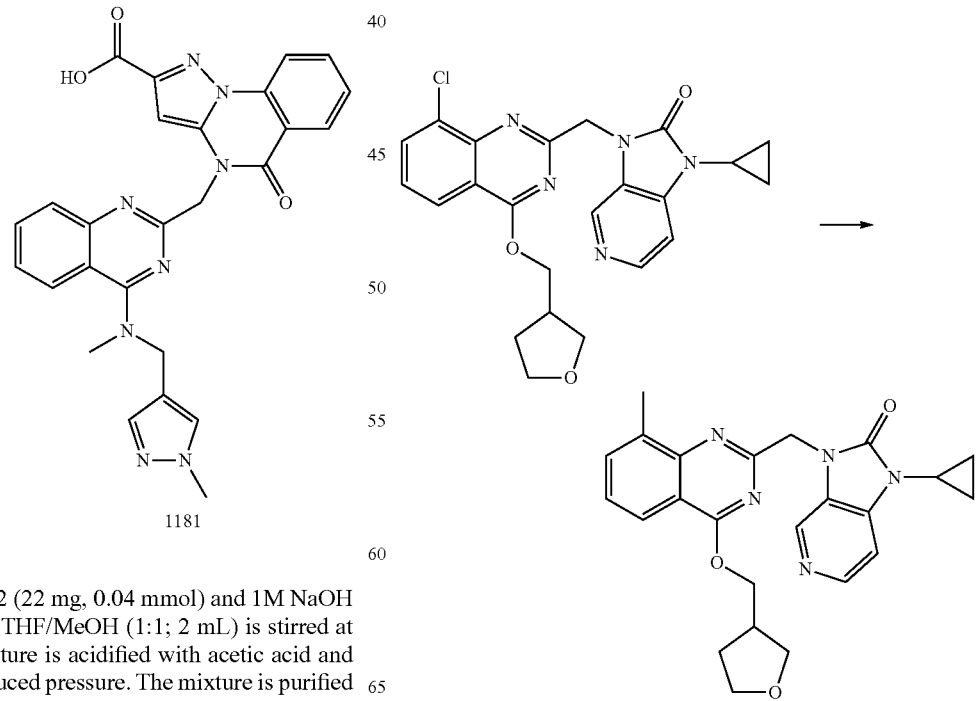

A suspension of 1182 (22 mg, 0.04 mmol) and 1M NaOH (0.2 mL, 0.2 mmol) in THF/MeOH (1:1; 2 mL) is stirred at RT overnight. The mixture is acidified with acetic acid and concentrated under reduced pressure. The mixture is purified by mass directed purification on reverse phase HPLC column to afford compound 1181.

Compound 1092 is prepared using the method of Example 59, replacing 1085 by 1090.

Example 64

Preparation of Compound 1015

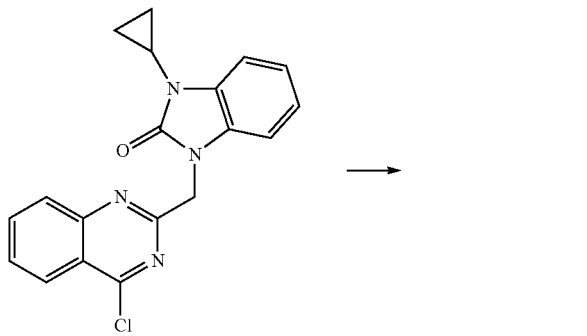

4a2-1

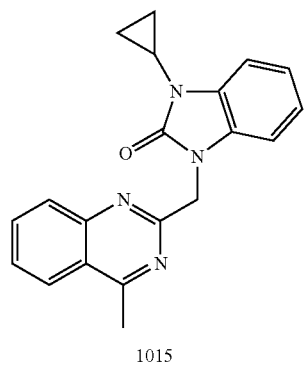

1015

To a suspension of the intermediate 4a2-1 (40 mg, 0.114 mmol), 2,4,4,5,5-pentamethyl-[1,3,2]dioxaborolane (32 mg, 0.228 mmol), NaHCO₃ (29 mg, 0.347 mmol) in dioxane/H₂O (4:1, 1 mL) is added PdCl₂dppf (9 mg, 0.012 mmol). The mixture is heated at 120° C. for 15 min in the microwave. The reaction mixture is acidified with AcOH and then purified using the preparative HPLC to afford Compound 1015.

Example 65

Preparation of Compound 1016

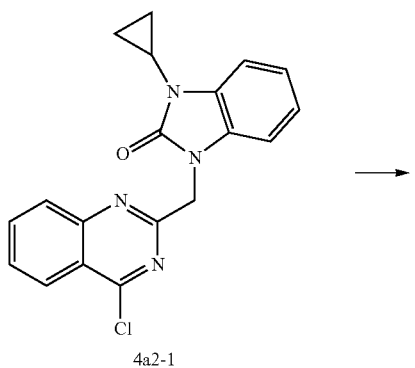

4a2-1

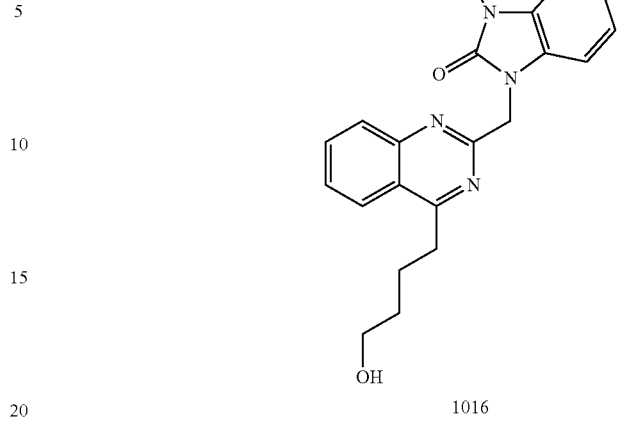

1016

To a DMF (2 mL) solution of intermediate 4a2-1 (50 mg, 0.142 mmol) is added but-3-yn-1-ol (10 mg, 0.142 mmol), Et₃N (43 mg, 0.425 mmol) followed by CuI (2.7 mg, 0.014 mmol) and trans-dichlorobis(triphenylphosphine)palladium (11) (10 mg, 0.014 mmol). The resulting mixture is heated in a microwave at 115° C. for 10 min. The resulting solution is purified using preparative HPLC. The obtained intermediate is dissolved with MeOH (3 mL) and 5% Pd/C (10 mg) is added. The system is purged with H₂ and stirred for 2 h at RT. The resulting mixture is filtered and the filtrate purified by preparative HPLC to afford Compound 1016.

Example 66

Preparation of Compound 1018

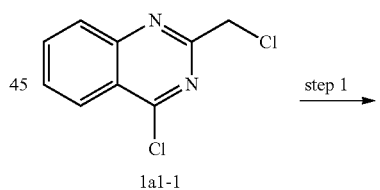

1a1-1

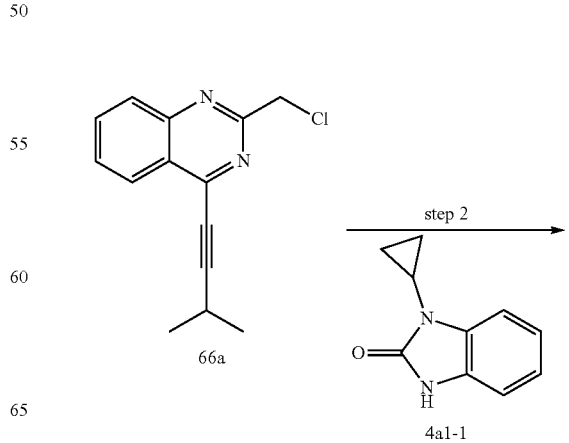

66a

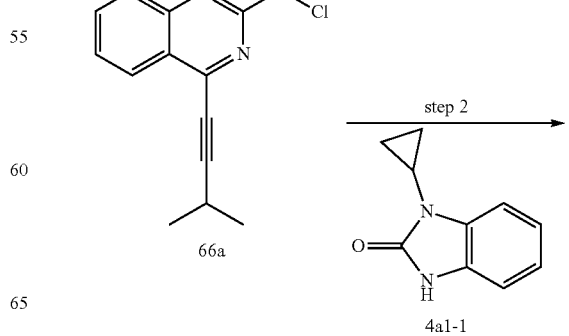

4a1-1

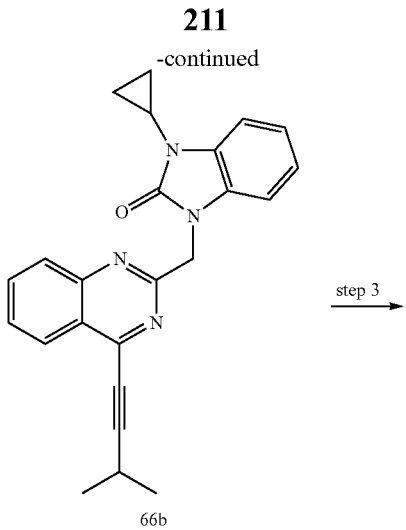

66b

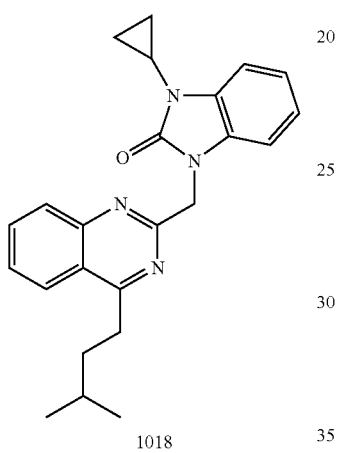

1018

Example 67

Preparation of Compound 1002

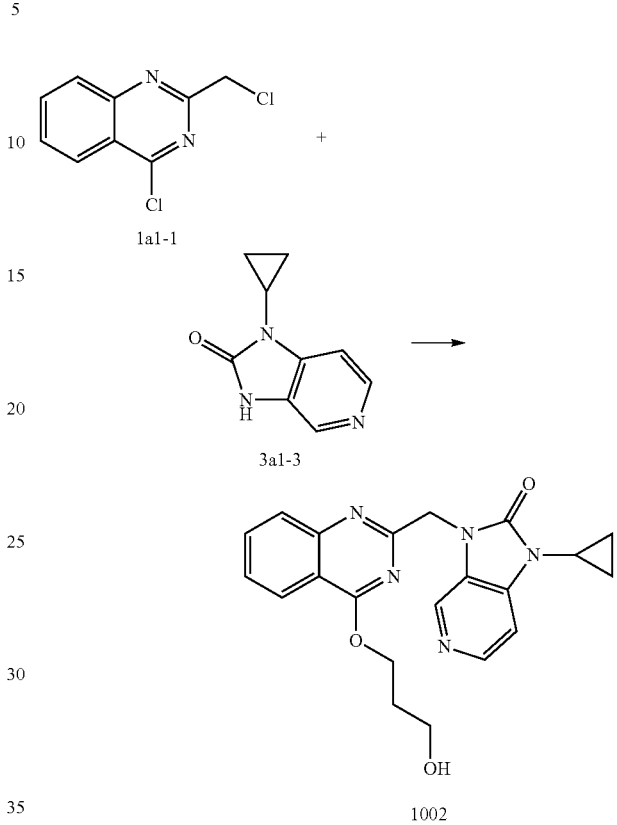

Step 1

To a THF (2 mL) solution of 4-chloro-2-chloromethylquinazoline 1a1-1 (Bioblocks, 100 mg, 0.469 mmol) is added 3-methyl-but-1-yne (0.032 mL, 0.489 mmol), Et$_3$N (142 mg, 1.411 mmol) followed by CuI (8.9 mg, 0.047 mmol) and trans-dichlorobis(triphenylphosphine)palladium (II) (33 mg, 0.047 mmol). The resulting mixture is heated in the microwave at 95° C. for 10 min. The resulting solution is filtered and purified by flash chromatography using EtOAc/hexanes to afford intermediate 66a.

Step 2

To a solution of urea 4a1-1 (82 mg, 0.468 mmol) in DMA (1 mL) is added KOH (0.075 mL, 12.7 N). The reaction is stirred at RT and intermediate 66a (115 mg, 0.468 mmol) is added as a solid to the mixture. The mixture is stirred at RT for 2 h. The reaction mixture is diluted with EtOAc and water. The layers are separated and the aqueous layers are extracted with EtOAc. The organic layers are combined, washed twice with water, brine, dried over MgSO$_4$, filtered and concentrated. Flash chromatography eluting with 20-100% EtOAc in hexanes is used to afford intermediate 66b.

Step 3

Intermediate 66b (100 mg, 0.261 mmol) is dissolved in MeOH (3 mL) and 5% Pd/C (10 mg) is added. The system is purged with H$_2$ and stirred for 2 h at RT. The resulting mixture is filtered and the filtrate purified by preparative HPLC to afford Compound 1018.

To an iPrOH (1.5 mL) suspension of 4-chloro-2-chloromethylquinazoline 1a1-1 (Bioblocks, 35 mg, 0.164 mmol) is added 1,3-propanediol (13 mg, 0.164 mmol) followed by Et$_3$N (0.046 mL, 0.328 mmol) and the reaction mixture is stirred at 75° C. for 1 h. The mixture is then diluted with EtOAc and washed with saturated NaHCO$_3$, dried over MgSO$_4$, filtered and concentrated to afford a residue. To a solution of the cyclic urea 3a1-3 (29 mg, 0.164 mmol) in DMA (1 mL) is added KOH (0.013 mL, 12.7 N). The solution is stirred at RT for 10 min. and the previously obtained residue is added as a solution in DMA (0.5 mL). The resulting mixture is stirred at RT overnight, acidified with AcOH and purified by preparative HPLC to afford Compound 1002.

Retention times ($t_R$) for each compound are measured using the standard analytical HPLC or UPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC or UPLC instruments. Even when measured on the same instrument, the values may vary when measured, for example, using different individual HPLC or UPLC columns, or, when measured on the same instrument and the same individual column, the values may vary, for example, between individual measurements taken on different occasions.

| Cmpd # | [M + H]+ | $t_R$ (min) |
|---|---|---|
| 1001 | 391.3/392.3 | 0.46 |
| 1002 | 392.3/393.0 | 0.7 |
| 1003 | 416.3/417.4 | 0.77 |
| 1004 | 430.4/431.1 | 0.87 |
| 1005 | 440.4/441.3 | 0.81 |
| 1006 | 390.4/391.3 | 0.75 |
| 1007 | 376.3/377.3 | 0.93 |
| 1008 | 390.3/391.3 | 1.04 |
| 1009 | 446.5/447.4 | 0.88 |
| 1010 | 418.4/419.4 | 0.9 |
| 1011 | 427.4/428.4 | 0.92 |
| 1012 | 424.4/425.4 | 0.94 |
| 1013 | 444.4/445.4 | 0.94 |
| 1014 | 417.4/418.4 | 1.29 |
| 1016 | 389.6 | 1.1 |
| 1017 | 418.1/419.1 | 0.82 |
| 1018 | 388.2/389.2 | 1.04 |
| 1019 | 450.1 | 1.54 |
| 1020 | 418.1 | 1.62 |
| 1021 | 461.2 | 1.8 |
| 1022 | 415.1 | 1.66 |
| 1023 | 415.1 | 1.58 |
| 1024 | 441.1 | 1.38 |
| 1025 | 414.1 | 1.61 |
| 1026 | 413.1 | 1.53 |
| 1027 | 465.1 | 1.67 |
| 1028 | 385.1 | 1.54 |
| 1029 | 481.2 | 1.28 |
| 1030 | 401.1 | 1.35 |
| 1031 | 496.0/498.0 | 0.98 |
| 1032 | 496.1/498.0 | 0.98 |
| 1033 | 452.1/454.1 | 0.96 |
| 1034 | 432.2 | 0.9 |
| 1035 | 436.2 | 0.88 |
| 1036 | 443.2 | 0.82 |
| 1037 | 432.2 | 0.89 |
| 1038 | 443.2 | 0.84 |
| 1039 | 498.1 | 0.8 |
| 1040 | 485.1 | 0.87 |
| 1041 | 495.1 | 0.6 |
| 1042 | 498.1 | 0.59 |
| 1043 | 498.2 | 0.83 |
| 1044 | 522.2 | 1.24 |
| 1045 | 519.1 | 0.98 |
| 1046 | 522.2 | 0.95 |
| 1047 | 520.1/522.1 | 1.67 |
| 1048 | 456.2 | 1.44 |
| 1049 | 501 | 0.83 |
| 1050 | 501.1 | 0.9 |
| 1051 | 496.2 | 0.81 |
| 1052 | 470.1/472.1 | 0.86 |
| 1053 | 426.1/428.1 | 0.85 |
| 1054 | 452.1/454.1 | 0.98 |
| 1055 | 526 | 0.99 |
| 1056 | 540.1/542.1 | 1.0 |
| 1057 | 574.1/576.1 | 0.97 |
| 1058 | 484.2/486.2 | 0.96 |
| 1059 | 480.1/482.1 | 1.08 |
| 1060 | 466.1/468.1 | 1.03 |
| 1061 | 438.1/440.1 | 0.92 |
| 1062 | 468.1/470.1 | 0.97 |
| 1063 | 452.1/454.1 | 0.93 |
| 1064 | 472.1/474.1 | 0.79 |
| 1065 | 488.1/490.1 | 0.88 |
| 1066 | 475.1/477.0 | 0.61 |
| 1067 | 466.1/468.1 | 1.02 |
| 1068 | 424.1/426.1 | 0.89 |
| 1069 | 391 | 1.73 |
| 1070 | 442.1 | 1.86 |
| 1071 | 431.2 | 1.85 |
| 1072 | 454.0/456.0 | 1.05 |
| 1073 | 520.1/522.1 | 1.62 |
| 1074 | 467.1 | 1.36 |
| 1075 | 456.1 | 1.42 |
| 1076 | 503.0/505.0 | 0.71 |
| 1077 | 523.0/525.1 | 0.86 |
| 1078 | 472.0/474.0 | 1.04 |
| 1079 | 472.1/474.1 | 1.06 |
| 1080 | 494.1/496.1 | 1.36 |
| 1081 | 523.1/525.1 | 0.88 |
| 1082 | 496.0/498.0 | 1.01 |
| 1083 | 498.1/500.1 | 1.12 |
| 1084 | 482.1/484.1 | 0.94 |
| 1085 | 452.2 | 0.93 |
| 1086 | 443.2 | 0.8 |
| 1087 | 432.2 | 0.89 |
| 1088 | 465.1/467.1 | 0.62 |
| 1089 | 442.1/444.1 | 0.92 |
| 1090 | 452.1 | 1.16 |
| 1091 | 443.2 | 1.04 |
| 1092 | 432.2 | 1.24 |
| 1093 | 482.1/484.1 | 0.95 |
| 1094 | 482.1/484.1 | 0.96 |
| 1095 | 496.2/498 | 0.98 |
| 1096 | 530.3/532.2 | 0.95 |
| 1097 | 428.2 | 0.86 |
| 1098 | 465.2 | 0.57 |
| 1099 | 455.2 | 0.6 |
| 1100 | 428.1 | 0.88 |
| 1101 | 480.2 | 0.82 |
| 1102 | 470.1/472.0 | 0.85 |
| 1103 | 436.1 | 0.73 |
| 1104 | 454.1/456.0 | 0.92 |
| 1105 | 429.1 | 1.23 |
| 1106 | 429.1 | 1.23 |
| 1107 | 443.1 | 1.28 |
| 1108 | 399.1 | 1.21 |
| 1109 | 446.1 | 1.31 |
| 1110 | 441.1 | 1.69 |
| 1111 | 417 | 1.38 |
| 1112 | 390.1 | 1.6 |
| 1113 | 377.1 | 1.35 |
| 1114 | 431.4 | 1.43 |
| 1115 | 404 | 1.64 |
| 1116 | 405.1 | 1.68 |
| 1117 | 391 | 1.62 |
| 1118 | 444.1 | 1.75 |
| 1119 | 391.1 | 1.38 |
| 1120 | 390 | 1.6 |
| 1121 | 427.1 | 1.93 |
| 1122 | 403.1 | 1.67 |
| 1123 | 377.1 | 1.93 |
| 1124 | 375.1 | 1.93 |
| 1125 | 405 | 1.33 |
| 1126 | 378.1 | 1.56 |
| 1127 | 415.1 | 1.63 |
| 1128 | 466.2 | 1.74 |
| 1129 | 396.1 | 1.57 |
| 1130 | 451.1 | 1.61 |
| 1131 | 438.1 | 1.36 |
| 1132 | 411.1 | 1.61 |
| 1133 | 453.3 | 1.43 |
| 1134 | 417.1 | 1.35 |
| 1135 | 495.2 | 1.66 |
| 1136 | 429.1 | 1.65 |
| 1137 | 491.2 | 1.66 |
| 1138 | 428.1 | 1.5 |
| 1139 | 462.4 | 1.67 |
| 1140 | 455.3 | 1.71 |
| 1141 | 441 | 1.65 |
| 1142 | 391.1 | 1.81 |
| 1143 | 427.1 | 1.73 |
| 1144 | 423.1 | 1.53 |
| 1145 | 447.2 | 1.54 |
| 1146 | 460.2 | 1.82 |
| 1147 | 471.2 | 1.74 |
| 1148 | 420.1 | 1.71 |
| 1149 | 467.2 | 1.91 |
| 1150 | 452.2 | 1.44 |
| 1151 | 405.1 | 1.78 |
| 1152 | 416.1 | 1.77 |
| 1153 | 365.1 | 1.67 |
| 1154 | 412.1 | 1.87 |
| 1155 | 401.1 | 1.62 |
| 1156 | 397.1 | 1.38 |
| 1157 | 460.2 | 1.47 |

-continued

| Cmpd # | [M + H]+ | $t_R$ (min) |
|---|---|---|
| 1158 | 484.2 | 1.73 |
| 1159 | 433.2 | 1.66 |
| 1160 | 480.2 | 1.82 |
| 1161 | 469.2 | 1.59 |
| 1162 | 465.2 | 1.36 |
| 1163 | 442.1 | 1.45 |
| 1164 | 455.2 | 1.79 |
| 1165 | 451.1 | 1.6 |
| 1166 | 466.1 | 1.73 |
| 1167 | 415.1 | 1.68 |
| 1168 | 462.2 | 1.84 |
| 1169 | 426.1 | 1.59 |
| 1170 | 440.2 | 1.59 |
| 1171 | 436.1 | 1.37 |
| 1172 | 426.1 | 1.55 |
| 1173 | 408.2 | 1.61 |
| 1174 | 409.1 | 1.01 |
| 1175 | 410.1 | 1.27 |
| 1176 | 400.1 | 1.52 |
| 1177 | 447.1 | 1.53 |
| 1178 | 443.1 | 1.31 |
| 1179 | 476.4 | 1.59 |
| 1180 | 465.4 | 1.64 |
| 1181 | 495.4 | 1.15 |
| 1182 | 523.4 | 1.63 |
| 1183 | 451.2 | 1.21 |
| 1184 | 507.6 | 1.98 |
| 1185 | 450.8 | 1.45 |
| 1186 | 478.8 | 1.7 |
| 1187 | 452.2 | 1.35 |
| 1188 | 513.5 | 1.68 |
| 1189 | 441.2 | 1.24 |
| 1190 | 497.5 | 2.01 |
| 1191 | 441.2 | 1.48 |
| 1192 | 469.5 | 1.73 |
| 1193 | 442.2 | 1.41 |
| 1194 | 466.2 | 1.55 |
| 1195 | 486.5 | 1.85 |
| 1196 | 414.5 | 1.56 |
| 1197 | 471.2 | 12.08 |
| 1198 | 414.9 | 1.72 |
| 1199 | 442.6 | 1.88 |
| 1200 | 415.2 | 1.62 |
| 1201 | 416.5 | 1.63 |
| 1202 | 439.5 | 1.74 |
| 1203 | 453.2 | 1.37 |
| 1204 | 413.1 | 1.61 |
| 1205 | 428.2 | 1.79 |
| 1206 | 404.1 | 1.48 |
| 1207 | 429.1 | 1.59 |
| 1208 | 456.2 | 1.58 |
| 1209 | 456.2 | 1.49 |
| 1210 | 466.2 | 1.47 |
| 1211 | 463.2 | 1.43 |
| 1212 | 466.2 | 1.54 |
| 1213 | 466.2 | 1.51 |
| 1214 | 456.2 | 1.4 |
| 1215 | 495.2 | 1.44 |
| 1216 | 452.1 | 1.8 |
| 1217 | 452.1 | 1.8 |
| 1218 | 438.1 | 1.75 |
| 1219 | 438.1 | 1.75 |
| 1220 | 404.3 | 1.55 |
| 1221 | 403.8 | 1.56 |
| 1222 | 418.1 | 1.62 |

Example A

RSV Cytopathic Effect

Compounds of the invention are initially tested in a cytopathic effect (CPE)-based viral replication assay using immortalized cells and a laboratory strain of RSV (Long). This assay evaluates the ability of a compound to inhibit viral replication.

Procedure:

Assay plates are prepared by seeding 2,500 HEp-2 cells (ATCC) per well of a 384-well black clear-bottom plate (Greiner Bio-One) in 20 µL of assay media (defined as DMEM supplemented with 2% heat-inactivated fetal bovine serum and 1% Penicillin/Streptomycin). Assay plates are incubated overnight at 37° C. in an incubator containing 5% $CO_2$. The following day, a 10-point serial dilution of test compound is prepared in DMSO. Compounds are subsequently diluted with assay media and 20 µL of diluted compound (containing 1.5% DMSO) is transferred to an assay plate for evaluation of antiviral activity.

For the CPE assay, cells are infected at a MOI of 0.015 using 20 µL of RSV Long (ATCC) diluted in assay media. The DMSO concentration is constant throughout the assay plate, including the negative and positive controls. The assay plate is incubated for 3 days at 37° C. in an incubator containing 5% $CO_2$. Cell viability is evaluated with the addition of 10 µL of CellTiter-Glo (ProMega). Luminescence is measured using an EnVision plate reader (Perkin Elmer). $EC_{50}$ values are calculated using the raw data from the CPE assays, respectively.

All compounds of the invention, namely compounds 1001-1222 are tested in the assay described in Example A. Compounds tested in the assay of Example A showed $EC_{50}$ values in the range of 10 µM or less. Representative data is shown below:

| Cmpd # | Ec50 (nM) Example A |
|---|---|
| 1002 | 260 |
| 1005 | 970 |
| 1016 | 1100 |
| 1018 | 730 |
| 1020 | 450 |
| 1027 | 10 |
| 1034 | 28 |
| 1036 | 140 |
| 1043 | 6400 |
| 1047 | 1700 |
| 1054 | 600 |
| 1058 | 8000 |
| 1061 | 29 |
| 1065 | 43 |
| 1068 | 63 |
| 1069 | 1200 |
| 1070 | 16 |
| 1074 | 2.8 |
| 1081 | 280 |
| 1085 | 280 |
| 1090 | 710 |
| 1095 | 380 |
| 1096 | 300 |
| 1097 | 93 |
| 1100 | 25 |
| 1104 | 130 |
| 1108 | 1600 |
| 1119 | 7700 |
| 1140 | 26 |
| 1142 | 480 |
| 1163 | 590 |
| 1164 | 1000 |
| 1168 | 280 |
| 1179 | 400 |
| 1180 | 1400 |
| 1183 | 470 |
| 1197 | 54 |
| 1198 | 21 |
| 1199 | 8.8 |
| 1200 | 29 |
| 1204 | 79 |
| 1205 | 6.6 |
| 1206 | 110 |

-continued

| Cmpd # | Ec50 (nM) Example A |
|---|---|
| 1212 | 15 |
| 1215 | 31 |
| 1218 | 380 |
| 1219 | 200 |
| 1221 | 170 |
| 1222 | 490 |

Each reference, including all patents, patent applications, and publications cited in the present application is incorporated herein by reference in its entirety, as if each of them is individually incorporated.

It would be appreciated that, in the above teaching of invention, the skilled in the art could make certain changes or modifications to the invention, and these equivalents would still be within the scope of the invention defined by the appended claims of the application.

The invention claimed is:

1. A compound of Formula (I), or a racemate, enantiomer, diastereoisomer or tautomer thereof:

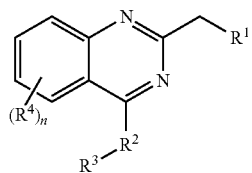

wherein:

$R^1$ is a 9 to 14 membered heterocycle or heteroaryl selected from the group consisting of

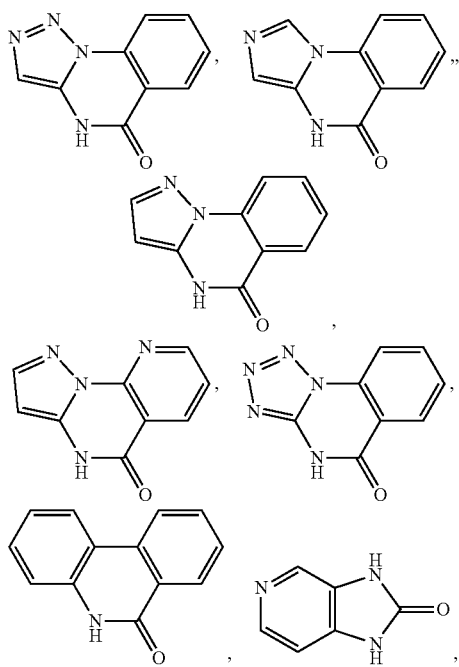

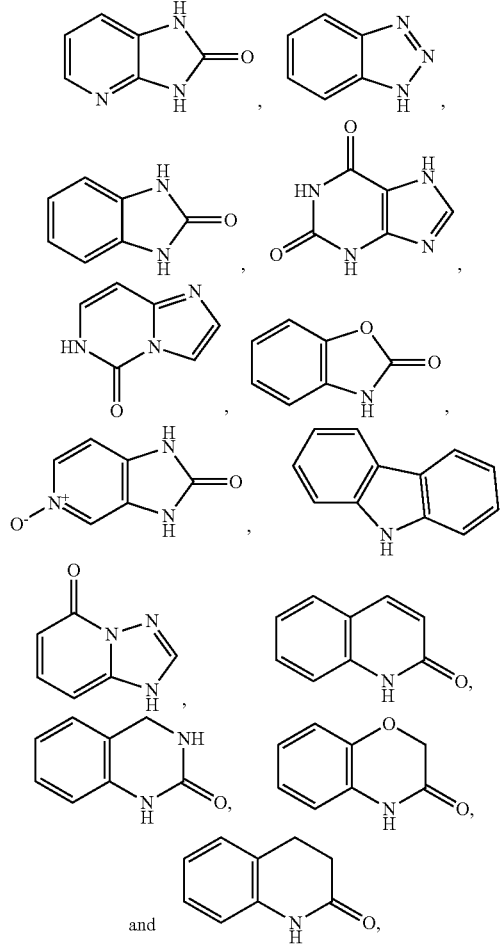

wherein said heteroaryl and heterocyclyl are optionally mono- or di-substituted with $(C_{1-6})$alkyl, halo, —CN, $(C_{1-6})$haloalkyl, OH, —O$(C_{1-6})$alkyl, —C(=O)OH, —C(=O)—O—$(C_{1-6})$alkyl or $(C_{3-7})$cycloalkyl, wherein $R^1$ is linked via the $CH_2$ moiety to the quinazoline through the hydrogen bearing ring nitrogen of said 9-14 membered heteroaryl or heterocyl by replacement of that hydrogen with $CH_2$-quinazoline;

$R^2$ is $(CH_2)$, $(CH_2)_2$, $(CH_2)_3$, $(CH_2)_4$, $(CH_2)_5$, $(CH_2)_6$, —O—, —S— or —$NR^{2A}$;

$R^{2A}$ is H or $(C_{1-6})$alkyl;

$R^3$ is $(C_{1-6})$alkyl, $(C_{3-7})$cycloalkyl, aryl, heteroaryl, heterocyclyl, —$(C_{1-6})$alky-$(C_{3-7})$cycloalkyl, —$(C_{1-6})$alkyl-aryl, —$(C_{1-6})$alkyl-heteroaryl or —$(C_{1-6})$alkyl-heterocyclyl, wherein each said alkyl, cycloalkyl, aryl, heteroaryl and heterocyclyl are optionally mono-, di- or tri-substituted with $R^{3A}$;

or wherein $R^{2A}$ and $R^3$ are linked together with the N to which they are attached to form a heterocycle optionally mono-, di- or tri-substituted with $R^{3A}$;

$R^{3A}$ is each independently selected from the group consisting of halo, oxo, —CN, OH, —COOH, —$(C_{1-6})$alkyl (optionally substituted with —OH), —O—$(C_{1-6})$alkyl, $(C_{3-7})$cycloalkyl, $(C_{1-6})$haloalkyl, —O—C(=O)—$R^{3B}$, —C(=O)—O—$R^{3B}$, —$SO_2NH_2$, —$SO_2$—N(H)$R^{3B}$, —$SO_2$—N(($C_{1-6})$alkyl)$_2$, —$SOR^{3B}$, —$SO_2R^{3B}$, —C(=O)—$NH_2$, —C(=O)—N(H)$R^{3B}$, —C(=O)—N(($C_{1-6})$alkyl)$_2$, —C(=O)—

NH—SO$_2$R$^{3B}$, —SO$_2$—NH—C(=O)R$^{3B}$, —NH$_2$, —N(H)R$^{3B}$, —N((C$_{1-6}$)alkyl)$_2$, —NH—C(=O)R$^{3B}$, —NH—C(=O)O—R$^{3B}$, —C(=O)—R$^{3B}$, and R$^{3B}$ (optionally substituted with (C$_{1-6}$)alkyl);

R$^{3B}$ is (C$_{1-6}$)alkyl, (C$_{3-7}$)cycloalkyl, aryl, heteroaryl or heterocyclyl;

R$^4$ is each independently selected from the group consisting of H, halo, —CN, OH, —COOH, —(C$_{1-6}$)alkyl, —O—(C$_{1-6}$)alkyl, (C$_{3-7}$)cycloalkyl, (C$_{1-6}$)haloalkyl, —C(=O)—O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO(C$_{1-6}$)alkyl, —SO$_2$(C$_{1-6}$)alkyl, —C(=O)—NH$_2$, —C(=O)—NH(C$_{1-6}$)alkyl, —C(=O)—N((C$_{1-6}$)alkyl)$_2$, —C(=O)—NH—SO$_2$(C$_{1-6}$)alkyl, —SO$_2$—NH—C(=O)—(C$_{1-6}$)alkyl, —NH$_2$, —NH(C$_{1-6}$)alkyl, —N((C$_{1-6}$)alkyl)$_2$, —NH(C$_{3-7}$)cycloalkyl, —N((C$_{1-6}$)alkyl)(C$_{3-7}$)cycloalkyl, —NH—C(=O)(C$_{1-6}$)alkyl, —NH—C(=O)O(C$_{1-6}$)alkyl and R$^{4a}$;

R$^{4a}$ is —(C$_{1-6}$)alkyl-heterocyclyl, —(C$_{1-6}$)alkyl-heteroaryl, heterocyclyl or heteroaryl, wherein each said heterocyclyl and heteroaryl is optionally mono-, di- or tri-substituted with (C$_{1-6}$)alkyl; and n is 0, 1, 2 or 3;

or a pharmaceutically acceptable salt thereof.

2. The compound according to claim 1, wherein

R$^2$ is (CH$_2$), (CH$_2$)$_2$, (CH$_2$)$_3$, (CH$_2$)$_4$, (CH$_2$)$_5$, (CH$_2$)$_6$, —O— or —NR$^{2A}$;

R$^{2A}$ is H or (CH), (CH)$_2$, (CH)$_3$, (CH)$_4$, (CH)$_5$, (CH)$_6$;

R$^3$ is aryl, heteroaryl, heterocyclyl, —(C$_{1-6}$)alkyl-(C$_{3-7}$)cycloalkyl, —(C$_{1-6}$)alkyl-aryl, —(C$_{1-6}$)alkyl-heteroaryl or —(C$_{1-6}$)alkyl-heterocyclyl, wherein each said cycloalkyl, aryl, heteroaryl and heterocyclyl are optionally mono-, di- or tri-substituted with R$^{3A}$;

R$^{3A}$ is each independently selected from the group consisting of halo, —CN, OH, —COOH, —(C$_{1-6}$)alkyl, —O—(C$_{1-6}$)alkyl, (C$_{3-7}$)cycloalkyl, (C$_{1-6}$)haloalkyl, —O—C(=O)—(C$_{1-6}$)alkyl, —C(=O)—O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO(C$_{1-6}$)alkyl, —SO$_2$(C$_{1-6}$)alkyl, —C(=O)—NH$_2$, —C(=O)—NH(C$_{1-6}$)alkyl, —C(=O)—N((C$_{1-6}$)alkyl)$_2$, —C(=O)—NH—SO$_2$(C$_{1-6}$)alkyl, —SO$_2$—NH—C(=O)—(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl, —NH—C(=O)O(C$_{1-6}$)alkyl, heterocyclyl (optionally substituted with (C$_{1-6}$)alkyl) and heteroaryl (optionally substituted with (C$_{1-6}$)alkyl;

or a pharmaceutically acceptable salt thereof.

3. The compound according to claim 2, wherein

R$^2$ is —O— or —NR$^{2A}$;

R$^{2A}$ is H or (CH), (CH)$_2$, (CH)$_3$, (CH)$_4$ (CH)$_5$, (CH)$_6$;

R$^3$ is heteroaryl, heterocyclyl, —(C$_{1-6}$)alkyl-heteroaryl or —(C$_{1-6}$)alkyl-heterocyclyl, wherein each said heteroaryl and heterocyclyl are optionally mono, di- or tri-substituted with R$^{3A}$;

R$^{3A}$ is each independently selected from the group consisting of halo, oxo, —CN, OH, —COOH, —(C$_{1-6}$)alkyl (optionally substituted with —OH), —O—(C$_{1-6}$)alkyl, (C$_{3-7}$)cycloalkyl, (C$_{1-6}$)haloalkyl, —O—C(=O)—(C$_{1-6}$)alkyl, —C(=O)—O—(C$_{1-6}$)alkyl, —SO$_2$NH$_2$, —SO$_2$—NH(C$_{1-6}$)alkyl, —SO$_2$—N((C$_{1-6}$)alkyl)$_2$, —SO(C$_{1-6}$)alkyl, —SO$_2$(C$_{1-6}$)alkyl, —C(=O)—NH$_2$, —C(=O)—NH(C$_{1-6}$)alkyl, —C(=O)—N((C$_{1-6}$)alkyl)$_2$, —C(=O)—NH—SO$_2$(C$_{1-6}$)alkyl, —SO$_2$—NH—C(=O)—(C$_{1-6}$)alkyl, —NH$_2$, —NH(C$_{1-6}$)alkyl, —N((C$_{1-6}$)alkyl)$_2$, —NH—C(=O)(C$_{1-6}$)alkyl, —NH—C(=O)O(C$_{1-6}$)alkyl, heterocyclyl (optionally substituted with (C$_{1-6}$)alkyl) and heteroaryl (optionally substituted with (C$_{1-6}$)alkyl;

or a pharmaceutically acceptable salt thereof.

4. The compound according to claim 1, wherein

R$^4$ is each independently selected from the group consisting of H, halo, —CN, OH, —(C$_{1-6}$)alkyl, —O—(C$_{1-6}$)alkyl, (C$_{3-7}$)cycloalkyl, (C$_{1-6}$)haloalkyl and R$^{4a}$;

R$^{4a}$ is heterocyclyl or heteroaryl, wherein each said heterocyclyl and heteroaryl is optionally mono-, di- or tri-substituted with (C$_{1-6}$)alkyl; or a pharmaceutically acceptable salt thereof.

5. The compound according to claim 4, wherein R$^4$ is each independently selected from the group consisting of H, halo, —CN, OH, —(C$_{1-6}$)alkyl, —O—(C$_{1-6}$)alkyl, (C$_{3-7}$)cycloalkyl and (C$_{1-6}$)haloalkyl; or a pharmaceutically acceptable salt thereof.

6. The compound according to claim 1, wherein n is 0 or 1; or a pharmaceutically acceptable salt thereof.

7. The compound according to claim 6, wherein n is 0; or a pharmaceutically acceptable salt thereof.

8. A pharmaceutical composition comprising a compound according to claim 1, or a pharmaceutically acceptable salt thereof, and a pharmaceutically acceptable carrier.

9. A method of treatment of RSV infection comprising administering to a subject in need thereof an effective amount of a compound of claim 1.

10. The compound according to claim 3, wherein

R$^4$ is each independently selected from the group consisting of H, halo, —CN, OH, —(C$_{1-6}$)alkyl, —O—(C$_{1-6}$)alkyl, (C$_{3-7}$)cycloalkyl, (C$_{1-6}$)haloalkyl and R$^{4a}$;

R$^{4a}$ is heterocyclyl or heteroaryl, wherein each said heterocyclyl and heteroaryl is optionally mono-, di- or tri-substituted with (C$_{1-6}$)alkyl; or a pharmaceutically acceptable salt thereof.

11. The compound according to claim 10, wherein R$^4$ is each independently selected from the group consisting of H, halo, —CN, OH, —(C$_{1-6}$)alkyl, —O—(C$_{1-6}$)alkyl, (C$_{3-7}$)cycloalkyl and (C$_{1-6}$)haloalkyl; or a pharmaceutically acceptable salt thereof.

12. The compound according to claim 5, wherein n is 0 or 1; or a pharmaceutically acceptable salt thereof.

13. The compound according to claim 11, wherein n is 0 or 1; or a pharmaceutically acceptable salt thereof.

14. The compound according to claim 12, wherein n is 0; or a pharmaceutically acceptable salt thereof.

15. The compound according to claim 1, wherein n is 0; or a pharmaceutically acceptable salt thereof.

* * * * *